(12) United States Patent
Corbett et al.

(10) Patent No.: US 10,245,262 B2
(45) Date of Patent: Apr. 2, 2019

(54) IMMUNOLOGICAL REAGENTS AND USES THEREFOR

(71) Applicants: THE UNIVERSITY OF QUEENSLAND, St. Lucia, Queensland (AU); Monash University, Clayton, Victoria (AU); THE UNIVERSITY OF MELBOURNE, Victoria (AU)

(72) Inventors: Alexandra Jane Corbett, Victoria (AU); James McCluskey, Victoria (AU); Lars Kjer-Nielsen, Victoria (AU); Zhenjun Chen, Victoria (AU); Jamie Rossjohn, Victoria (AU); Onisha Patel, Victoria (AU); Richard William Birkinshaw, Victoria (AU); Sidonia Barbara Guiomar Eckle, Victoria (AU); David Paul Fairlie, Queensland (AU); Ligong Liu, Queensland (AU); Jeffrey Yam Wing Mak, Queensland (AU)

(73) Assignees: The University of Queensland, St. Lucia (AU); Monash University, Clayton (AU); The University of Melbourne, Victoria (AU)

( * ) Notice: Subject to any disclaimer, the term of this patent is extended or adjusted under 35 U.S.C. 154(b) by 0 days.

(21) Appl. No.: 15/300,023

(22) PCT Filed: Apr. 1, 2015

(86) PCT No.: PCT/AU2015/050148
§ 371 (c)(1),
(2) Date: Sep. 28, 2016

(87) PCT Pub. No.: WO2015/149130
PCT Pub. Date: Oct. 8, 2015

(65) Prior Publication Data
US 2017/0209442 A1 Jul. 27, 2017

(30) Foreign Application Priority Data

Apr. 1, 2014 (AU) ................................ 2014901185
Apr. 1, 2014 (AU) ................................ 2014901186

(51) Int. Cl.
| | | |
|---|---|---|
| C07D 239/54 | (2006.01) |
| A61K 31/513 | (2006.01) |
| C07D 239/545 | (2006.01) |
| C07K 14/74 | (2006.01) |
| C07D 239/60 | (2006.01) |
| G01N 33/569 | (2006.01) |
| A61K 47/55 | (2017.01) |
| A61K 47/64 | (2017.01) |
| A61K 38/00 | (2006.01) |

(52) U.S. Cl.
CPC ............ *A61K 31/513* (2013.01); *A61K 47/55* (2017.08); *A61K 47/6425* (2017.08); *C07D 239/54* (2013.01); *C07D 239/545* (2013.01); *C07D 239/60* (2013.01); *C07K 14/70539* (2013.01); *G01N 33/56972* (2013.01); *A61K 38/00* (2013.01); *G01N 2333/70539* (2013.01); *G01N 2800/26* (2013.01)

(58) Field of Classification Search
CPC .............. C07D 239/54; C07D 239/545; C07D 239/60; A61K 31/513
USPC .......................................... 544/311; 514/274
See application file for complete search history.

(56) References Cited

U.S. PATENT DOCUMENTS

2011/0152273 A1  6/2011 Arikawa et al.

FOREIGN PATENT DOCUMENTS

WO  WO 2008/043544 A1  4/2008
WO  WO 2014/005194 A1  1/2014

OTHER PUBLICATIONS

Corbett et al., T-cell activation by transitory neo-antigens derived from distinct microbial pathways, Nature, vol. 509, pp. 361-365, (16 pages total including experimental data) 2014.*
Gura et al., Systems for identifying new drugs are often faulty, Science, 278:1041-1042 (1997).*
Johnson et al., Relationships between drug activity in NCI preclinical in vitro and in vivo models and early clinical trials, British Journal of Cancer, 84(10): 1424-1431 (2001).*
Simone, Oncology: Introduction, Cecil Textbook of Medicine, 20th Edition, vol. 1, pp. 1004-1010 (1996).*
Pearce et al., Failure modes in anticancer drug discovery and development, Cancer Drug Design and Discovery Edited by Stephen Neidle, Chapter 18, pp. 424-435 (2008).*
Li, Youzhi et al., Suppression of cancer relapse and metastasis by inhibiting cancer sternness, PNAS, vol. 112, No. 6, pp. 1839-1844 (2015).*
Bosseray et al., PubMed Abstract (Pathol Biol (Paris) 50(8): 483-92), 2002.*
Razonable et al., PubMed Abstract (Herpes 10(3): 60-5), 2003.*
Goff, PubMed Abstract (J Gene Med 3(6): 517-28), 2001.*
Douglas, Jr., Introduction to Viral Diseases, Cecil Textbook of Medicine, 20th Edition, vol. 2, pp. 1739-1747 (1996).*
CAS Registry No. 34941-71-4; STN Entry Date: Nov. 16, 1984; 1 page.
CAS Registry No. 1456437-98-1; STN Entry Date: Oct. 6, 2013; 1 page.
CAS Registry No. 1550025-85-8; STN Entry Date: Feb. 19, 2014; 1 page.
CAS Registry No. 1518068-01-3; STN Entry Date: Jan. 13, 2014; 1 page.

(Continued)

*Primary Examiner* — Deepak R Rao
(74) *Attorney, Agent, or Firm* — McCarter & English, LLP; Maria Laccotripe Zacharakis

(57) ABSTRACT

The present invention provides ligands which bind to MR1, some of which induce MR1 to bind to MAIT cells thereby activating or inhibiting MAIT cell activation.

20 Claims, 32 Drawing Sheets

Specification includes a Sequence Listing.

(56) References Cited

OTHER PUBLICATIONS

CAS Registry No. 1552919-96-6; STN Entry Date: Feb. 23, 2014; 1 page.

Kis, K. et al., "Biosynthesis of Riboflavin. The Reaction Catalysed by 6,7-Dimethyl-8-ribityllumazine Synthase can Proceed Without Catalysis Under Physiological Conditions." Flavins and Flavoproteins 1999, Proceedings of the International Symposium, 13th, Konstanz, Germany, 1999; pp. 833-836.

Schramek, N. et al., "Single Turnover Kinetic Analysis of 6,7-Dimethyl-8-ribityllumazine Synthase from *Bacillus subtilis*." Flavins and Flavoproteins 2002, Proceedings of the International Symposium, 14th, Cambridge, UK, 2002; pp. 363-368.

Talukdar, A. et al., "*O*-Nucleoside, *S*-Nucleoside, and *N*-Nucleoside Probes of Lumazine Synthase and Riboflavin Synthase." *J Org Chem.* 77(14): 2012; pp. 6239-6261.

\* cited by examiner

FIGURE 4
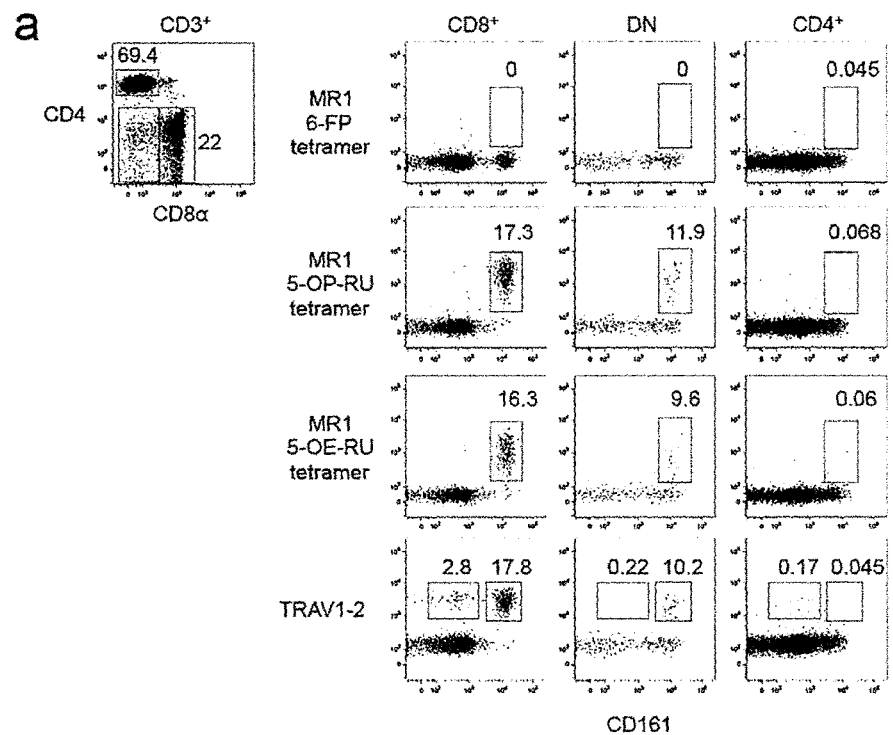
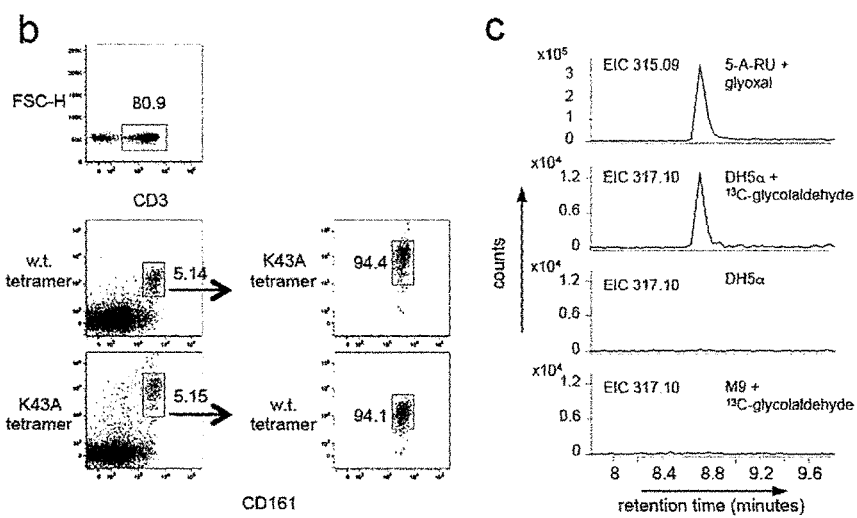

FIGURE 4 (cont'd)
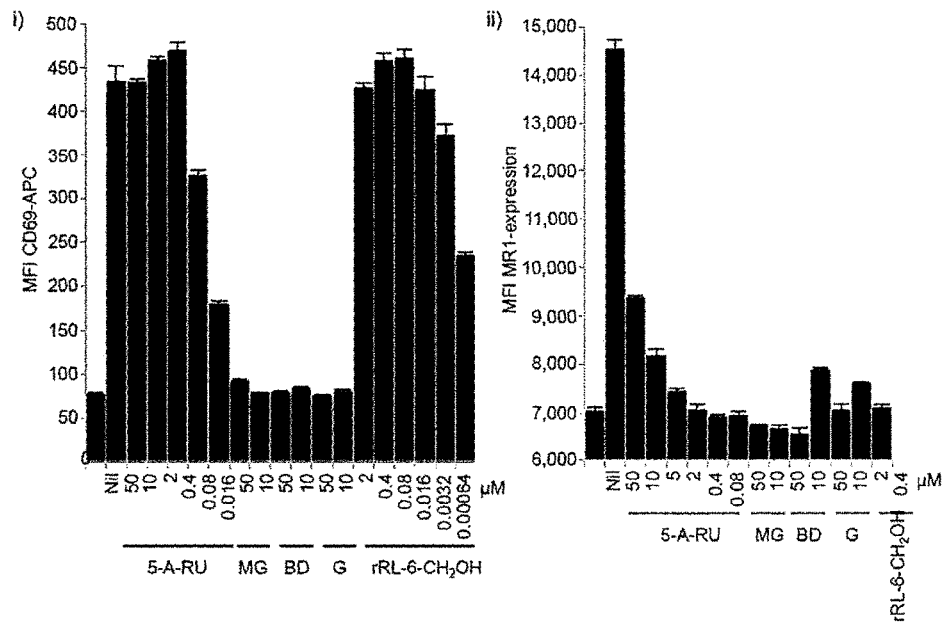
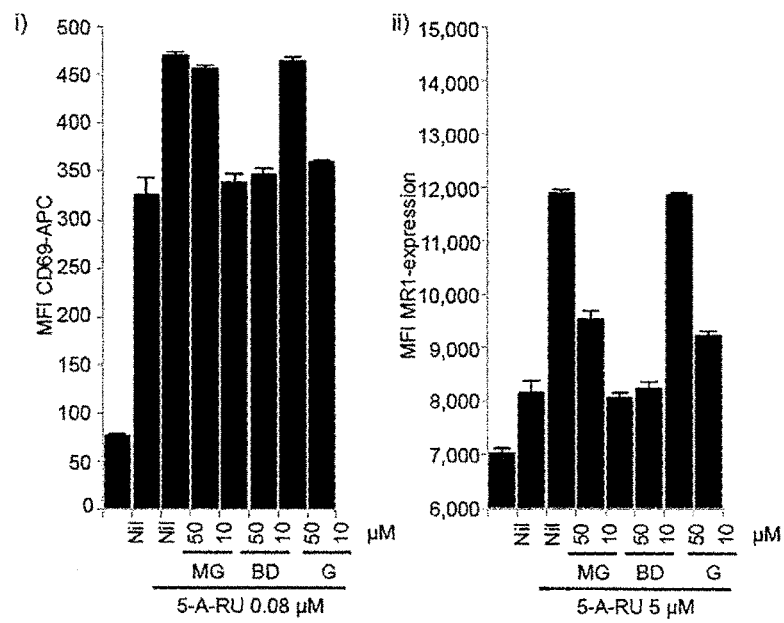

FIGURE 6
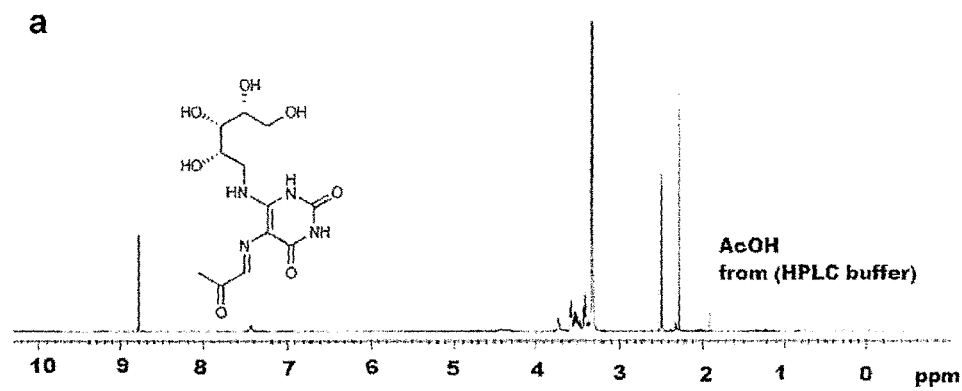
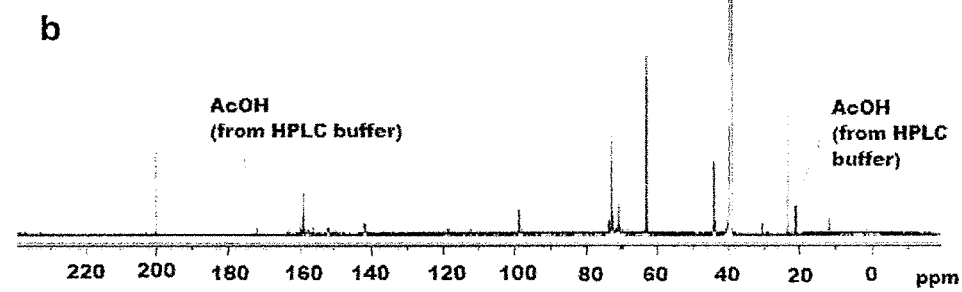
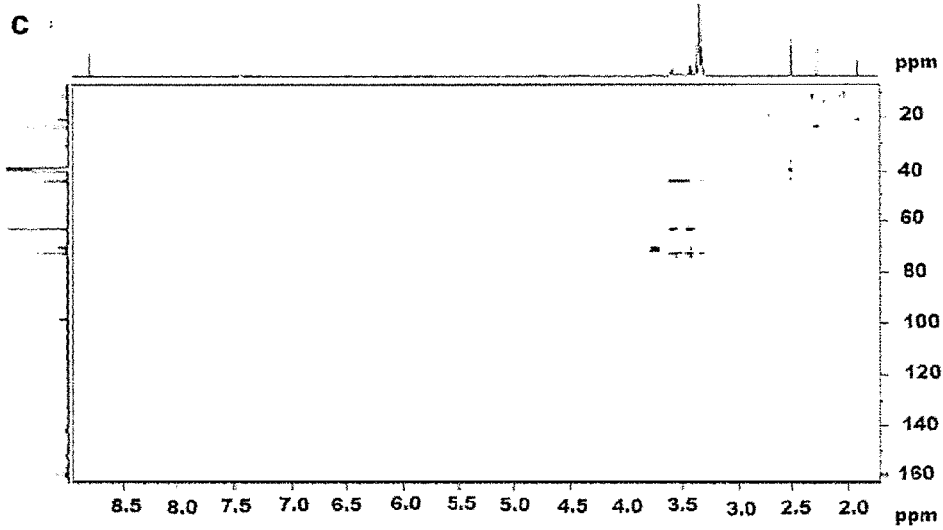

FIGURE 13 Data collection and refinement statistics. Values in parentheses refer to the highest-resolution bin. The $R_{factor}$ was calculated from all data except for 5% that was used for the $R_{free}$ calculation.

|  | MAIT-MR1-5-OP-RU | MAIT-MR1-5-OE-RU | MAIT-K43A-MR1-5-OP-RU |
|---|---|---|---|
| Data collection | | | |
| Temperature | 100K | 100K | 100K |
| Space group | C2 | C2 | C2 |
| Cell dimensions | | | |
| $a, b, c$ (Å) | 218.76, 71.11, 144.28 | 218.11, 70.60, 143.86 | 215.58, 68.87, 142.98 |
| $a, b, g$ (°) | 90, 104.87, 90 | 90, 104.63, 90 | 90, 104.86, 90 |
| Resolution (Å) | 33.42-2.50 (2.55-2.50) | 75.41-2.10 (2.21-2.10) | 50.00-2.20 (2.3-2.20) |
| $R_{pim}$* | 9.4 (38.8) | 6.1 (35.2) | 5.9 (36.7) |
| $I/\sigma_I$ | 7.8 (2.3) | 8.1 (2.1) | 9.7 (2.3) |
| Completeness (%) | 100 (100) | 98.6 (97.1) | 97.9 (97.4) |
| Total N° observations | 307877 (19059) | 462978 (62837) | 509054 (74702) |
| N° unique observations | 74555 (4584) | 122109 (17496) | 101222 (14608) |
| Multiplicity | 4.1 (4.2) | 3.8 (3.6) | 5.0 (5.1) |
| | | | |
| Refinement statistics | | | |
| $R_{factor}$† (%) | 16.5 | 18.4 | 20.8 |
| $R_{free}$‡ (%) | 21.6 | 22.2 | 24.5 |
| No. atoms | | | |
| • Protein | 12424 | 12396 | 12514 |
| • Ligand | 45 | 42 | 46 |
| • Water | 1044 | 900 | 488 |
| | | | |
| Ramachandran plot (%) | | | |
| • Most favoured | 97.4 | 91.4 | 91.5 |
| • Allowed region | 2.5 | 8.6 | 8.5 |
| $B$-factors (Å²) | | | |
| • Protein | 29.8 | 37.9 | 37.4 |
| • ligand | 14.8 | 23.8 | 26 |
| | | | |
| rmsd bonds (Å) | 0.010 | 0.010 | 0.010 |
| rmsd angles (°) | 1.16 | 1.05 | 1.08 |

\* $R_{p.i.m} = \Sigma_{hkl} [1/(N-1)]^{1/2} \Sigma_i | I_{hkl,i} - \langle I_{hkl} \rangle | / \Sigma_{hkl} \langle I_{hkl} \rangle$ † $R_{factor} = ( \Sigma | |F_o| - |F_c| | ) / ( \Sigma |F_o| )$ - for all data except as indicated for ‡.

FIGURE 14
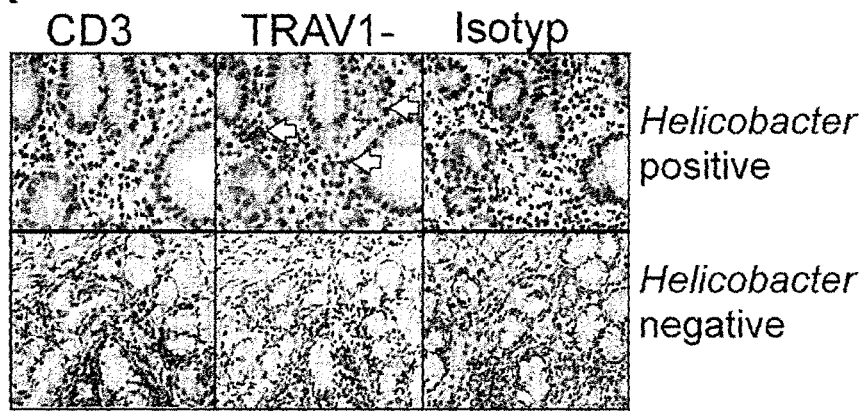
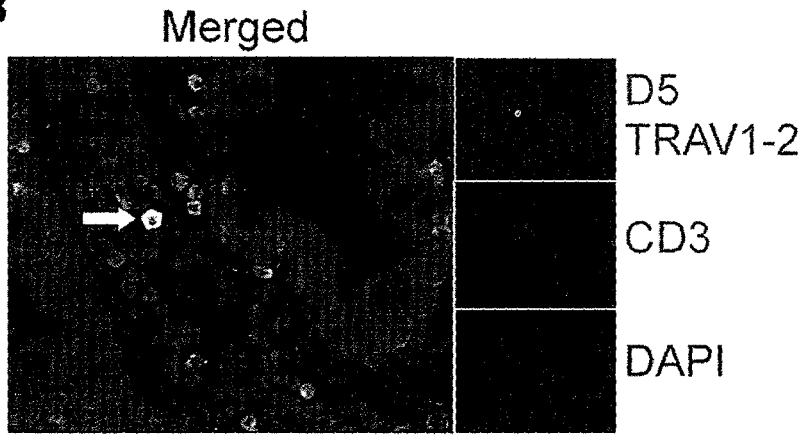
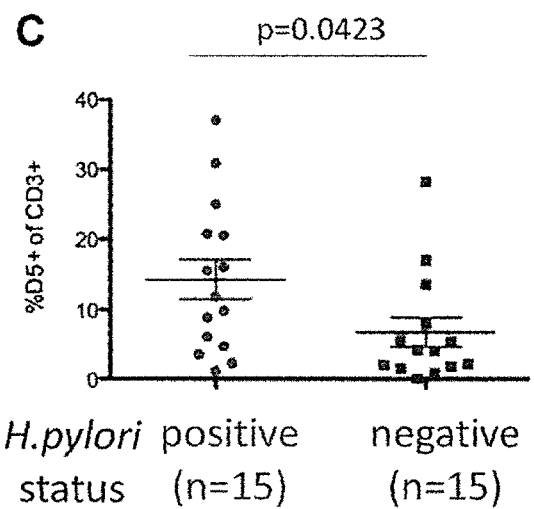

FIGURE 21
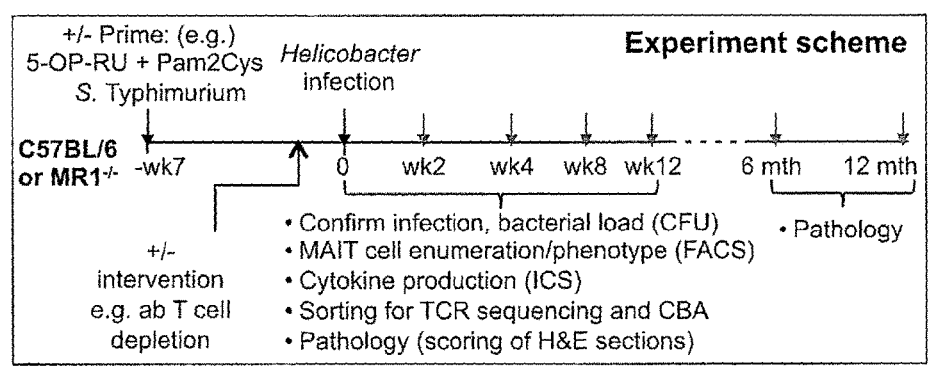
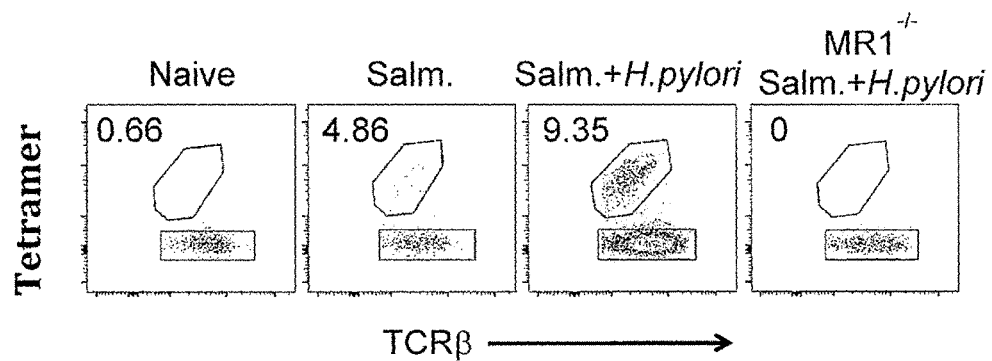

FIGURE 24
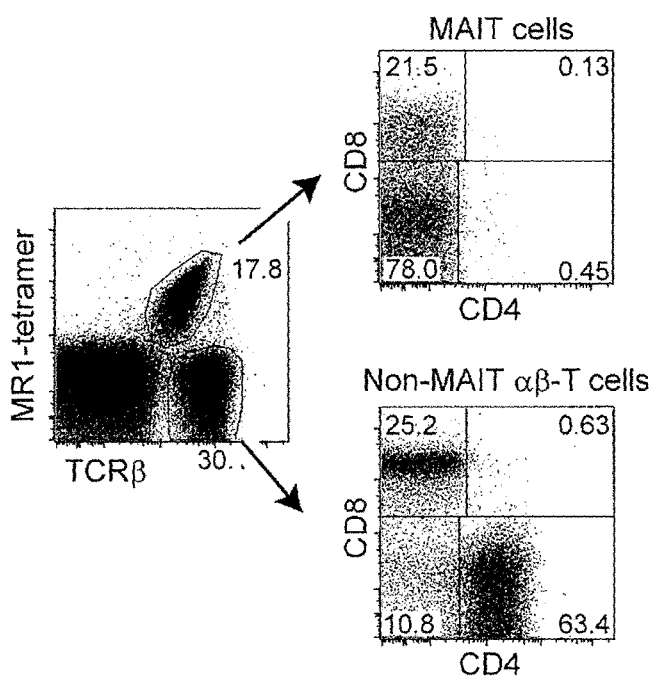
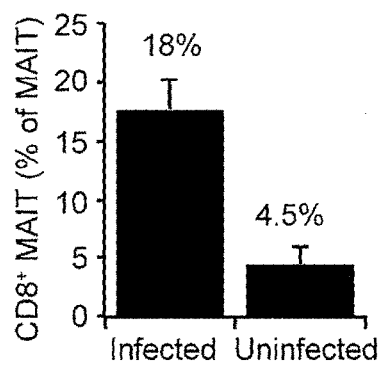
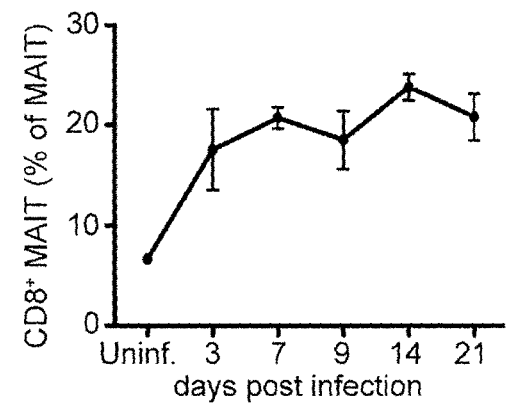

IMMUNOLOGICAL REAGENTS AND USES THEREFOR

RELATED APPLICATIONS

This application is a 35 U.S.C. § 371 national stage filing of International Application No. PCT/AU2015/050148, filed on Apr. 1, 2015, which claims priority to Australian Patent Application No. 2014901185, filed on Apr. 1, 2014 and Australian Patent Application No. 2014901186, filed on Apr. 1, 2014. The entire contents of each of the foregoing applications are incorporated herein by reference.

FIELD

The present invention relates generally to the field of immunology and medicinal chemistry, including small organic compounds and bound complexes thereof that either activate or block T cell activation and are useful for the detection and monitoring of components in the immune system. Immunological reagents are also provided which are useful in detecting and determining the state of the adaptive cellular immune response system and which are useful for the treatment or prevention of conditions associated with aberrant MAIT cell activity or which require MAIT cell activity.

SEQUENCE LISTING

The instant application contains a Sequence Listing which has been submitted electronically in ASCII format and is hereby incorporated by reference in its entirety. Said ASCII copy, created on Apr. 9, 2017, is named 3525739_ST25.txt and is 12,383 bytes in size.

BACKGROUND

Cellular immune responses are often initiated by T cells bearing αβ-T cell receptors (TCRs) which typically recognize foreign peptides bound to classical major histocompatibility complex (MHC) molecules on specialized antigen presenting cells (Zinkernagel and Doherty, 1997). There are two classes of MHC molecules—MHC class I (MHC-I) and MHC class II (MHC-II). Within MHC-I, there are two subclasses, MHC-Ia ('classical' MHC) and MHC-Ib ('non-classical' MHC).

Major histocompatibility complex-related protein 1 (MR1) is a MHC class Ib molecule encoded by a single functional, monomorphic Mr1 gene in antigen presenting cells. The MR1 protein, like MHC class I, is comprised of a heavy chain (comprised of the α1, α2 and α3 domains) non-covalently associated with a light chain (β2-microglobulin). The Mr1 gene is not Mhc linked, is highly conserved, and seems to be unique to mammals. As striking evidence for interspecies conservation, the predicted amino acid sequences of mouse MR1 (mMR1) and human MR1 are 89/90% identical in their 1/2 domains. By contrast, mouse and human MHC-linked class Ia and Ib molecules are 69/70% and 51/41% identical, respectively. The high level of polymorphism of classical MHC molecules allows them to present diverse peptides to T cells during the adaptive immune response to pathogens. By contrast, the remarkable conservation of MR1 suggests that it evolved under strong negative selection, possibly imposed by immune responses to pathogens. MR1 message and protein are ubiquitously expressed in different tissues. Endogenous MR1 is only detected on the plasma membrane of cells from murine or human origins at very low levels using available monoclonal antibodies (mAbs) considered specific for MR1. However, higher levels of surface expression of MR1 can be achieved using transfection or transduction to overexpress an MR1-encoding cDNA in mouse or human cell lines. The failure to detect even moderate levels of endogenous MR1 at the cell surface is suggested to reflect limited ligand supply as is the case with the non-classical MHC, H2-M3, which presents N-formylated peptides.

MR1 cell surface expression is required for the in vivo development of a recently identified population of mucosal-associated T (MAIT) cells that are typically classified as possessing an invariant TCR-chain (i.e. identical V-J combination).

The importance of the role of MAIT cells in immunity is indicated by their conservation across species such as humans, cattle and mice, as well as recent data implying protective function in certain infections, e.g. in vivo pulmonary bacterial infections (Gold et al., 2010a; Le Bourhis et al., 2011; Le Bourhis et al., 2010, Mejerovics A et al., 2013; Serriari N E et al., (2014)) and inflammatory conditions including multiple sclerosis. In humans, MAIT cells comprise 1-10% of peripheral blood T cells when compared to their NKT cell counterparts (typically less than 0.1%) (Godfrey et al., 2010b). Indeed, MAIT cells are found in human blood, the gastrointestinal mucosa and mesenteric lymph nodes. Furthermore, MAIT cells, like NKT cells, rapidly produce a broad range of cytokines upon activation (Kawachi et al., 2006; Martin et al., 2009). There are further parallels between MR1-restricted MAIT cells and CD1d-restricted NKT cells in that, like NKT cells, MAIT cells typically express a semi-invariant TCR, comprised of an invariant TCR alpha-chain (V 19J 33 in mice or the homologous V 7.2J 33 in humans) in combination with TCR-V 6 or V 8 in mice and TCR-V 2 or V 13 in humans. Other alpha chains have been described, for example, Vα7.2 joined to Jα20 or Jα12 (Rentragoon et al (2013). The semi-invariant and evolutionarily conserved nature of the MAIT TCR suggests that MAIT cells are specific for an important, albeit limited and atypical, class of antigens (Ags) presented by the MR1 molecule. Further, evidence for a highly conserved MAIT-ligand comes from mutagenesis studies of MAIT TCRs with different Vβ-segments which have revealed that a defined cluster of amino acid residues are crucial for MAIT cell recognition of diverse microbes (Reantragoon et al, 2012). MAIT cells respond to a surprisingly broad range of microorganisms, excluding viruses but including diverse strains of bacteria and yeast, suggesting the existence of a conserved Ag (or family of Ag), common to these cellular organisms, presented to MAIT cells in an MR1-dependent manner (Gold et al., 2010a; Gold et al., 2010b; Le Bourhis et al., 2010). This suggests a much broader role in the immune response than is indicated by their limited TCR repertoire.

In humans, MAIT cells are traditionally defined as $CD161^{hi}$, IL-18R, $^+$V 7.2$^+$, $^-$CD3$^+$ lymphocytes. Current methods of staining of MAIT cells in both peripheral blood and tissues require either staining for CD161 or IL-18R expression at the cell surface, together with staining of the V 7.2 segment (Martin et al, 2009; Le Bourhis et al, 2010). A key limitation of this phenotypic characterization of MAIT cells is that these cells may include T cells other than those expressing the V 7.2. Moreover, T cells that do express the V 7.2 also occur in the normal course of other immune responses including MHC-restricted responses and potentially other MHC1b-restricted immunity and therefore these V 7.2$^+$ cells are unrelated to MAIT cell specificity. Hence, the monitoring and identification of MAIT cells by current techniques reliant entirely on a V 7.2 phenotype is subject to a significant 'false-positive' effect. In addition, the precise identification of MAIT cells in mice has been even more difficult, as they are traditionally defined using V 19 and V 6 or V 8.

Because of the emerging understanding of the role that MAIT cells play in the immune response, there is a need to identify the exact mechanisms by which MAIT cells exert their effects. This has been significantly hindered because prior to the present invention the precise identity of the MR1-restricted Ag(s) which represents a key step in understanding MAIT cell biology has been unknown.

Thus, there remains a need for new tools to specifically recognize MAIT cells in mammals, which would be useful, inter alia, for recognizing, purifying, and enriching these cells in vivo or in vitro, to allow the facilitation of methods of labeling MAIT cells for research and diagnostic purposes. There also remains a need to identify the ligand(s) bound by MR1, including determining the TCR antigen specificity of MAIT cells which will allow the facilitation of methods of modulating MAIT cell activity for therapeutic purposes.

SUMMARY OF THE INVENTION

The present invention is predicated in part on the identification of compounds that act as ligands, which interact with MR1 to form potent MAIT-activating antigens. These ligands enable production of reagents that specifically identify MAIT cells and allow for the detection and state of stimulation of MAIT cells. These ligands further enable production of therapeutics that mediate their actions through binding to MR1. The ability to ascertain MAIT cell presence and level of stimulation enables an assessment of the state of the adaptive cellular immune response system in a subject and the development of therapeutic methods for the treatment or prophylaxis of conditions associated with aberrant MAIT cell activity.

The present specification provides methods and immunological reagents useful for labeling MAIT cells. The present specification further provides ligands and compounds useful for modulating MAIT cell activity. Also, provided herein are ligands and compounds which interact with MR1, MR1-ligand subunits and stable multimeric complexes comprising same. The MR1-ligand subunit and complexes comprising same are recognised by T-cell receptors (TCRs) on MAIT cells, thereby allowing for the Labeling, identification, isolation and characterisation of MAIT cells and for the modulation of MAIT cell activity. The present invention enables development of methods of MAIT cell detection for both research and diagnostic purposes. The present invention further provides therapeutic methods to treat or prevent disease conditions associated with aberrant MAIT cell activity. The present invention also provides inhibitors and activators of MAIT cell function based on the identification and characterization of the MR1-restricted antigens.

The MR1 molecule on an antigen presenting cell or in soluble form comprises an heavy chain comprising domains 1, 2 and 3 and a 2-microglobulin light chain.

The monomeric form of MR1 (i.e. a single MR1) is referred to herein as an "MR1 subunit" and is represented by [MR1].

When a ligand is bound to MR1, this is represented as:

[MR1-L]

MR1 is as defined as above; and L is a ligand including a naturally occurring antigen or an artificially created ligand.

MR1 can form multimeric structures facilitated by a multi-valence binding molecule. Hence, the formula:

[MR1]$_n$ means a complex of two or more MR1 subunits up to n, which is the valence number of the multi-valence binding molecule.

When the MR1 subunit is bound with a ligand, and it is in multimeric form, it is represented as:

[MR1-L]$_n$

In an aspect, the present invention provides [MR1-L], wherein the ligand is represented by formula (I):

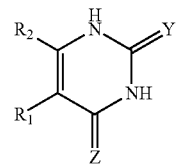

or a salt, solvate, tautomer, or stereoisomer thereof wherein:

$R_1$ is selected from the group consisting of:
—X—C(O)—$R_1$' (where $R_1$' is H, or optionally substituted $C_1$-$C_6$alkyl, and X is independently a bond or a divalent linker selected from the group consisting of $C_1$-$C_3$ optionally substituted alkylene, —N$R_2$'— optionally substituted $C_1$-$C_3$alkylene-, —O— optionally substituted $C_1$-$C_3$alkylene-, —S— optionally substituted $C_1$-$C_3$alkylene-, —S(O)— optionally substituted $C_1$-$C_3$alkylene-, —N=C$R_2$'—, —C$R_2$'=C$R_2$", —N$R_2$'—C(O), —O—C(O)—, or —S—C(O)— where each $R_2$' and $R_2$" is independently selected from H, halogen, CN, or optionally substituted $C_1$-$C_6$alkyl); —X'—C(O)N$R_3$'$R_4$' (where $R_3$' is H or optionally substituted $C_1$-$C_6$alkyl and $R_4$' is optionally substituted $C_1$-$C_6$alkyl, OH, or CN or $R_3$'$R_4$' together form an optionally substituted heterocyclyl or optionally substituted heteroaryl, and X' is independently a bond or a $C_1$-$C_3$ optionally substituted alkylene); —X"—C(O)O$R_5$' (wherein $R_5$' is H or optionally substituted $C_1$-$C_6$alkyl, and X" is independently a bond or a $C_1$-$C_3$ optionally substituted alkylene); —X'"—C(O)NHSO$_2$$R_6$' (wherein $R_6$' is optionally substituted aryl, or optionally substituted $C_1$-$C_6$alkyl, and X'" is independently a bond or a $C_1$-$C_3$ optionally substituted alkylene); and —X""—S(O)$_2$NH$R_7$' (wherein $R_7$' is H, optionally substituted $C_1$-$C_6$alkyl, or optionally substituted aryl, and X"" is independently a bond or a $C_1$-$C_3$ optionally substituted alkylene);

$R_2$ is selected from the group consisting of optionally substituted $C_{1-8}$alkyl, —NH(optionally substituted $C_{1-6}$alkyl), —N(optionally substituted $C_{1-6}$alkyl)(optionally substituted aryl), —N(optionally substituted $C_{1-6}$alkyl)$_2$, —O(optionally substituted $C_{1-6}$alkyl), —OC(O)($C_{1-6}$alkyl), —S(optionally substituted $C_{1-6}$alkyl), —SC(O)($C_{1-6}$alkyl), and —S(O)(optionally substituted $C_{1-6}$alkyl); and Y and Z are independently selected from the group consisting of oxo, thio, imino, mono-$C_{1-3}$ alkylimino, mono-$C_{1-3}$ acylimino, urea, mono-$C_{1-3}$ alkylurea, thiourea, mono-$C_{1-3}$alkylthiourea, guanidine, mono-$C_{1-3}$ alkylguanidino, and di-$C_{1-3}$alkylguanidino.

In an embodiment:

$R_1$ is —X—C(O)—$R_1'$ (where $R_1'$ is H, or optionally substituted $C_1$-$C_6$alkyl, and X is independently a divalent linker selected from the group consisting of $C_1$-$C_3$ optionally substituted alkylene, —$NR_2'$— optionally substituted $C_1$-$C_3$alkylene-, —O— optionally substituted $C_1$-$C_3$alkylene-, —N=$CR_2'$—, —$CR_2'$=$CR_2''$—, —$NR_2'$C(O)—, —OC(O)—, or —SC(O)— where each $R_2'$ and $R_2''$ is independently selected from H or optionally substituted $C_1$-$C_6$alkyl; and $R_2$ is selected from the group consisting of optionally substituted $C_{1-8}$alkyl, NH(optionally substituted $C_{1-6}$alkyl), —N(optionally substituted $C_{1-6}$allyl)(optionally substituted aryl), —N(optionally substituted $C_{1-6}$alkyl)$_2$, —O(optionally substituted $C_{1-6}$alkyl), —OC(O)($C_{1-6}$alkyl), —S(optionally substituted $C_{1-6}$alkyl), —SC(O)($C_{1-6}$alkyl), or —S(O)(optionally substituted $C_{1-6}$alkyl).

In an embodiment:

$R_1$ is —X—C(O)$R_1'$ where $R_1'$ is H or $C_{1-6}$alkyl and X is independently —$NR_2'$—$CH_2$—, —N=$CR_2'$—, —$CR_2'$=$CR_2''$—, —$NR_2'$—C(O)—, —OC(O)—, or —SC(O)— where $R_2'$ and $R_2''$ are independently H or $C_{1-6}$alkyl; and $R_2$ is —NH—$C_2$-$C_6$ alkyl optionally substituted 1 to 6 times with OH, $OR_1'$, $NH_2$, $NHR_1'$, $NR_1'R_2'$, SH, or $SR_1'$, where $R_1'$ and $R_2'$ are independently $C_{1-6}$alkyl, $C_{1-6}$acyl, $C_{1-6}$amido, or $C_{1-6}$thioamido.

In an embodiment:

$R_1$ is —N=$CR_2'$—C(O)$R_1'$ or —CH=$CR_2''$—C(O)$R_1'$, where each $R_1'$ and $R_2'$ is independently H or $C_{1-6}$alkyl; and $R_2$ is —NH—$C_2$-$C_6$ alkyl optionally substituted 1 to 4 times with OH.

In an embodiment, $R_1'$ is H or $C_1$-$C_6$alkyl optionally substituted by a group selected from halogen, hydroxy, mercapto, amino or amido.

In an embodiment both Y and Z are O.

In an embodiment Y is O and Z is S.

In an embodiment Y is S and Z is O.

In an embodiment Y is O and Z is imino.

In an embodiment Y is imino and Z is O.

In an embodiment Y is mono-$C_{1-3}$alkylimino and Z is O.

In an embodiment Y is O and Z is mono-$C_{1-3}$acylimino.

In an embodiment the ligand may be selected from:

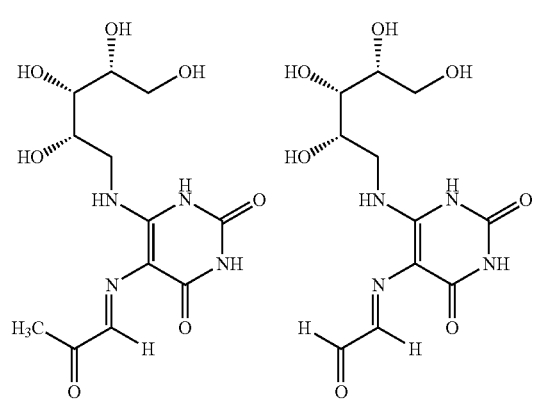

-continued

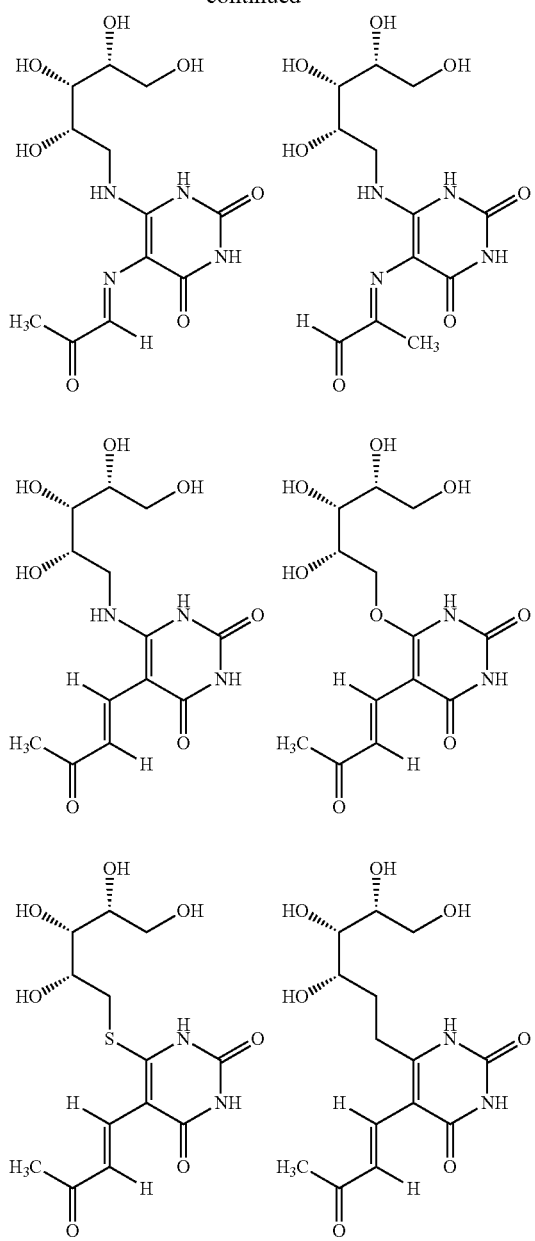

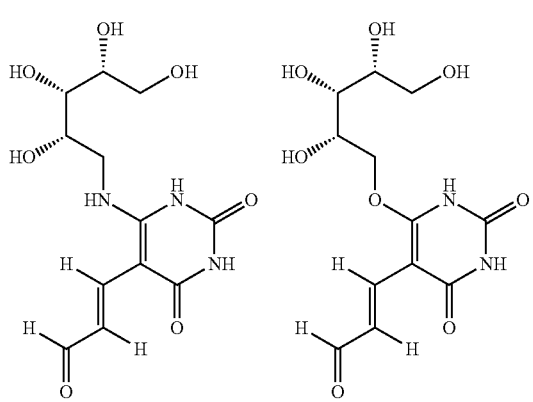

-continued

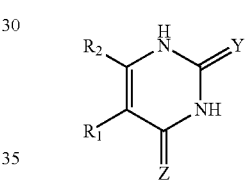

or a salt, solvate, tautomer, or stereoisomer thereof.

In another embodiment and with reference to the ligands of formula (I), the optional substituents include but are not limited to a group selected from the list consisting of halogen, oxo, thio, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —$NHC_1$-$C_4$alkyl, —$N(C_1$-$C_4$alkyl$)_2$, —$NHC_1$-$C_4$acyl, —NHC(O)$NH_2$, —NHC(O)NH$C_1$-$C_4$alkyl, —NHC(O)N($C_1$-$C_4$alkyl$)_2$, —NHC(S)$NH_2$, —NHC(S)$C_1$-$C_4$alkyl, —NHC(S)N($C_1$-$C_4$alkyl$)_2$, guanidino, —CN, —$NO_2$, mercapto, —S($O_2$)$NH_2$, —S($O_2$)NH$C_1$-$C_4$alkyl, $CO_2$H, CON$H_2$ and CONH$C_1$-$C_4$alkyl.

The [MR1-L] of the invention is preferably in an isolated or purified form.

The [MR1-L] can be in a multimeric form of the formula [MR1-L]$_n$, wherein the [MR1-L] subunit is represented up to n times, in a complex with a multi-valence binding molecule having a valency of n. In an embodiment, n is for 2 to 100, including 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100.

In one example, the multi-valence binding molecule is streptavadin with a valency of 4. In this instance, [MR1-L]$_n$ is defined as being 2, 3 or 4.

In an embodiment, [MR1-L]$_n$ is labeled with a reporter molecule or means to produce a detectable signal. This is represented as [MR1-L]$_n$*.

In another aspect, the present invention provides a compound represented by formula (I):

$$\text{(I)}$$

or a salt, solvate, tautomer, or stereoisomer thereof
wherein:
$R_1$ is selected from the group consisting of:
—X—C(O)—$R_1'$ (where $R_1'$ is H, or optionally substituted $C_1$-$C_6$alkyl, and X is independently a bond or a divalent linker selected from the group consisting of $C_1$-$C_3$ optionally substituted alkylene, —$NR_2'$— optionally substituted $C_1$-$C_3$alkylene-, —O— optionally substituted $C_1$-$C_3$alkylene-, —S— optionally substituted $C_1$-$C_3$alkylene-, —S(O)— optionally substituted $C_1$-$C_3$alkylene-, —N=$CR_2'$—, —$CR_2'$=$CR_2''$—, —$NR_2'$—C(O)—, —O—C(O)—, or —S—C(O) where each $R_2'$ and $R_2''$ is independently selected from H, halogen, CN, or optionally substituted $C_1$-$C_6$alkyl); —X'—C(O)$NR_3'R_4'$ (where $R_3'$ is H or optionally substituted $C_1$-$C_6$alkyl and $R_4'$ is optionally substituted $C_1$-$C_6$alkyl, OH, or CN or $R_3'R_4'$ together form an optionally substituted heterocyclyl or optionally substituted heteroaryl, and X' is independently a bond or a $C_1$-$C_3$ optionally substituted alkylene); —X''—C(O)O$R_5'$ (wherein $R_5'$ is H or optionally substituted $C_1$-$C_6$alkyl, and X'' is independently a bond or a $C_1$-$C_3$ optionally substituted alkylene); —X'''—C(O)NHSO$_2R_6'$ (wherein $R_6'$ is optionally substituted aryl, or optionally substituted $C_1$-$C_6$alkyl, and X''' is independently a bond or a $C_1$-$C_3$ optionally substituted alkylene); —X''''—S(O)$_2$NH$R_7'$ (wherein $R_7'$ is H, optionally substituted $C_1$-$C_6$alkyl, or optionally substituted aryl, and X'''' is independently a bond or a $C_1$-$C_3$ optionally substituted alkylene);

R₂ is selected from the group consisting of optionally substituted $C_{1-8}$alkyl, —NH(optionally substituted $C_{1-6}$alkyl), —N(optionally substituted $C_{1-6}$alkyl)(optionally substituted aryl), —N(optionally substituted $C_{1-6}$alkyl)₂, —O(optionally substituted $C_{1-6}$alkyl), —OC(O)($C_{1-6}$alkyl), —S(optionally substituted $C_{1-6}$alkyl), —SC(O)($C_{1-6}$alkyl), and —S(O)(optionally substituted $C_{1-6}$alkyl); and Y and Z are independently selected from the group consisting of oxo, thio, imino, mono-$C_{1-3}$alkylimino, mono-$C_{1-3}$acylimino, urea, mono-$C_{1-3}$alkylurea, thiourea, mono-$C_{1-3}$alkylthiourea, guanidine, mono-$C_{1-3}$alkylguanidino, and di-$C_{1-3}$alkylguanidino.

In an embodiment:

R₁ is —X—C(O)—R₁' (where R₁' is H, or optionally substituted $C_1$-$C_6$alkyl, and X is independently a divalent linker selected from the group consisting of $C_1$-$C_3$ optionally substituted alkylene, —NR₂'— optionally substituted $C_1$-$C_3$alkylene-, —O— optionally substituted $C_1$-$C_3$ alkylene-, —N=CR₂'—, —CR₂'=CR₂"—, —NR₂'—C(O)—, —OC(O)—, or —SC(O)— where each R₂' and R₂" is independently selected from H or optionally substituted $C_1$-$C_6$alkyl); and R₂ is selected from the group consisting of optionally substituted $C_{1-8}$alkyl, NH(optionally substituted $C_{1-6}$alkyl), —N(optionally substituted $C_{1-6}$allyl)(optionally substituted aryl), —N(optionally substituted $C_{1-6}$alkyl)₂, —O(optionally substituted $C_{1-6}$alkyl), —OC(O)($C_{1-6}$alkyl), —S(optionally substituted $C_{1-6}$alkyl), —SC(O)($C_{1-6}$alkyl), or —S(O)(optionally substituted $C_{1-6}$alkyl).

In an embodiment:

R₁ is —X—C(O)R₁' where R₁' is H or $C_{1-6}$alkyl and X is independently —NR₂'—CH₂—, —N=CR₂', —CR₂'=CR₂"—, —NR₂'—C(O)—, —OC(O)—, or —SC(O)— where R₂' and R₂" are independently H or $C_{1-6}$alkyl; and R₂ is —NH—$C_2$-$C_6$ alkyl optionally substituted 1 to 6 times with OH, OR₁', NH₂, NHR₁', NR₁'R₂', SH, or SR₁', where R₁' and R₂' are independently $C_{1-6}$alkyl, $C_{1-6}$acyl, $C_{1-6}$amido, or $C_{1-6}$thioamido.

In an embodiment:

R₁ is —N=CR₂'—C(O)R₁' or —CH=CR₂"—C(O)R₁', where each R₁' and R₂' is independently H or $C_{1-6}$alkyl; and R₂ is —NH—$C_2$-$C_6$ alkyl optionally substituted 1 to 4 times with OH.

In an embodiment, R₁' is H or $C_1$-$C_6$alkyl optionally substituted by a group selected from halogen, hydroxy, mercapto, amino, or amido.

In an embodiment both Y and Z are O.

In an embodiment Y is O and Z is S.

In an embodiment Y is S and Z is O.

In an embodiment Y is O and Z is imino.

In an embodiment Y is imino and Z is O.

In an embodiment Y is mono-$C_{1-3}$alkylimino and Z is O.

In an embodiment Y is O and Z is mono-$C_{1-3}$acylimino.

In an embodiment the ligand may be selected from:

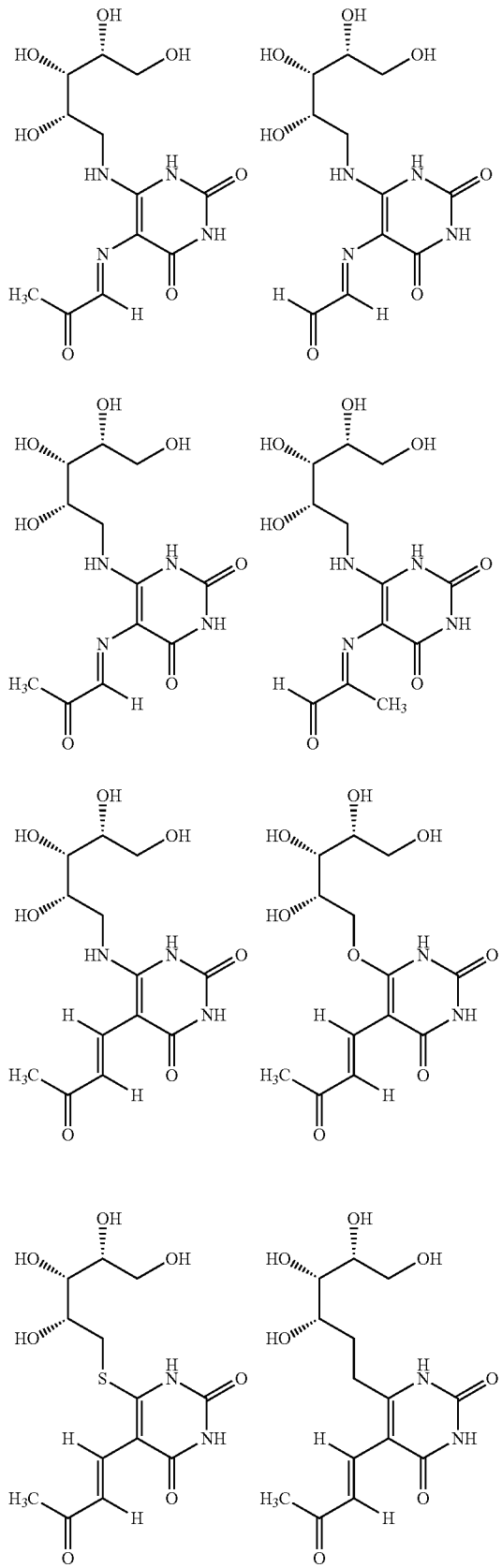

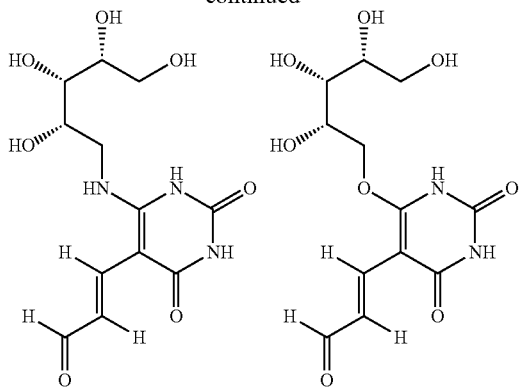
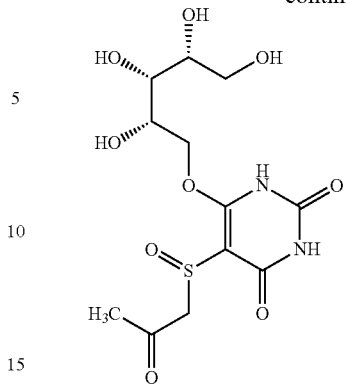
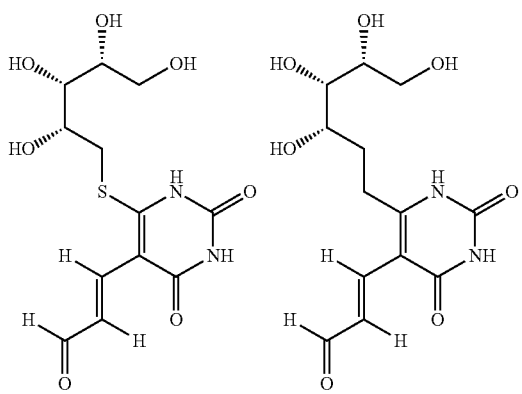
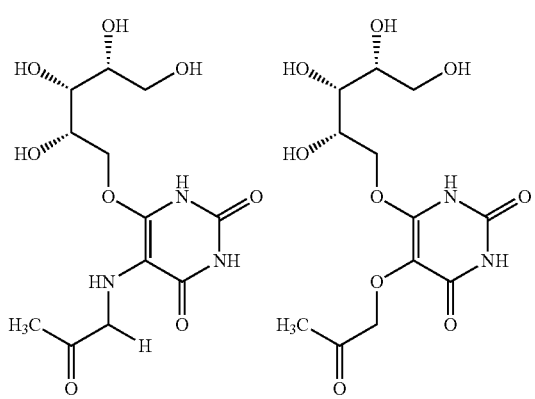
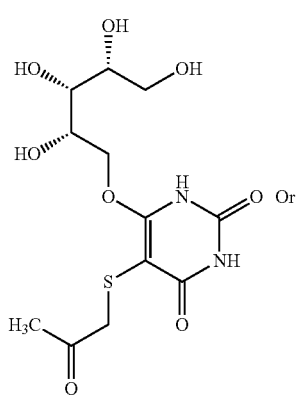

or a salt, solvate, tautomer, or stereoisomer thereof.

In an embodiment and with reference to the compounds of formula (I), the optional substituents include but are not limited to a group selected from the list consisting of halogen, oxo, thio, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —$NHC_1$-$C_4$alkyl, —$N(C_1$-$C_4$alkyl$)_2$, —$NHC_1$-$C_4$acyl, —NHC(O)$NH_2$, —NHC(O)$NHC_1$-$C_4$alkyl, —NHC(O)N($C_1$-$C_4$alkyl$)_2$, —NHC(S)$NH_2$, —NHC(S)$C_1$-$C_4$alkyl, —NHC(S)N($C_1$-$C_4$alkyl$)_2$, guanidino, —CN, —$NO_2$, mercapto, —S($O_2$)$NH_2$, —S($O_2$)$NHC_1$-$C_4$alkyl, $CO_2H$, $CONH_2$ and $CONHC_1$-$C_4$alkyl.

In a further aspect, the present invention provides use of the compound of formula (I) as hereinbefore defined to form [MR1-L] or [MR1-L]$_n$ that enable the purification, isolation, identification or characterization of MAIT cells and/or for diagnostic purposes.

In an embodiment, the compound is selected from 5-(2-oxoethylideneamino)-6-D-ribitylaminouracil (5-OE-RU) or 5-(2-oxopropylideneamino)-6-D-ribitylaminouracil (5-OP-RU) or a functional analog of any one thereof, including but not limited to oxidised and reduced forms thereof.

In an embodiment, the MR1 polypeptide comprises all or part of SEQ ID NO: 1 or SEQ ID NO: 4 or a functional derivative thereof having one or more amino acid substitutions, additions and/or deletions to SEQ ID NO: 1 or SEQ ID NO: 4, for example SEQ ID NO: 2 or SEQ ID NO: 5.

In an embodiment, the MR1 polypeptide comprises at least one mutation selected from the list consisting of K43A, K43M, K43I, K43L, K43F, K43Q, Y7A, Y7W, R9K, R9A, S24F, Y62A, L66A, L66F, W69A, R94K, R94A, I96A, I96F, W156A, using single letter abbreviations for amino acid residues. The number refers to the amino acid residue number in the wild-type MR1 amino acid sequence (SEQ ID NO: 1 or SEQ ID NO: 4).

In an embodiment the MR1 comprises one or more mutations in surface exposed groups including but not limited to the list consisting of D57, R61, L65, M72, V75, R79, T138, Q141, N146, H148, L151, N155, E158, and R167. The number refers to the amino acid residue number in the mature wild-type MR1 amino acid sequence (SEQ ID NO: 1 or SEQ ID NO: 4)

In an embodiment the MR1 comprises a K43A mutation.

In an embodiment, the present invention provides ligands and compounds useful for modulating MAIT cell activity. In an embodiment, the ligands and compounds of the present invention are provided as a composition comprising at least one riboflavin producing microorganism, for example, but not limited to *Salmonella* and *Helicobacter pylori*, a culture supernatant thereof, or a physiologically active substance derived from the microorganism, or a TLR agonist, wherein said riboflavin producing microorganism, a culture supernatant thereof, or a physiologically active substance derived from the microorganism, or TLR agonist modulates the activity of MAIT cells. In an embodiment, the composition of microorganisms is referred to as a probiotic. In an aspect, the present invention provides a method of detecting the presence of MAIT cells or MAIT cell activity in a biological sample from a subject, the method comprising the steps of a) contacting the biological sample with antigen presenting cells expressing [MR1-L] or [MR1-L]$_n$ or a soluble form thereof, under conditions that allow binding of the MR1 with MAIT cells present in the sample; and b) detecting the presence of MAIT cells or MAIT cell activity, wherein L is a compound represented by formula (I) as hereinbefore defined.

In another aspect, the present invention provides a method of detecting the presence of MAIT cells in a biological sample from a subject, the method comprising the steps of a) contacting the biological sample with any of the compounds, [MR1-L] or [MR1-L]$_n$ of the invention, under conditions that would allow binding of the compounds, [MR1-L] or [MR1-L]$_n$ to MAIT cell epitopes present in the sample; and b) detecting the presence of the bound compounds, [MR1-L] or [MR1-L]$_n$ in the biological sample.

In one embodiment, the compound, [MR1-L] or [MR1-L]$_n$ is conjugated or covalently bound to a detectable moiety.

In one embodiment of any of the aspects contemplated herein, the biological sample is a biological fluid, (for example serum, lymph, blood), cell sample or tissue sample (for example bone marrow or tissue biopsy, including mucosal tissue). In another embodiment, the mucosal tissue is gut, gut lamina propria, or lung. In another embodiment, the biological sample is taken from a patient, and the cells are purified for diagnostic purposes. In another embodiment, the biological sample is taken from a healthy individual.

In an embodiment, L is 5-(2-oxoethylideneamino)-6-D-ribitylaminouracil (5-OE-RU) or 5-(2-oxopropylideneamino)-6-D-ribitylaminouracil (5-OP-RU) or functional analog's thereof including but not limited to oxidized and reduced forms thereof.

Another aspect contemplated herein is a method of detecting the presence of MAIT cell activity in a subject, the method comprising the steps of a) administering antigen presenting cells expressing [MR1-L] or [MR1-L]$_n$ or a soluble form thereof, under conditions that allow binding of the MR1 with MAIT cells present in the subject; and b) detecting the presence of MAIT cell bound MR1 in the subject, wherein L is a compound represented by formula (I) as hereinbefore defined.

In an embodiment, L is 5-(2-oxoethylideneamino)-6-D-ribitylaminouracil (5-OE-RU) or 5-(2-oxopropylideneamino)-6-D-ribitylaminouracil (5-OP-RU) or functional analog's thereof including but not limited to oxidised and reduced forms thereof.

Another aspect contemplated herein is a method for preparing [MR1-L] said method comprising refolding [MR1] in the presence of compounds which facilitate the ligand bound in a ring-open conformation to residues with the MR1 amino acid sequence. In an embodiment, the compounds facilitate a Schiff base induced bond to an amino acid residue such as lysine (e.g. lysine 43 of human MR1 [SEQ ID NO:1], or lysine 43 of murine MR1 [SEQ ID NO: 2]. In an embodiment, the compound is 5-amino-6-D-ribitylaminouracil (5-A-RU) which together with small molecule metabolites form a ring-open conformation of the compound of formula (I) as herein defined, bound to Lysine 43 of human or murine MR1 via a Schiff base induced bond.

In an embodiment, the MR1-L subunit forms a hydrogen bond to Tyr95 of the MAIT TCR.

In an embodiment, the [MR1-L] is [MR1-5-OP-RU] or [MR1-5-OE-RU].

In an embodiment, the small molecule metabolites are glyoxal or methylglyoxal.

Another aspect contemplated herein involves the use of combinatorial chemistry employing the compound of Formula (I) as the scaffold basis for identification of further ligands for the purpose of blocking or activating MAIT cells or generating multimer MR1-ligand reagents. In an embodiment the compound is 5-(2-oxoethylideneamino)-6-D-ribitylaminouracil (5-OE-RU) or 5-(2-oxopropylideneamino)-6-D-ribitylaminouracil (5-OP-RU) or functional analog's thereof including but not limited to oxidised and reduced forms thereof.

In a further aspect, the present invention provides use of the compound of formula (I) as hereinbefore defined to form [MR1-L] or [MR1-L]$_n$ that modulate MAIT cell activity in vitro, ex vivo or in vivo.

In an embodiment, the compound is selected from 5-(2-oxoethylideneamino)-6-D-ribitylaminouracil (5-OE-RU) or 5-(2-oxopropylideneamino)-6-D-ribitylaminouracil (5-OP-RU) or prodrug or protected forms thereof.

In a further aspect, the present invention provides a pharmaceutical composition comprising the [MR1-L] subunit or [MR1-L]$_n$ as herein before defined together with one or more pharmaceutically acceptable carriers and/or diluents.

In another aspect, the present invention provides a pharmaceutical composition comprising the compound of formula (I) as herein before defined together with one or more pharmaceutically acceptable carriers and/or diluents. In an embodiment, the compound is 5-(2-oxoethylideneamino)-6-D-ribitylaminouracil (5-OE-RU) or 5-(2-oxopropylideneamino)-6-D-ribitylaminouracil (5-OP-RU) or functional analog's thereof including but not limited to oxidised and reduced forms thereof.

In a further aspect, the present invention provides a therapeutic pharmaceutical composition comprising the [MR1-L] subunit or [MR1-L]$_n$ as herein before defined together with one or more pharmaceutically acceptable carriers and/or diluents.

In another aspect, the present invention provides a therapeutic pharmaceutical composition comprising the compounds as herein before defined together with one or more pharmaceutically acceptable carriers and/or diluents. In an embodiment, the compound or ligand is 5-(2-oxoethylideneamino)-6-D-ribitylaminouracil (5-OE-RU) or 5-(2-oxopropylideneamino)-6-D-ribitylaminouracil (5-OP-RU) or prodrug or protected forms thereof.

In another aspect the present invention provides methods of regulating MAIT cell activity in vitro, ex vivo, or in vivo, comprising contacting MAIT cells with an effective amount of the compounds, [MR1-L] subunit or [MR1-L]$_n$ as herein before defined, or a pharmaceutical composition comprising same. In an embodiment, the methods comprise the administration of an effective amount of the compounds, [MR1-L] or [MR1-L]$_n$ as herein before defined, or a pharmaceutical composition comprising same, to a subject in need thereof for the treatment or prophylaxis of cancer, an infectious disease, an immune disease involving the mucosa such as autoimmune and inflammatory disorders, for example, but not limited to, cancer, an infectious disease, Crohn's Disease, ulcerative colitis, irritable bowel disease, chronic fatigue syndrome, oral infections, peptic ulceration, intestinal helminth or bacterial infection, ocular disease such as Trachoma, pelvic inflammatory disease, sexually transmitted diseases, Chlamydia infection, candidiasis and other fungal infections at epithelial and mucosal sites, tuberculosis, Celiac disease, rheumatoid arthritis and neuroinflammatory conditions, such as but not limited to Alzheimers disease (AD), multiple sclerosis (MS), amyotrophic lateral sclerosis (ALS), Parkinson's disease (PD), stroke, and variant Creuzfeldt-Jacob disease.

In an embodiment, the methods are directed at increasing, decreasing or inhibiting the activity of human MAIT cells, preferably ex vivo or in vivo, in a subject having a cancer, an infectious disease, an immune disease involving the mucosa, or an autoimmune or inflammatory disease such as but not limited to Crohn's Disease, ulcerative colitis, irritable bowel disease, chronic fatigue syndrome, oral infections, peptic ulceration, intestinal helminth or bacterial infection, ocular disease such as Trachoma, pelvic inflammatory disease, sexually transmitted diseases, Chlamydia infection, candidiasis and other fungal infections at epithelial and mucosal sites, tuberculosis, Celiac disease, rheumatoid arthritis and neuroinflammatory conditions, such as but not limited to Alzheimers disease (AD), multiple sclerosis (MS), amyotrophic lateral sclerosis (ALS), Parkinson's disease (PD), stroke, and variant Creuzfeldt-Jacob disease.

An aspect of the present invention provides a method of modulating MAIT cell activity, the method comprising contacting the cell with an effective amount of the compounds, [MR1-L] or [MR1-L]$_n$, or a pharmaceutical composition comprising same of the invention, for a time and under conditions sufficient to modulate MAIT cell activity, wherein the compound or ligand is a compound represented by formula (I) as hereinbefore defined. In an embodiment the compound or ligand is 5-(2-oxoethylideneamino)-6-D-ribitylaminouracil (5-OE-RU) or 5-(2-oxopropylideneamino)-6-D-ribitylaminouracil (5-OP-RU), which were either isolated or generated in situ by mixing 5-amino-6-D-ribitylaminouracil (5-A-RU) with glyoxal or methylglyoxal, respectively, or prodrug or protected forms thereof.

Another aspect of the present invention provides a method of modulating MAIT cell activity in a subject in need thereof, the method comprising administering to the subject an effective amount of the compounds, [MR1-L] or [MR1-L]$_n$ of the invention or a pharmaceutical composition comprising same of the invention, for a time and under conditions sufficient to modulate MAIT cell activity. In an embodiment, the compound or ligand is a compound represented by Formula (I) as herein defined. In an embodiment, the therapeutic compound or ligand is 5-(2-oxoethylideneamino)-6-D-ribitylaminouracil (5-OE-RU) or 5-(2-oxopropylideneamino)-6-D-ribitylaminouracil (5-OP-RU), which were either isolated or generated in situ by mixing 5-amino-6-D-ribitylaminouracil (5-A-RU) with glyoxal or methylglyoxal, respectively, or prodrug or protected forms thereof.

In a further aspect, the present invention provides a method for the treatment and/or prophylaxis of a condition characterized by excessive or insufficient MAIT cell activity in a subject, the method comprising administering to said subject an effective amount of the compounds, [MR1-L] or [MR1-L]$_n$ or a pharmaceutical composition comprising same, of the invention, for a time and under conditions sufficient to modulate MAIT cell activity. In an embodiment, the compound or ligand is a compound represented by Formula (I) as herein defined. In an embodiment, the compound or ligand is 5-(2-oxoethylideneamino)-6-D-ribitylaminouracil (5-OE-RU) or 5-(2-oxopropylideneamino)-6-D-ribitylaminouracil (5-OP-RU), which were either isolated or generated in situ by mixing 5-amino-6-D-ribitylaminouracil (5-A-RU) with glyoxal or methylglyoxal, respectively, or prodrug or protected forms thereof.

In an embodiment of any of the aspects contemplated herein, said modulation of MAIT cell activity is via MAIT cell TCRs. In an embodiment the MAIT cells are mammalian MAIT cells including human and rodent MAIT cells. In an embodiment, the modulation of MAIT cell activity is increasing, reducing or inhibiting MAIT cell activity. In one embodiment, said modulation is enhancement of the activity of the MAIT cells. In one embodiment, said modulation is inducement, of the proliferation of the MIT cells. In one embodiment, said modulation is inducement of the production of cytokines, such as TNF, RANTES, and/or IL-10 by MAIT cells, or the expression of CD69 on MAIT cells. In another embodiment, said modulation is the migration of MAIT cells to another organ or tissue leading to an increased accumulation of MAIT cells at this site. In yet another embodiment, said modulation is a reduction or inhibition of the activity of the MAIT cells. In one embodiment, said modulation is the depletion of MAIT cells.

In one embodiment, the subject is suffering from cancer. an infectious disease or amucosal immunological disorder such as an autoimmune or inflammatory disorder. In another embodiment, the disorder is selected from the group consisting of Crohn's Disease, ulcerative colitis, irritable bowel disease, chronic fatigue syndrome, oral infections, peptic ulceration, intestinal helminth or bacterial infection, ocular disease such as Trachoma, pelvic inflammatory disease, sexually transmitted diseases, Chlamydia infection, candidiasis and other fungal infections at epithelial and mucosal sites, tuberculosis, Celiac disease, rheumatoid arthritis and neuroinflammatory conditions, such as but not limited to Alzheimers disease (AD), multiple sclerosis (MS), amyotrophic lateral sclerosis (ALS), Parkinson's disease (PD), stroke, and variant Creuzfeldt-Jacob disease.

In another embodiment, the method further comprises the step of administering to the subject an appropriate additional therapeutic agent selected from the group consisting of an immunomodulatory agent, a hormonal agent, a chemotherapeutic agent, an anti-angiogenic agent, an apoptotic agent, an antibody that binds to and modulates a receptor present on MAIT cells, an anti-infective agent, a targeting agent, an anti-inflammation drug, a steroid, an immune system suppressor, an antibiotic, an anti-diarrheal drug, and an adjunct compound.

In a further embodiment, the compounds are administered in combination with other compounds such as TLR agonists or riboflavin producing microorganisms, for example *Salmonella* and *Helicobacter pylori*.

In another aspect, the invention provides a method for identifying a ligand that is efficacious in the treatment of a disease or disorder by administering the compounds, [MR1-L] or [MR1-L]$_n$ of the invention to a non-human primate model of the disorder and assessing the ability of the therapeutic compounds, [MR1-L] or [MR1-L]$_n$ to prevent or ameliorate the disorder, or a symptom thereof, or to modulate the activity of MAIT cells in the primate.

In another aspect, the present invention provides the use of the compounds, [MR1-L] or [MR1-L]$_n$ as herein before defined in the manufacture of a medicament for the treatment of a disease or disorder in a subject, wherein the compounds, [MR1-L] or [MR1-L]$_n$ modulates the level of activity of MAIT cells.

In an embodiment of any of the aspects contemplated herein, the MR1 polypeptide comprises all or part of SEQ ID NO: 1 or SEQ ID NO: 4 or a functional derivative thereof having one or more amino acid substitutions, additions and/or deletions to SEQ ID NO: 1 or SEQ ID NO: 4, for example SEQ ID NO: 2 or SEQ ID NO: 5.

In an embodiment, the MR1 polypeptide comprises at least one mutation selected from the list consisting of K43A, K43M, K43I, K43L, K43F, K43Q, Y7A, Y7W, R9K, R9A, S24F, Y62A, L66A, L66F, W69A, R94K, R94A, I96A, I96F, W156A, using single letter abbreviations for amino acid residues. The number refers to the amino acid residue number in the wild-type MR1 amino acid sequence (SEQ ID NO: 1 or SEQ ID NO: 4).

In an embodiment the MR1 comprises one or more mutations in surface exposed groups including but not limited to the list consisting of D57, R61, L65, M72, V75, R79, T138, Q141, N146, H148, L151, N155, E158, and R167. The number refers to the amino acid residue number in the mature wild-type MR1 amino acid sequence (SEQ ID NO: 1 or SEQ ID NO: 4)

In an embodiment the MR1 comprises a K43A mutation.

Another aspect contemplated herein involves the use of combinatorial chemistry employing the compound of Formula (I) as the scaffold basis for identification of further ligands for the purpose of modulating MAIT cell activity. In an embodiment the compound is 5-(2-oxoethylideneamino)-6-D-ribitylaminouracil (5-OE-RU) or 5-(2-oxopropylideneamino)-6-D-ribitylaminouracil (5-OP-RU) or prodrug or protected forms thereof.

In another aspect contemplated herein the ligands or functional analogs thereof, compounds or compositions described herein can be included in kits, for example for use as diagnostic reagents for detecting the presence of MAIT cells and/or as therapeutic reagents for modulating the activity of MAIT cells.

In an embodiment the MR1 comprises a K43A mutation.

Another aspect contemplated herein involves the use of combinatorial chemistry employing the compound of Formula (I) as the scaffold basis for identification of further ligands for the purpose of modulating MAIT cell activity. In an embodiment the compound is 5-(2-oxoethylideneamino)-6-D-ribitylaminouracil (5-OE-RU) or 5-(2-oxopropylideneamino)-6-D-ribitylaminouracil (5-OP-RU) or prodrug or protected forms thereof.

In another aspect contemplated herein the ligands or functional analogs thereof, compounds or compositions described herein can be included in kits, for example for use as diagnostic reagents for detecting the presence of MAIT cells and/or as therapeutic reagents for modulating the activity of MAIT cells.

BRIEF DESCRIPTION OF THE DRAWINGS

FIG. 6 is a schematic showing NMR characterization of 5-OP-RU (3d) in DMSO-$d_6$ with internal solvent peak at 2.50 ppm and 39.52 ppm for $^1$H and $^{13}$C, respectively. (a) $^1$H NMR (600 MHz); (b) $^{13}$C NMR (150 MHz); (c) Heteronuclear Single Quantum Correlation (HSQC). The compound 5-OP-RU (3d) was synthesised from the reaction of 5-A-RU and methylglyoxal in DMSO-$d_6$, and then isolated from aqueous media by rpHPLC. Although it was less stable in water, it could still be identified and characterised at pH>6.

FIG. 13 is a table showing data collection and refinement statistics:
[1] $R_{p.i.m}=\Sigma_{hkl}[1/(N-1)]^{1/2} \Sigma_i|I_{hkl,i}-<I_{hkl}>|/\Sigma_{hkl}<I_{hkl}>$
[2] $R_{factor}=(\Sigma||F_o|-|F_c||)/(\Sigma|F_o|)$—for all data except as indicated in footnote 3.
[3] 5% of data was used for the $R_{free}$ calculation
Values in parentheses refer to the highest resolution bin.

FIG. 14 is a schematic showing greater numbers of stomach MAIT cells in Helicobacter positive individuals. A) MAIT cell detection in paraffin sections of human gastric tissue. Serial sections were stained with Ab to CD3, TRAV1-2 or isotype control. B) Immunofluorescent staining of human duodenal biopsy showing co-staining with TRAV1-2 mAb "D5" and CD3. C) Correlation between MAIT cell infiltrate and Helicobacter infection in human gastric biopsies. Paraffin-embedded biopsy sections were stained with anti-TRAV1-2 and CD3 for MAIT enumeration (unpaired Student's t test).

FIG. 21 is a schematic showing pre-priming boosts the MAIT response to infection. MAIT cells (TCRβ$^+$Tetramer$^+$) were detected from stomachs of mice infected with *H. pylori* with/out pre-priming (with *S. Typhimurium* intranasally, 7 wk). Subsequent *H. pylori* infection was effective in enhancing MAIT % in all mice. MR1$^{-/-}$ controls show no MAIT cells.

FIG. 24 is a graph showing preferential expansion of CD8$^+$ MAIT cells upon infection with *S. Typhimurium* BRD509. Uninfected or infected mice (10$^6$ *S. Typhimurium* BRD509 i.n.) were killed for examination of MAIT cells. A) Gating strategy for CD4 and CD8 staining of cells isolated from the lungs of mice. CD8$^+$ MAIT cells are expressed as a percentage of total MAIT cells in the lungs from uninfected or infected mice from B) day 7 post infection, and C) over the time of infection course. Data represent Mean+/−SEM from 5 mice per group. The experiment was performed three times with similar results.

DETAILED DESCRIPTION OF THE INVENTION

Figure 1:
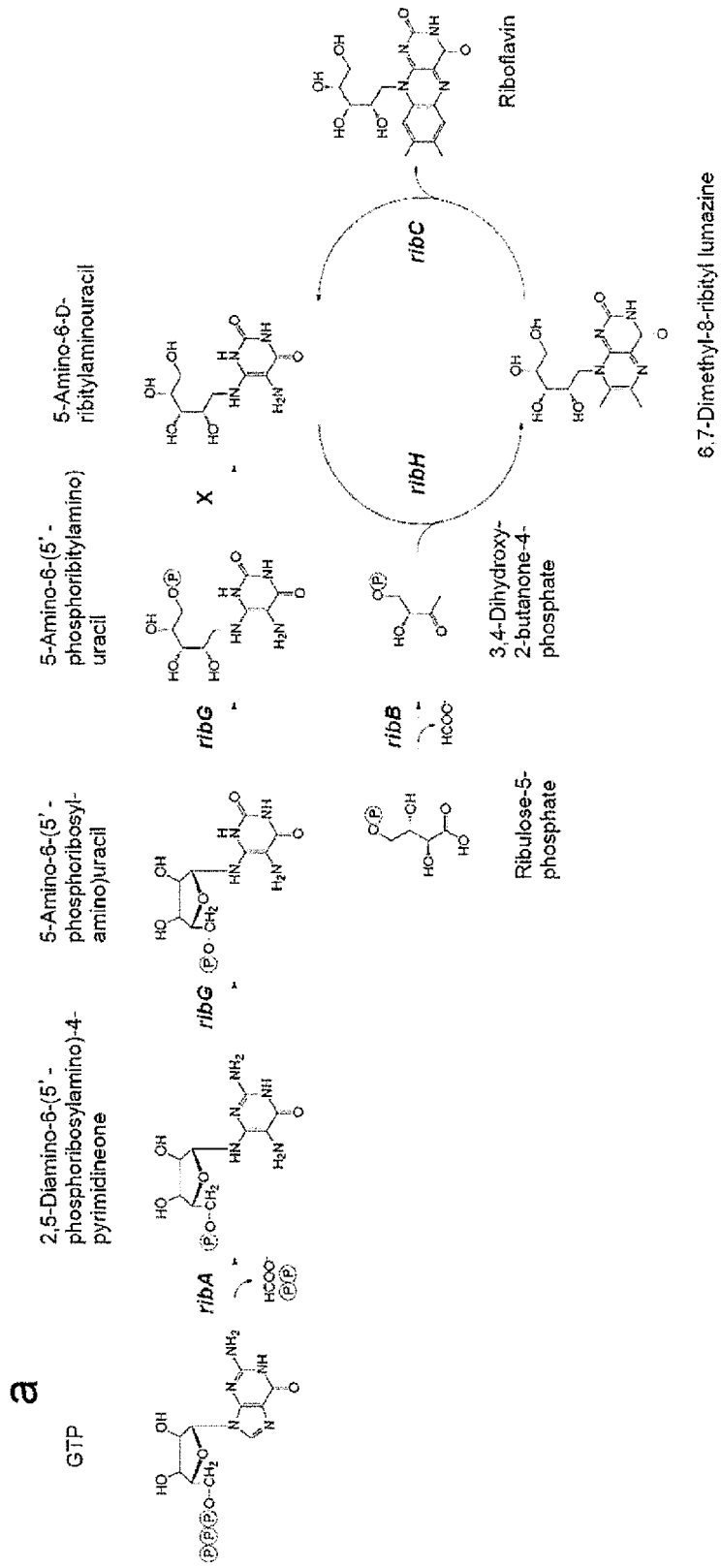
FIG. 1 is a schematic showing the riboflavin pathway furnishes ligands that activate MAIT cells (a) Riboflavin biosynthesis pathway. RibH; lumazine synthase. X; hypothetical phosphatase. (b) Cells were incubated overnight with filtered S/N from *L. lactis* NZ9000 (wt), ribA− (ribA deletion mutation), CB013 and CB021 (riboflavin overproducers) overnight cultures+/−3 g/ml riboflavin then stained for CD3-PE and anti-CD69-APC. MFI CD69-APC for gated Jurkat.MAIT cells, mean+/−SEM. (c) Cells were incubated overnight with 10 1 filtered, culture S/N from *Lactococcus* CB013 (deregulated riboflavin operon), CB013ΔRibA, CB013ΔRibB, CB013ΔRibG and CB013ΔRibH or *S. typhimurium*, then stained for CD3-PE and CD69-APC. MFI CD69-APC for gated Jurkat.MAIT cells, mean+/−SEM. Experiments performed at least 3 times.
Figure 1:
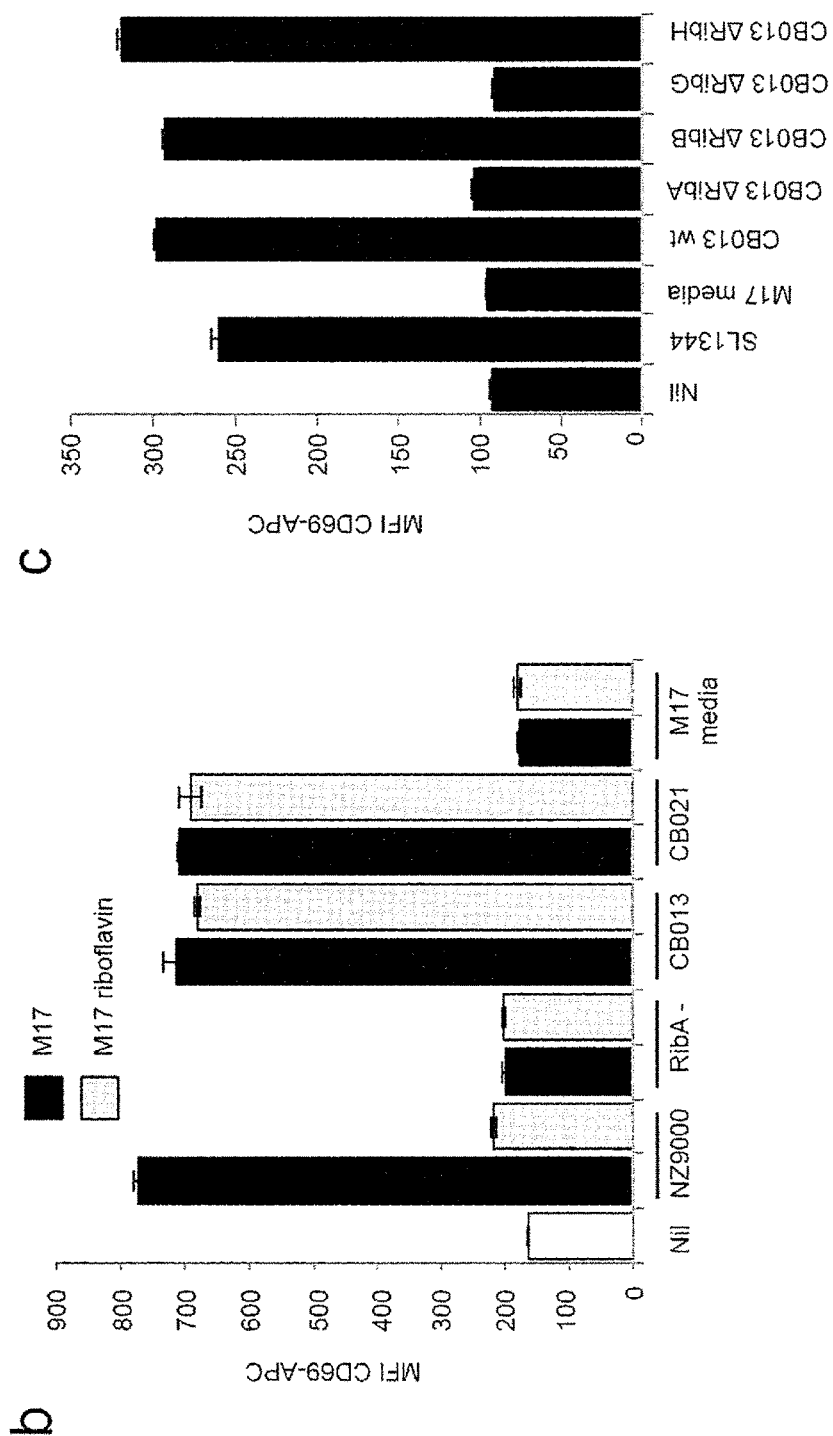

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the singular forms "a", "an" and "the" include plural aspects unless the context clearly dictates otherwise. Thus, for example, reference to "a cell" includes a single cell, as well as two or more cells; "an agent" including a single or two or more agents; "the invention" including single or multiple aspects of an invention; and so forth.

The present invention is based on experiments described herein that demonstrate that potent MR1 MAIT-cell activating antigens are formed via interaction of 5-amino-6-D-ribitylaminouracil (5-A-RU), an early intermediate in bacterial riboflavin synthesis, with small molecules which are derived from other metabolic pathways.

Accordingly, immunological reagents are provided that are a result of the re-folding of MR1 in the presence of a ligand to form MR1-L in subunit [MR1-L] or multimeric [MR1-L]$_n$ form. The subunit or multimeric MR1-ligand complexes bind the surface of MAIT cells and are useful for detection, numeration, characterization and isolation of MAIT cells for research and diagnostic purposes, and further are useful for the modulation of MAIT cell activity and in particular the treatment or prophylaxis of diseases or disorders associated with aberrant MAIT cell activity.

Also provided are ligands and compounds useful for modulating MAIT cell activity.

In an aspect, the present invention provides [MR1-L], wherein the ligand is represented by formula (I):

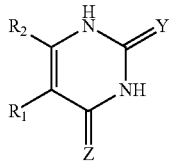

or a salt, solvate, tautomer, or stereoisomer thereof wherein:

$R_1$ is selected from the group consisting of:
—X—C(O)—$R_1'$ (where $R_1'$ is H, or optionally substituted $C_1$-$C_6$alkyl, and X is independently a bond or a divalent linker selected from the group consisting of $C_1$-$C_3$ optionally substituted alkylene, —$NR_2'$— optionally substituted $C_1$-$C_3$alkylene-, —O— optionally substituted $C_1$-$C_3$alkylene-, —S— optionally substituted $C_1$-$C_3$alkylene-, —S(O)— optionally substituted $C_1$-$C_3$alkylene-, —N=$CR_2'$—, —$CR_2'$=$CR_2''$—, —$NR_2'$—C(O)—, —O—C(O)—, or —S—C(O)— where each $R_2'$ and $R_2''$ is independently selected from H, halogen, CN, or optionally substituted $C_1$-$C_6$alkyl); —X'—C(O)$NR_3'R_4'$ (where $R_3'$ is H or optionally substituted $C_1$-$C_6$alkyl and $R_4'$ is optionally substituted $C_1$-$C_6$alkyl, OH, or CN or $R_3'R_4'$ together form an optionally substituted heterocyclyl or optionally substituted heteroaryl, and X' is independently a bond or a $C_1$-$C_3$ optionally substituted alkylene); —X''—C(O)$OR_5'$ (wherein $R_5'$ is H or optionally substituted $C_1$-$C_6$alkyl, and X'' is independently a bond or a $C_1$-$C_3$ optionally substituted alkylene); —X'''—C(O)$NHSO_2R_6'$ (wherein $R_6'$ is optionally substituted aryl, or optionally substituted $C_1$-$C_6$alkyl, and X''' is independently a bond or a $C_1$-$C_3$ optionally substituted alkylene); and —X''''—S(O)$_2NHR_7'$ (wherein $R_7'$ is H, optionally substituted $C_1$-$C_6$alkyl, or optionally substituted aryl, and X'''' is independently a bond or a $C_1$-$C_3$ optionally substituted alkylene);

$R_2$ is selected from the group consisting of optionally substituted $C_{1-8}$alkyl, —NH(optionally substituted $C_{1-6}$alkyl), —N(optionally substituted $C_{1-6}$alkyl)(optionally substituted aryl), —N(optionally substituted $C_{1-6}$alkyl)$_2$, —O(optionally substituted $C_{1-6}$alkyl), —OC(O)($C_{1-6}$alkyl), —S(optionally substituted $C_{1-6}$alkyl), —SC(O)($C_{1-6}$alkyl), and —S(O)(optionally substituted $C_{1-6}$alkyl); and Y and Z are independently selected from the group consisting of oxo, thio, imino, mono-$C_{1-3}$ alkylimino, mono-$C_{1-3}$ acylimino, urea, mono-$C_{1-3}$ alkylurea, thiourea, mono-$C_{1-3}$alkylthiourea, guanidine, mono-$C_{1-3}$ alkylguanidino, and di-$C_{1-3}$alkylguanidino.

In an embodiment:
$R_1$ is —X—C(O)—$R_1'$ (where $R_1'$ is H, or optionally substituted $C_1$-$C_6$alkyl, and X is independently a divalent linker selected from the group consisting of $C_1$-$C_3$ optionally substituted alkylene, —$NR_2'$— optionally substituted $C_1$-$C_3$alkylene-, —O— optionally substituted $C_1$-$C_3$alkylene-, —N=$CR_2'$—, —$CR_2'$=$CR_2''$—, —$NR_2'$—C(O)—, —C(O)—, or —SC(O)— where each $R_2'$ and $R_2''$ is independently selected from H or optionally substituted $C_1$-$C_6$alkyl); and $R_2$ is selected from the group consisting of optionally substituted $C_{1-8}$alkyl, NH(optionally substituted $C_{1-6}$alkyl), —N(optionally substituted $C_{1-6}$allyl)(optionally substituted aryl), —N(optionally substituted $C_{1-6}$alkyl)$_2$, —O(optionally substituted $C_{1-6}$alkyl), —OC(O)($C_{1-6}$alkyl), —S(optionally substituted $C_{1-6}$alkyl), —SC(O)($C_{1-6}$alkyl), or —S(O)(optionally substituted $C_{1-6}$alkyl).

In an embodiment:
$R_1$ is —X—C(O)$R_1'$ where $R_1'$ is H or $C_{1-6}$alkyl and X is independently —$NR_2'$—$CH_2$—, —N=$CR_2'$—, —$CR_2'$=$CR_2''$—, —$NR_2'$—C(O)—, —OC(O)—, or —SC(O)— where $R_2'$ and $R_2''$ are independently H or $C_{1-6}$alkyl; and $R_2$ is —NH—$C_2$-$C_6$ alkyl optionally substituted 1 to 6 times with OH, $OR_1'$, $NH_2$, $NHR_1'$, $NR_1'R_2'$, SH, or $SR_1'$, where $R_1'$ and $R_2'$ are independently $C_{1-6}$alkyl, $C_{1-6}$acyl, $C_{1-6}$amido, or $C_{1-6}$thioamido.

In an embodiment:
$R_1$ is —N=$CR_2'$—C(O)$R_1'$ or —CH=$CR_2''$—C(O)$R_1'$, where each $R_1'$ and $R_2'$ is independently H or $C_{1-6}$alkyl; and $R_2$ is —NH—$C_2$-$C_6$ alkyl optionally substituted 1 to 4 times with OH.

In an embodiment, $R_1'$ is H or $C_1$-$C_6$alkyl optionally substituted by a group selected from halogen, hydroxy, mercapto or amino.

In an embodiment both Y and Z are O.

In an embodiment Y is O and Z is S.

In an embodiment Y is S and Z is O.

In an embodiment Y is O and Z is imino.

In an embodiment Y is mono-$C_{1-3}$alkylimino and Z is O.

In an embodiment Y is O and Z is mono-$C_{1-3}$acylimino.

In an embodiment the ligand may be selected from:

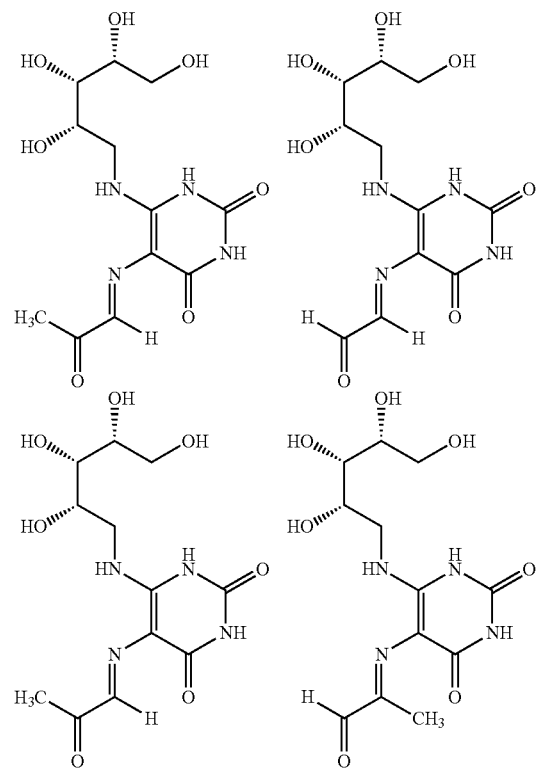

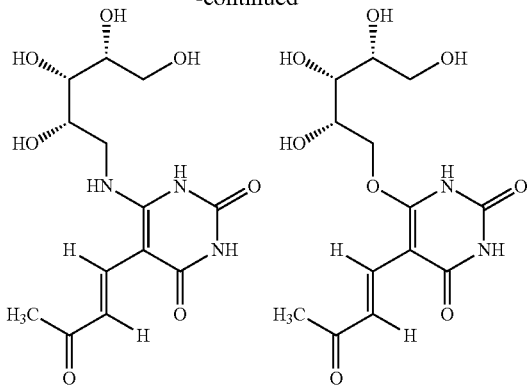
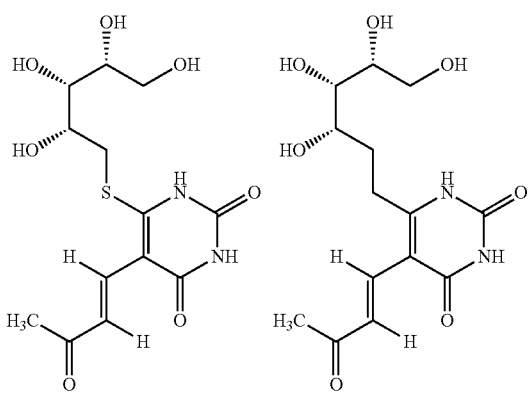
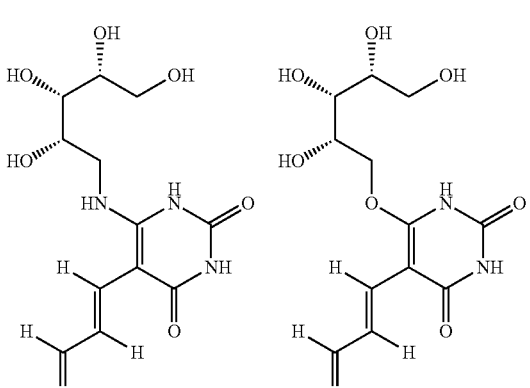
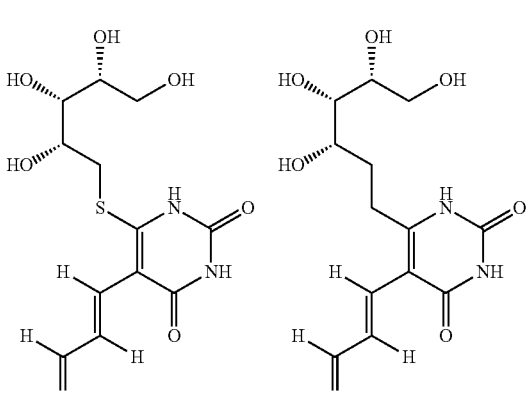
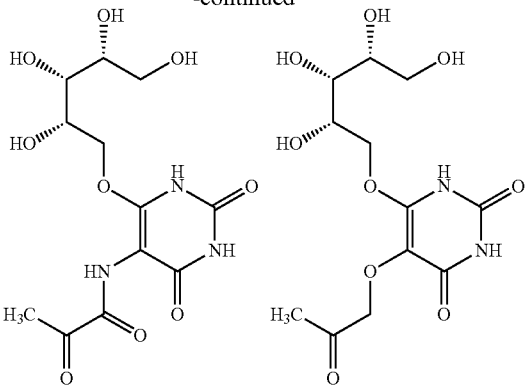
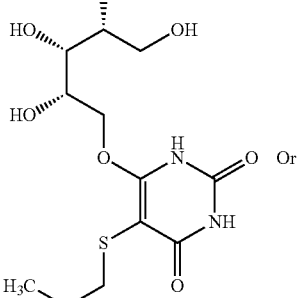
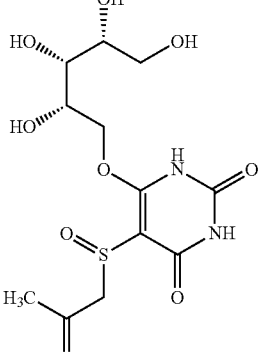

or a salt, solvate, tautomer, or stereoisomer thereof.

With reference to formula (I), the optional substituents include but are not limited to a group selected from the list consisting of halogen, oxo, thio, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —$NHC_1$-$C_4$alkyl, —$N(C_1$-$C_4$alkyl$)_2$, —$NHC_1$-$C_4$acyl, —NHC(O)$NH_2$, —NHC(O)$NHC_1$-$C_4$alkyl, —NHC(O)$N(C_1$-$C_4$alkyl$)_2$, —NHC(S)$NH_2$, —NHC(S)$C_1$-$C_4$alkyl, —NHC(S)N($C_1$-$C_4$alkyl$)_2$, guanidino, —CN, —$NO_2$, mercapto, —S($O_2$)$NH_2$, —S($O_2$)$NHC_1$-$C_4$alkyl, $CO_2H$, $CO_2NH_2$ and $CO_2NHC_1$-$C_4$alkyl.

In an embodiment, the [MR1] used to prepare the [MR1-L] of the invention is isolated. The term "isolated" [MR1] refers to [MR1] which has been substantially purified from a host cell. Conventional purification methods known to skilled artisans may be used to obtain isolated [MR1]. The term also includes recombinant [MR1] and chemically synthesized [MR1].

In an embodiment the [MR1-L] is collected in an isolated form, which means being substantially chemical-free, for example, contains 10 percent by weight or less of a total of any solvents, chemical(s) or media used in a preparation thereof and the [MR1-L] being at least 70% by weight of the isolated form. In an embodiment, the [MR1-L] is collected and purified in an isolated and purified form, i.e., the [MR1-L] being substantially chemical-free and comprising at least 80% by weight, more preferably at least 90% by weight, of the purified form. The [MR1-L] can be purified by known techniques, including, for example, chromatography on ion exchange materials, separation by size, immunoaffinity chromatography and electrophoresis.

In another aspect, the present invention provides a compound represented by formula (I):

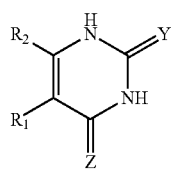

(I)

or a salt, solvate, tautomer, or stereoisomer thereof wherein:
  $R_1$ is selected from the group consisting of:
    —X—C(O)—$R_1'$ (where $R_1'$ is H, or optionally substituted $C_1$-$C_6$alkyl, and X is independently a bond or a divalent linker selected from the group consisting of $C_1$-$C_3$ optionally substituted alkylene, —$NR_2'$— optionally substituted $C_1$-$C_3$alkylene-, —O— optionally substituted $C_1$-$C_3$alkylene-, —S— optionally substituted $C_1$-$C_3$alkylene-, —S(O)— optionally substituted $C_1$-$C_3$alkylene-, —N=$CR_2'$—, —$CR_2'$=$CR_2''$—, —$NR_2'$—C(O)—, —O—C(O)—, or —S—C(O)— where each $R_2'$ and $R_2''$ is independently selected from H, halogen, CN, or optionally substituted $C_1$-$C_6$alkyl); —X'—C(O)$NR_3'R_4'$ (where $R_3'$ is H or optionally substituted $C_1$-$C_6$alkyl and $R_4'$ is optionally substituted $C_1$-$C_6$alkyl, OH, or CN or $R_3'R_4'$ together form an optionally substituted heterocyclyl or optionally substituted heteroaryl, and X' is independently a bond or a $C_1$-$C_3$ optionally substituted alkylene); —X''—C(O)$OR_5'$ (wherein $R_5'$ is H or optionally substituted $C_1$-$C_6$alkyl, and X'' is independently a bond or a $C_1$-$C_3$ optionally substituted alkylene); —X'''—C(O)$NHSO_2R_6'$ (wherein $R_6'$ is optionally substituted aryl, or optionally substituted $C_1$-$C_6$alkyl, and X''' is independently a bond or a $C_1$-$C_3$ optionally substituted alkylene); —X''''—S(O)$_2NHR_7'$ (wherein $R_7'$ is H, optionally substituted $C_1$-$C_6$alkyl, or optionally substituted aryl, and X'''' is independently a bond or a $C_1$-$C_3$ optionally substituted alkylene);
  $R_2$ is selected from the group consisting of optionally substituted $C_{1-8}$alkyl, —NH(optionally substituted $C_{1-6}$alkyl), —N(optionally substituted $C_{1-6}$alkyl)(optionally substituted aryl), —N(optionally substituted $C_{1-6}$alkyl)$_2$, —O(optionally substituted $C_{1-6}$alkyl), —OC(O)($C_{1-6}$alkyl),—S(optionally substituted $C_{1-6}$alkyl), —SC(O)($C_{1-6}$alkyl), and —S(O)(optionally substituted $C_{1-6}$alkyl)
  Y and Z are independently selected from the group consisting of oxo, thio, imino, mono-$C_{1-3}$ alkylimino, mono-$C_{1-3}$ acylimino, urea, mono-$C_{1-3}$ alkylurea, thiourea, mono-$C_{1-3}$alkylthiourea, guanidine, mono-$C_{1-3}$ alkylguanidino, and di-$C_{1-3}$ alkylguanidino.

In an embodiment:
  $R_1$ is —X—C(O)—$R_1'$ (where $R_1'$ is H, or optionally substituted $C_1$-$C_6$alkyl, and X is independently a divalent linker selected from the group consisting of $C_1$-$C_3$ optionally substituted alkylene, —$NR_2'$— optionally substituted $C_1$-$C_3$alkylene-, —O— optionally substituted $C_1$-$C_3$alkylene-, —N=$CR_2'$—, —$CR_2'$=$CR_2''$—, —$NR_2'$—C(O)—, —OC(O)—, or —SC(O)— where each $R_2'$ and $R_2''$ is independently selected from H or optionally substituted $C_1$-$C_6$alkyl); and
  $R_2$ is selected from the group consisting of optionally substituted $C_{1-8}$alkyl, NH(optionally substituted $C_{1-6}$alkyl), —N(optionally substituted $C_{1-6}$allyl)(optionally substituted aryl), —N(optionally substituted $C_{1-6}$alkyl)$_2$, —O(optionally substituted $C_{1-6}$alkyl), —OC(O)($C_{1-6}$alkyl), —S(optionally substituted $C_{1-6}$alkyl), —SC(O)($C_{1-6}$alkyl), or —S(O)(optionally substituted $C_{1-6}$alkyl).

In an embodiment:
  $R_1$ is —X—C(O)$R_1'$ where $R_1'$ is H or $C_{1-6}$alkyl and X is independently —$NR_2'$—$CH_2$—, —N=$CR_2'$—, —$CR_2'$=$CR_2''$—, —$NR_2'$—C(O)—, —OC(O)—, or —SC(O)— where $R_2'$ and $R_2''$ are independently H or $C_{1-6}$alkyl; and
  $R_2$ is —NH—$C_2$-$C_6$ alkyl optionally substituted 1 to 6 times with OH, $OR_1'$, $NH_2$, $NHR_1'$, $NR_1'R_2'$, SH, or $SR_1'$, where $R_1'$ and $R_2'$ are independently $C_{1-6}$alkyl, $C_{1-6}$acyl, $C_{1-6}$amido, or $C_{1-6}$thioamido.

In an embodiment:
  $R_1$ is —N=$CR_2'$—C(O)$R_1'$ or —CH=$CR_2''$—C(O)$R_1'$, where each $R_1'$ and $R_2'$ is independently H or $C_{1-6}$alkyl; and
  $R_2$ is —NH—$C_2$-$C_6$ alkyl optionally substituted 1 to 4 times with OH.

In an embodiment, $R_1'$ is H or $C_1$-$C_6$alkyl optionally substituted by a group selected from halogen, hydroxy, mercapto or amino.

In an embodiment both Y and Z are O.
In an embodiment Y is O and Z is S.
In an embodiment Y is S and Z is O.
In an embodiment Y is O and Z is imino.
In an embodiment Y is imino and Z is O.
In an embodiment Y is mono-$C_{1-3}$alkylimino and Z is O.
In an embodiment Y is O and Z is mono-$C_{1-3}$acylimino.
In an embodiment the ligand may be selected from:

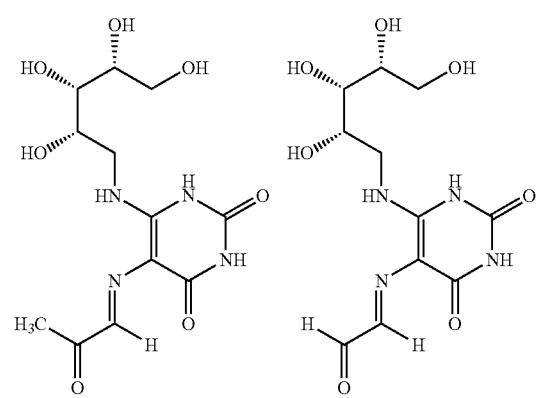

-continued

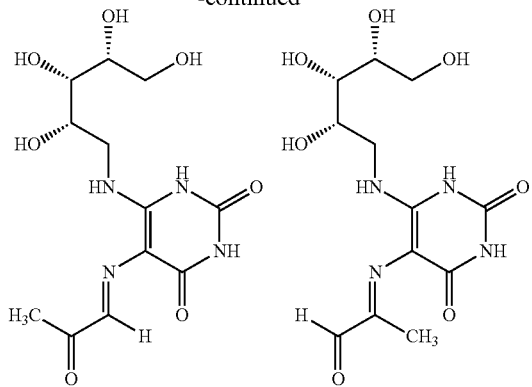
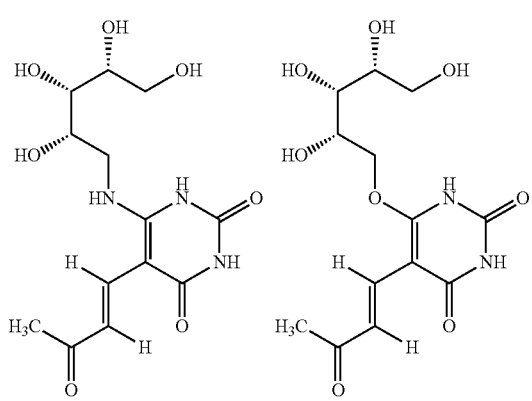
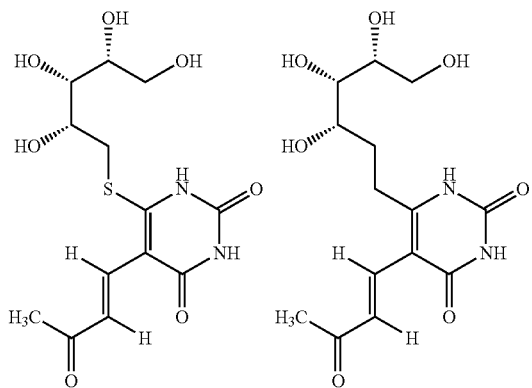
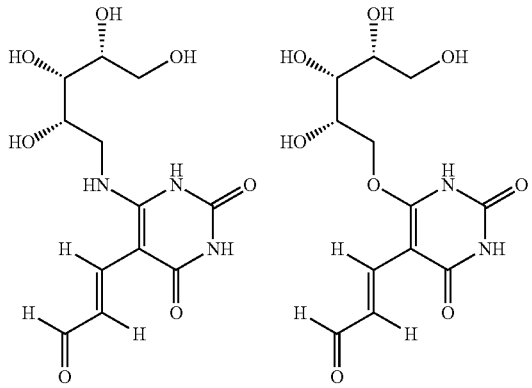

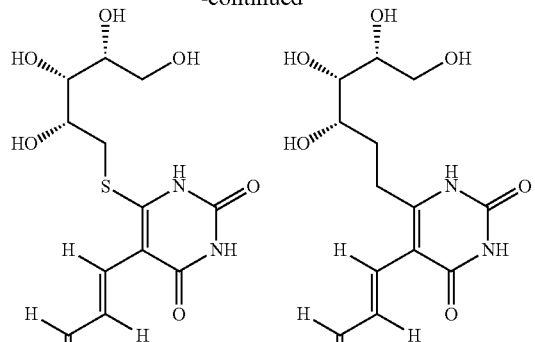
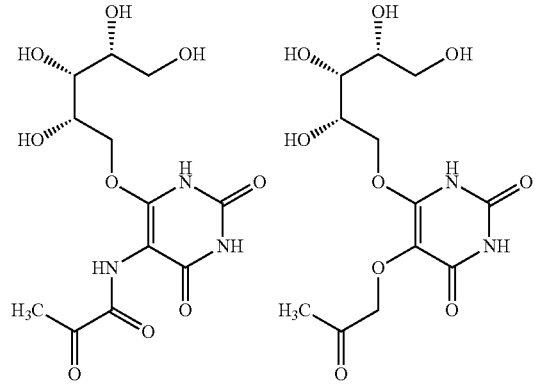
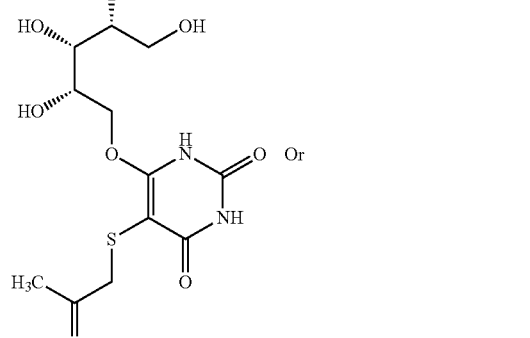
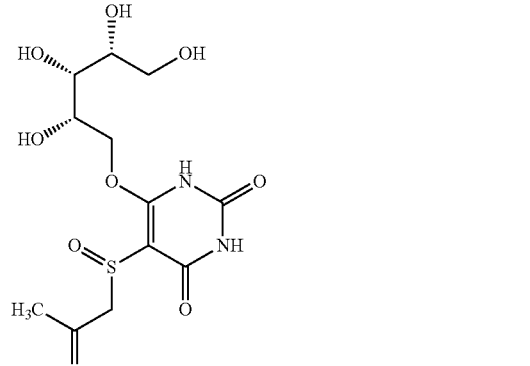

or a salt, solvate, tautomer, or stereoisomer thereof.

With reference to formula (I), the optional substituents include but are not limited to a group selected from the list consisting of halogen, oxo, thio, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —$NHC_1$-$C_4$alkyl, —$N(C_1$-$C_4$alkyl$)_2$, —$NHC_1$-$C_4$acyl, —NHC(O)

NH$_2$, —NHC(O)NHC$_1$-C$_4$alkyl, —NHC(O)N(C$_1$-C$_4$alkyl)$_2$, —NHC(S)NH$_2$, —NHC(S)C$_1$-C$_4$alkyl, —NHC(S)N(C$_1$-C$_4$alkyl)$_2$, guanidino, —CN, —NO$_2$, mercapto, —S(O$_2$)NH$_2$, —S(O$_2$)NHC$_1$-C$_4$alkyl, CO$_2$H, CO$_2$NH$_2$ and CO$_2$NHC$_1$-C$_4$alkyl.

The present inventors have shown that tetramers produced from mouse MR1 are capable of staining human and mouse peripheral blood mononuclear cells (PBMCs). Accordingly, within the context of the invention, the term MR1 refers to a mammalian MR1 polypeptide. In an embodiment the MR1 polypeptide is human, primate or mouse MR1 polypeptide. In an embodiment the MR1 is from a mouse or a human.

Accordingly, in an embodiment, the [MR1-L] subunit is complexed in a multimeric form [MR1-L]$_n$ wherein n is from 2 to about 100 including 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100. In an embodiment, the multimeric complex of [MR1-L] subunit is facilitated in a multi-valence binding molecule wherein the valency of the binding molecule is n and the multimeric structure comprises up to n MR1-ligand subunits.

In an embodiment, the multivalent binding molecule is streptavidin, having a valency of 4. In an embodiment, [MR1-L]$_n$ is labeled so as to produce, or has means to produce, a detection signal. Such a complex is referred to herein as [MR1-L]$_n$*.

The ability of the [MR1-L] of the invention to bind to mammalian MAIT cells and/or either promote, or inhibit MAIT cell activation, makes them useful for numerous applications, for example, purifying mammalian and more particularly human or other primate MAIT cells via MR1-ligand tetramers, or specifically labeling mammalian and more particularly human or other primate MAIT cells in vitro, in vivo, or ex vivo. It will be appreciated that the ability to specifically purify and label MAIT cells is useful for, inter alia, diagnostic purposes as well as in applications for investigating the role that MAIT cells play in immunity. The ability of the [MR1-L] of the invention to bind to mammalian MAIT cells and modulate MAIT cell activity, also makes them useful for therapeutic applications such as the treatment or prophylaxis of diseases or disorders associated with aberrant MAIT cell activity. These should be understood as extending to animal models other than humans or other mammalian MAIT cells.

In one aspect of the present invention the compounds, [MR1-L] or [MR1-L]$_n$ modulate the activity of MAIT Cells. Such modulating refers to an increase, decrease or inhibition of the activity of the MAIT cells.

In an embodiment the MR1 polypeptide of this invention comprises all or part of SEQ ID NO: 1 (identified in Genbank as ID NO U22963) for example, SEQ ID NO: 2 or a functional derivative thereof, having one or more amino acid substitutions, additions and/or deletions to SEQ ID NO:1 or SEQ ID NO: 2.

SEQ ID NO:1: (This is fully translated human MR1, including Leader Sequence.)

MGELMAFLLPLIIVLMVKHSDSRTHSLRYFRLGVSDPIHGVPEFISVGYV

DSHPITTYDSVTRQKEPRAPWMAENLAPDHWERYTQLLRGWQQMFKVELK

RLQRHYNHSGSHTYQRMIGCELLEDGSTTGFLQYAYDGQDFLIFNKDTLS

WLAVDNVAHTIKQAWEANQHELLYQKNWLEEECIAWLKRFLEYGKDTLQR

TEPPLVRVNRKETFPGVTALFCKAHGFYPPEIYMTWMKNGEEIVQEIDYG

DILPSGDGTYQAWASIELDPQSSNLYSCHVEHCGVHMVLQVPQESETIPL

VMKAVSGSIVLVIVLAGVGVLVWRRRPREQNGAIYLPTPDR.

SEQ ID NO: 2: (This is mature human MR1, without Leader sequence)

RTHSLRYFRLGVSDPIHGVPEFISVGYVDSHPITTYDSVTRQKEPRAPWM

AENLAPDHWERYTQLLRGWQQMFKVELKRLQRHYNHSGSHTYQRMIGCEL

LEDGSTTGFLQYAYDGQDFLIFNKDTLSWLAVDNVAHTIKQAWEANQHEL

LYQKNWLEEECIAWLKRFLEYGKDTLQRTEPPLVRVNRKETFPGVTALFC

KAHGFYPPEIYMTWMKNGEEIVQEIDYGDILPSGDGTYQAWASIELDPQS

SNLYSCHVEHCGVHMVLQVPQESETIPLVMKAVSGSIVLVIVLAGVGVLV

WRRRPREQNGAIYLPTPDR.

SEQ ID NO: 3: Human Leader sequence:

MGELMAFLLPLIIVLMVKHSDS

In an embodiment the MR1 polypeptide of this invention comprises all or part of SEQ ID NO: 4 (identified in Genbank as at NM008209) for example, SEQ ID NO: 5 or a functional derivative thereof, having one or more amino acid substitutions, additions and/or deletions to SEQ ID NO: 4 or SEQ ID NO: 5.

SEQ ID NO: 4: (This is fully translated murine MR1, including Leader sequence)

MMLLLPLLAVFLVKRSHTRTHSLRYFRLAVSDPGPVVPEFISVGYVDSHP

ITTYDSVTRQKEPKAPWMAENLAPDHWERYTQLLRGWQQTFKAELRHLQR

HYNHSGLHTYQRMIGCELLEDGSTTGFLQYAYDGQDFIIFNKDTLSWLAM

DYVAHITKQAWEANLHELQYQKNWLEEECIAWLKRFLEYGRDTLERTEHP

VVRTTRKETFPGITTFFCRAHGFYPPEISMTWMKNGEEIAQEVDYGGVLP

SGDGTYQTWLSVNLDPQSNDVYSCHVEHCGRQMVLEAPRESGDILRVSTI

SGTTILIIALAGVGVLIWRRSQELKEVMYQPTQVNEGSSPS

SEQ ID NO: 5: (This is mature murine MR1 lacking Leader sequence)

RTHSLRYFRLAVSDPGPVVPEFISVGYVDSHPITTYDSVTRQKEPKAPWM

AENLAPDHWERYTQLLRGWQQTFKAELRHLQRHYNHSGLHTYQRMIGCEL

LEDGSTTGFLQYAYDGQDFIIFNKDTLSWLAMDYVAHITKQAWEANLHEL

QYQKNWLEEECIAWLKRFLEYGRDTLERTEHPVVRTTRKETFPGITTFFC

RAHGFYPPEISMTWMKNGEEIAQEVDYGGVLPSGDGTYQTWLSVNLDPQS

NDVYSCHVEHCGRQMVLEAPRESGDILRVTISGTTILIIALAGVGVLIWR

RSQELKEVMYQPTQVNEGSSPS

SEQ ID NO: 6: Mouse Leader sequence:

MMLLLPLLAVFLVKRSHT

SEQ ID NOs: 2 and 5 represent the human and mouse mature MR1 protein sequences, respectively, with the translated leader sequence removed. SEQ ID NOs: 1 and 4 represent the human and mouse MR1 protein sequences, respectively, including the translated leader sequence. The translated leader sequence for the human and mouse MR1 protein sequences are represented by SEQ ID NOs: 3 and 6, respectively. Table 1 provides a summary of the MR1 sequences.

TABLE 1

| SEQ ID NO | MR1 Sequence |
|---|---|
| 2 | Mature MR1 protein - human |
| 1 | Mature MR1 protein + leader sequence - human |
| 3 | MR1 leader sequence - human |
| 5 | Mature MR1 protein - mouse |
| 4 | Mature MR1 protein + leader sequence - mouse |
| 6 | MR1 leader sequence - mouse |

Reference to parts thereof means any portion of which contains functional domains, such as the ligand binding site. Functional derivatives include naturally-occurring variants, for example, polymorphisms, splicing forms, homologs from other species, etc. It also includes synthetic derivatives, i.e., artificially created MR1 polypeptides having modified amino acid sequence as compared to SEQ ID NO: 1 (U22963) or SEQ ID NO: 2 (NM008209). Modification of amino acid sequence includes any mutation, deletion, or addition thereof including modifications introduced for the purpose of creating multimeric forms of the MR1-ligand subunit for diagnostic, research or therapeutic applications. Functional derivative means that MR1 polypeptide retains the ability to bind MAIT cells or a specific receptor thereof or to bind a ligand of MR1.

In an embodiment, the introduction of certain mutations in the MR1 sequence enables the production of MR1 compound tetramers with enhanced MAIT cell binding ability. Accordingly, in one embodiment, the MR1 utilised in accordance with the invention comprises at least one mutation selected from the list consisting of K43A, K43M, K43I, K43L, K43F, K43Q, Y7A, Y7W, R9K, R9A, S24F, Y62A, L66A, L66F, W69A, R94K, R94A, I96A, I96F, W156A. Also contemplated are mutations in surface exposed groups including but not limited to the list consisting of D57, R61, L65, M72, V75, R79, T138, Q141, N146, H148, L151, N155, E158, and R167. The number refers to the amino acid residue number in the wild-type mature amino acid sequences (SEQ ID NO: 1 and SEQ ID NO: 2).

In an embodiment the MR1 comprises a K43A mutation.

In an embodiment, the MR1 subunit [MR1] comprises the structure wherein is the heavy chain comprising the domains 1, 2, or 3 and is 2-microglobulin light chain.

The MR1 subunits can be expressed in a suitable host cell, preferably isolated, and, if necessary, solubilized. Any suitable method for obtaining purified proteins may be used.

Another aspect contemplated herein is a method for preparing [MR1-L] the method comprising re-folding [MR1] in the presence of compounds which facilitate the binding of ligand bound in a ring-open conformation to a residue with the MR1 amino acid sequence. In an embodiment, the compounds facilitate a Schiff induced base bond to an amino acid residue such as lysine (e.g. lysine 43 of human MR1 [SEQ ID NO:1], or lysine 43 of murine MR1 [SEQ ID NO: 2]. In an embodiment, the compound is 5-amino-6-D-ribitylaminouracil (5-A-RU) which together with small molecule metabolites form a ring-open conformation of the compounds of formula (I), bound to Lysine 43 of human or murine MR1 via a Schiff induced base bond.

In an embodiment, an ring-open conformation of 5-OP-RU or 5-OE-RU is formed.

Usually the MR1 binding site will be free prior to addition of the target antigenic compound.

In an embodiment, MR1 will bind an antigenic compound in the groove formed by the two membrane distal domains, 2 and 1.

In an embodiment, the MR1-5-OP-RU or MR1-5-OE-RU complex forms a hydrogen bond to Tyr95 of the MAIT TCR.

In an embodiment, the [MR1] refolding mixture also includes 2 microglobulin. In an embodiment, [MR1] comprises a heavy chain comprising domains 1, 2 or 3 of MR1 and a 2 microglobulin chain.

In an embodiment, the small molecule metabolites are glyoxal or methylglyoxal.

In forming the MR1-ligand complexes, the MR1 subunits are expressed in a suitable host cell, and, if necessary, solubilized. The subunits are combined with an antigenic compound and allowed to fold in vitro to form a stable heterodimer complex with intrachain disulfide bonded domains. The compound may be included in the initial folding reaction, or may be added to the empty heterodimer in a later step. Usually the MR1 binding site will be free prior to addition of the target antigenic compound.

In an embodiment, MR1 will bind an antigenic compound in the groove formed by the two membrane distal domains, 2 and 1.

Conditions that permit folding and association of MR1 and ligands are known in the art, see for example Altman et al. (1993) and Garboczi et al. (1992). It will be readily understood by one of skill in the art that the specific folding conditions are not critical for the practice of the invention.

It should be understood that for the purposes of therapy, the MR1-ligand complexes can be formed in vivo by the administration of the compound in an unbound form to a subject whereby a natural ligand-MHC complex is formed.

The ligands or compounds of the invention may be prepared in a variety of ways. Conveniently, they can be synthesized by conventional techniques employing automatic synthesizers, or may be synthesized manually. The ligands may also be isolated from natural sources and purified by known techniques, including, for example, chromatography on ion exchange materials, separation by size, immunoaffinity chromatography and electrophoresis.

Scheme 1 outlines the general steps to produce compounds of formula (I). First, compounds of formula (a), wherein Y and Z are as above defined and Hal denotes a halogen, may undergo a condensation reaction with $R_2$—H wherein $R_2$ is as above defined, resulting in compounds of formula (b). An addition reaction with compounds of formula (b) may result in compounds of formula (c) wherein Y, Z and $R_2$ are as above defined and W is either an amino, hydroxyl or suitable leaving group. A reaction with compounds of formula (c) and $R_1$, wherein $R_1$ is as above defined, results in compounds of formula (I).

Scheme 1:
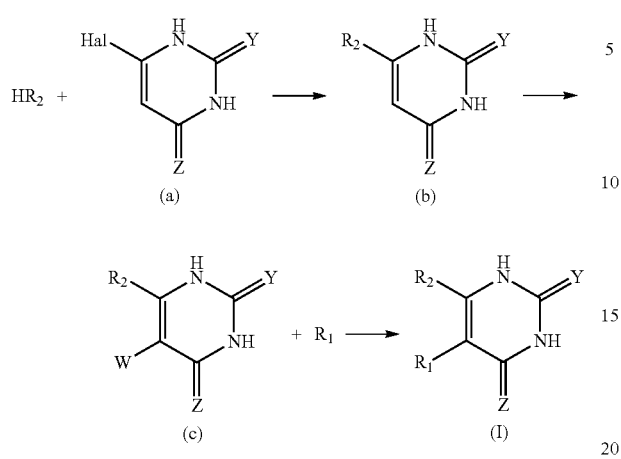
In an embodiment, compounds of formula (a) may be selected from:
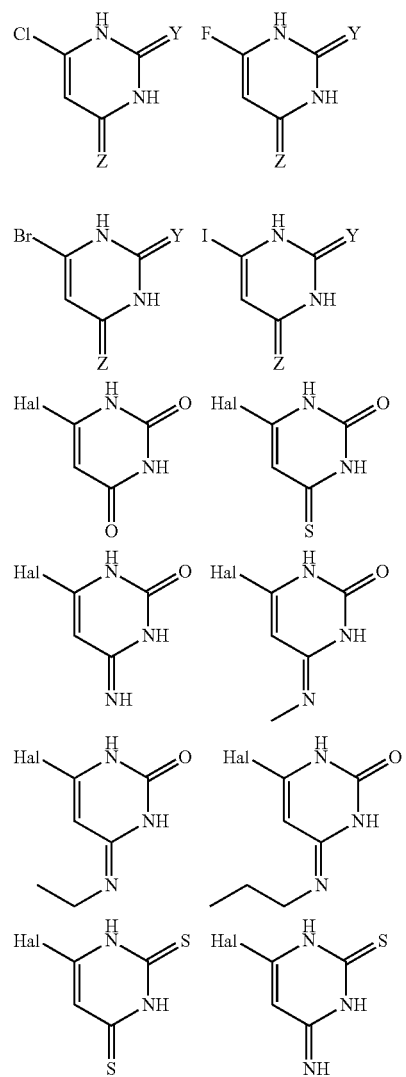
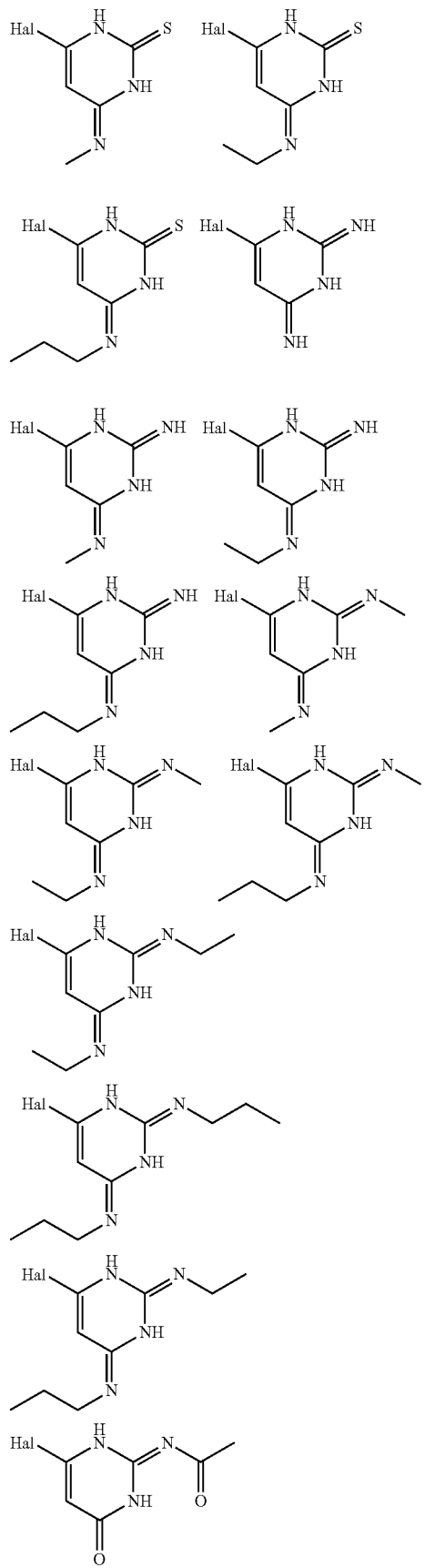

-continued

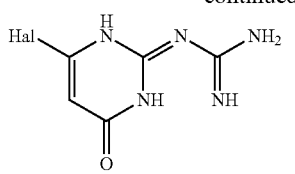

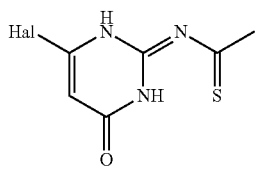

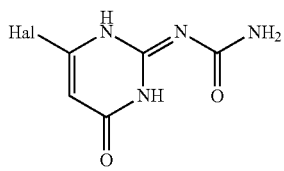

In an embodiment, compounds of formula (c) may be selected from:

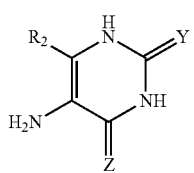

(d)

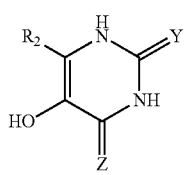

(e)

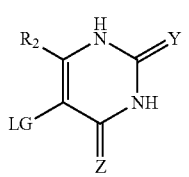

(f)

Amines of formula (d) may undergo a condensation reaction with $R_1$ to produce compounds of formula (I). The hydroxyl group of formula (e) may undergo a condensation reaction with $R_1$ to produce compounds of formula (I). Compounds of formula (f) may undergo elimination reactions to produce compounds of formula (I). These are shown in Scheme 2.

Scheme 2:

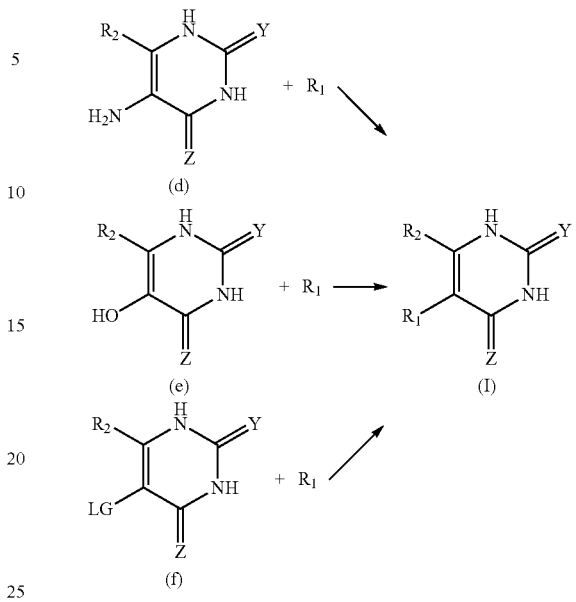

When $HR_2$ is $HNR_3$ selected from the group consisting of HNH(optionally substituted $C_{1-6}$alkyl), HN(optionally substituted $C_{1-6}$alkyl)(optionally substitute aryl), HN(optionally substitute $C_{1-6}$alkyl)$_2$, $HR_3$ may undergo a condensation reaction with compounds of formula (a) to produce compounds of formula (b') as shown in scheme 3.

Scheme 3:

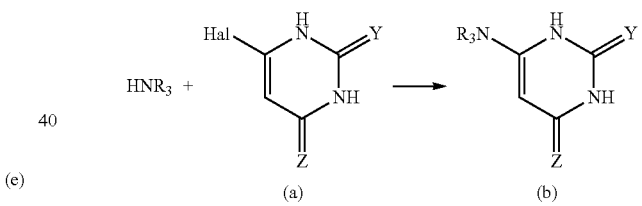

When $HR_2$ is $R_2$ selected from an optionally substituted $C_{1-8}$alkyl, $HR_2$ may undergo a catalysed reaction to produce compounds of formula (g) as shown in scheme 4.

Scheme 4:

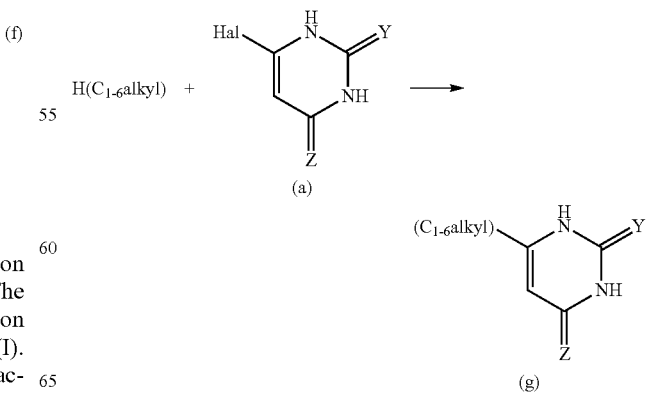

When $HR_2$ is $HOR_4$ wherein —$OR_4$ is selected from —O(optionally substituted $C_{1-6}$alkyl) or —OC(O)($C_{1-6}$ alkyl), $HR_2$ may undergo a reaction with compounds of formula (a) to produce compounds of formula (b″) as shown in scheme 5. Examples of such reactions comprise the Williamson ether synthesis, reductive etherification or the Mitsunobu Reaction.

Scheme 5:

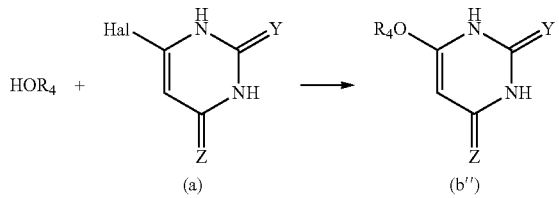

(a)  (b″)

When $HR_2$ is $HSR_5$ wherein —$SR_5$ is selected from —S(optionally substituted $C_{1-6}$alkyl), —SC(O)($C_{1-6}$alkyl) or —S(O)(optionally substituted $C_{1-6}$alkyl), $HR_2$ may undergo a catalysed reaction with compounds of formula (a) to produce compounds of formula (b‴) as shown in scheme 6.

Scheme 6:

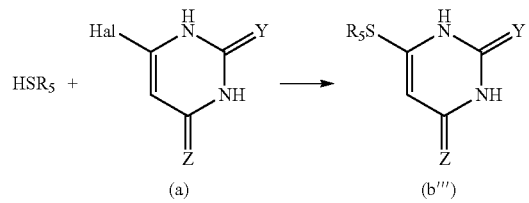

(a)  (b‴)

A compound of formula (d) may undergo a condensation reaction with a compound of formula $R_1$ to produce compounds of formula (h) as shown in scheme 7 wherein —$NR_6$ is selected from the group consisting of —X—C(O)—$R_1$' (where $R_1$' is H, or optionally substituted $C_1$-$C_6$alkyl, and X is a divalent linker selected from the group consisting of —$NR_2$'— optionally substituted $C_1$-$C_3$alkylene-, —N=$CR_2$'—, —$NR_2$'—C(O)—, where $R_2$' is selected from H, halogen, CN, or optionally substituted $C_1$-$C_6$alkyl).

Scheme 7:

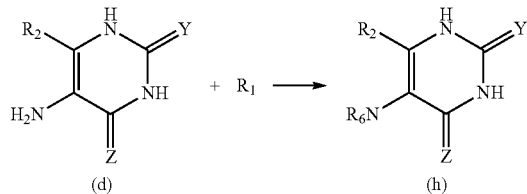

(d)  (h)

A compound of formula (e) may undergo a condensation reaction with a compound of formula $R_1$ to produce compounds of formula (i) as shown in scheme 8 wherein —$OR_7$ is selected from the group consisting of —X—C(O)—$R_1$' (where $R_1$' is H, or optionally substituted $C_1$-$C_6$alkyl, and X is a divalent linker selected from the group consisting of —O— optionally substituted $C_1$-$C_3$alkylene- or —O—C (O)—. Examples of such reactions comprise the Williamson ether synthesis, reductive etherification or the Mitsunobu Reaction.

Scheme 8:

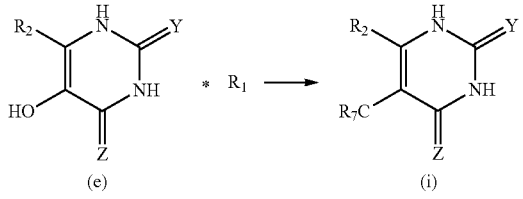

(e)  (i)

A compound of formula (f) may undergo a catalysed elimination reaction with a compound of formula $R_1$ to produce compound of formula (j) as shown in scheme 9 wherein —$SR_8$ is selected from the group consisting of —X—C(O)—$R_1$' (where $R_1$' is H, or optionally substituted $C_1$-$C_6$alkyl, and X is a divalent linker selected from the group consisting of —S— optionally substituted $C_1$-$C_3$alkylene-, —S(O)— optionally substituted $C_1$-$C_3$alkylene, or —S—C(O)—.

Scheme 9:

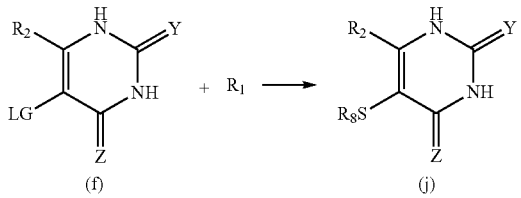

(f)  (j)

The monomeric MR1-ligand complex has the formula ([MR1]-L) (herein MR1-ligand subunit). [MR1] comprises a heavy chain comprising domains 1, 2 or 3 of MR1 and a 2 microglobulin chain. L is a ligand including an antigen or chemically derived binding agent.

The [MR1-L] described herein have enhanced ability to bind MAIT cells. The multimeric binding complex has the formula [MR1-L]$_n$, where n≥2, usually n≥4, and usually n≤10. The multimeric complex stably binds through covalent interactions to a MAIT cell receptor having the appropriate antigenic specificity. When compared to the binding of an [MR1-L] "monomer" subunit to a MAIT cell, the binding complex will have greatly increased stability, usually having an increase of at least about 10-fold in t1/2, more usually an increase of about 20-fold, and may be increased as much as about 50-fold or greater.

The resulting multimer will be stable over long periods of time. Usually not more than about 10% of the multimer will be dissociated after storage at 4° C. In an embodiment, the multimer will be formed by binding the monomers to a multivalent entity through specific attachment sites on the or subunit, as described below in detail. The multimer may also be formed by chemical cross-linking of the monomers. A number of reagents capable of cross-linking proteins are known in the art, illustrative entities include: azidobenzoyl hydrazide, N-[4-(p-azidosalicylamino)butyl]-3'-[2'-pyridyl-dithio]propionamide), bis-sulfosuccinimidyl suberate, dimethyladipimidate, disuccinimidyltartrate, N- -maleimidobutyryloxysuccinimide ester, N-hydroxy sulfosuccinimidyl-4-azidobenzoate, N-succinimidyl [4-azidophenyl]-1,3'- dithiopropionate, N-succinimidyl [4-iodoacetyl] aminobenzoate, glutaraldehyde, formaldehyde and succinimidyl 4-[N-maleimidomethyl]cyclohexane-1-carboxylate.

The attachment site for binding to a multivalent entity may be naturally occurring, or may be introduced through genetic engineering. The site will be a specific binding pair member or one that is modified to provide a specific binding pair member, where the complementary pair has a multiplicity of specific binding sites. Binding to the complementary binding member can be a chemical reaction, epitope-receptor binding or hapten-receptor binding where a hapten is linked to the subunit chain. In a preferred embodiment, one of the subunits is fused to an amino acid sequence providing a recognition site for a modifying enzyme. The recognition sequence will usually be fused proximal to the carboxy terminus of one of the subunit to avoid potential hindrance at the antigenic agent binding site.

Modifying enzymes of interest include BirA, various glycosylases, farnesyl protein transferase, protein kinases and the like. The subunit may be reacted with the modifying enzyme at any convenient time, usually after formation of the monomer. The group introduced by the modifying enzyme, e.g. biotin, sugar, phosphate, farnesyl, etc. provides a complementary binding pair member, or a unique site for further modification, such as chemical cross-linking, biotinylation, etc. that will provide a complementary binding pair member. An alternative strategy is to introduce an unpaired cysteine residue to the subunit, thereby introducing a unique and chemically reactive site for binding. The attachment site may also be a naturally occurring or introduced epitope, where the multivalent binding partner will be an antibody, e.g. IgG, IgM, etc. Any modification will be at a site, e.g. C-terminal proximal, that will not interfere with binding.

Exemplary of multimer formation is the introduction of the recognition sequence for the enzyme BirA, which catalyzes biotinylation of the protein substrate. Another example is via chemical biotinylation at the C-terminal cysteine. The monomer with a biotinylated subunit is then bound to a multivalent binding partner, e.g. streptavidin, avidin or neutravidin, to which biotin binds with extremely high affinity. Streptavidin has a valency of 4, providing a multimer of [MR1-L]$_4$.

The multivalent binding partner may be free in solution, or may be attached to an insoluble support. Examples of suitable insoluble supports include beads, e.g. magnetic beads, membranes and microtiter plates. These are typically made of glass, plastic (e.g. polystyrene), polysaccharides, nylon or nitrocellulose. Attachment to an insoluble support is useful when the binding complex is to be used for the separation and/or isolation of MAIT cells.

Frequently, the [MR1-L] or multimeric complex thereof will be labeled, so as to be directly detectable, or will be used in conjunction with secondary labeled immunoreagents which will specifically bind the complex. In general the label will have a light detectable characteristic. Preferred labels are fluorophors, such as fluorescein isothiocyanate (FITC), rhodamine, Texas Red, phycoerythrin and allophycocyanin. Other labels of interest may include dyes (for example cyanine), enzymes, chemiluminescers, particles, radioisotopes, or combinations thereof. Conveniently, the multivalent binding partner will have the labeling group. Alternatively, a second stage label may be used.

The binding complex will be used to detect and/or separate antigen bound MAIT cells. The MAIT cells may be from any source, usually having the same species of origin as the MR1 heterodimer.

As used herein, the term "MAIT" cells, or "Mucosal-Associated Invariant T cells" refers to a population of T cells present in mammals, preferably humans, that generally display an invariant TCR alpha chain comprising for example V 7.2-J 33 (in humans), V 7.2-J 20 or V 7.2-J 12, a CDR3 of constant length, and a limited number of V segments together with an activated phenotype (CD44) (see, for example, Lantz and Bendelac. (1994); Tilloy et al. (1999); Treiner et al. (2003), the entire disclosures of each of which are herein incorporated by reference). This includes MAIT cells defined as MR1-Ag tetramer-positive by flow cytometric analysis or other tagging methods not expressing canonical V 7.2-J 33 TCR but functionally MAIT cells in their Ag-specificity. In an embodiment, MAIT cells are generally CD4$^+$ or CD4$^-$/CD8$^-$ (DN) or CD8 in humans, and are restricted by the non-classical MHC class I molecule MR1. In an embodiment, MAIT cells can be defined as CD3$^+$ CD4$^-$ CD161$^+$ TRAV1.2$^+$ (monoclonal antibody D5$^+$). In terms of localization, MAIT cells are considered to be generally absent from the thymus, liver, spleen and bone marrow, but are abundant in the gut lamina-propria (LP), the mesenteric lymph nodes (MLN), and in other mucosal tissues, such as the lungs. For the purposes of the present invention, in an embodiment, T cells that express the invariant V 7.2-J 33 alpha TCR chain are considered to be predominantly MAIT cells including the possibility that some T cells that do not express the invariant V 7.2-J 33 alpha TCR chain may also recognize MAIT ligands and function as MAIT cells, for example T cells expressing V 7.2-J 20 or V 7.2-J 12. Mostly, the invariant alpha chain is linked to an invariant CDR3 and with either V 2 or V 13. Also in an embodiment, the MAIT cells are present in a mucosal tissue, such as the gut or more specifically but not limited to, the gut lamina propria the mesenteric lymph nodes, the mucosal surfaces of the oral cavity, conjunctiva, reproductive tract, bladder and urinary tract, foreskin, the lungs, the esophagus, stomach, small intestine (as above), large intestine, rectum and peri-anal tissue.

Preferably, the MAIT cells are mouse or human cells or cells from other mammals.

The MAIT cells may be from an in vitro culture, or a physiologic sample such as, for example, a tissue sample both fresh and/or paraffin embedded. For the most part, the physiologic samples employed will be blood or lymph, but samples may also involve other sources of cells, particularly where MAIT cells may be invasive. Thus other sites of interest are tissues, or associated fluids, as in the brain, lymph node, neoplasms, spleen, liver, kidney, pancreas, tonsil, thymus, joints, synovia, and the like. The sample may be used as obtained or may be subject to modification, as in the case of dilution, concentration, or the like. Prior treatments may involve removal of cells by various techniques, including centrifugation, using Ficoll-Hypaque, panning, affinity separation, using antibodies specific for one or more markers present as surface membrane proteins on the surface of cells, or any other technique that provides enrichment of the set or subset of cells of interest.

In an embodiment, the [MR1-L] or [MR1-L]$_n$ is added to a suspension comprising MAIT cells of interest, and incubated at about 4 degrees sufficient to bind the available cell surface receptor. The incubation will usually be at least about 5 minutes and usually less than about 30 minutes. It is desirable to have a sufficient concentration of labeling reagent in the reaction mixture, so that labeling reaction is not limited by lack of labeling reagent. The appropriate concentration is determined by titration. The medium in which the cells are labeled will be any suitable medium as known in the art. If live cells are desired a medium will be chosen that maintains the viability of the cells. In an embodiment the medium is phosphate buffered saline containing from 0.1 to 0.5% fetal calf serum (FCS). Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

Where a second stage labeling reagent is used, the cell suspension may be washed and resuspended in medium as described above prior to incubation with the second-stage reagent. Alternatively, the second stage reagent may be added directly into the reaction mix.

A number of methods for detection and quantitation of labeled cells are known in the art. Flow cytometry is a convenient means of enumerating cells that are a small percent of the total population. Immunohistochemistry may also be used. Various immunoassays, e.g. ELISA, RIA, etc. may used to quantitate the number of cells present after binding to an insoluble support.

Flow cytometry may also be used for the isolation of a labeled subset of MAIT cells from a complex mixture of cells. The cells may be collected in any appropriate medium which maintains the viability of the cells, usually having a cushion of serum at the bottom of the collection tube. Various media are commercially available as described above. The cells may then be used as appropriate.

Alternative means of separation utilise the MR1-ligand subunit or multimeric complex thereof bound directly or indirectly to an insoluble support, e.g. column, microtiter plate, magnetic beads, etc. The cell sample is added to the binding complex. The MR1-ligand subunit or multimeric complex thereof may be bound to the support by any convenient means. After incubation, the insoluble support is washed to remove non-bound components. From one to six washes may be employed, with sufficient volume to thoroughly wash non-specifically bound cells present in the sample. The desired cells are then eluted from the MR1-ligand subunit or multimeric complex thereof. In particular the use of magnetic particles to separate cell subsets from complex mixtures is described in Miltenyi et al. (1990) Cytometry 11:231-238.

Detecting and/or quantitating MAIT cells in a sample or fraction thereof may be accomplished by a variety of specific assays which will known in the art, such as, for example, sandwich ELISA or ELISA assays. In general, the assay will measure the binding between a patient sample, usually blood derived, generally in the form of plasma, serum or cells and the subject multimeric binding complexes. The patient sample may be used directly, or diluted as appropriate, usually about 1:10 and usually not more than about 1:10,000. Assays may be performed in any physiological buffer, e.g. PBS, normal saline, HBSS, dPBS, etc.

The [MR1-L] or [MR1-L]$_n$ as herein described of the invention may be provided in non-soluble or soluble form, depending on the intended application.

In one embodiment the [MR1-L] or [MR1-L]$_n$ is between 50,000 Da and 1,000,000 Da, such as from 50,000 Da to 980,000; for example from 50,000 Da to 960,000; such as from 50,000 Da to 940,000; for example from 50,000 Da to 920,000; such as from 50,000 Da to 900,000; for example from 50,000 Da to 880,000; such as from 50,000 Da to 860,000; for example from 50,000 Da to 840,000; such as from 50,000 Da to 820,000; for example from 50,000 Da to 800,000; such as from 50,000 Da to 780,000; for example from 50,000 Da to 760,000; such as from 50,000 Da to 740,000; for example from 50,000 Da to 720,000; such as from 50,000 Da to 700,000; for example from 50,000 Da to 680,000; such as from 50,000 Da to 660,000; for example from 50,000 Da to 640,000; such as from 50,000 Da to 620,000; for example from 50,000 Da to 600,000; such as from 50,000 Da to 580,000; for example from 50,000 Da to 560,000; such as from 50,000 Da to 540,000; for example from 50,000 Da to 520,000; such as from 50,000 Da to 500,000; for example from 50,000 Da to 480,000; such as from 50,000 Da to 460,000; for example from 50,000 Da to 440,000; such as from 50,000 Da to 420,000; for example from 50,000 Da to 400,000; such as from 50,000 Da to 380,000; for example from 50,000 Da to 360,000; such as from 50,000 Da to 340,000; for example from 50,000 Da to 320,000; such as from 50,000 Da to 300,000; for example from 50,000 Da to 280,000; such as from 50,000 Da to 260,000; for example from 50,000 Da to 240,000; such as from 50,000 Da to 220,000; for example from 50,000 Da to 200,000; such as from 50,000 Da to 180,000; for example from 50,000 Da to 160,000; such as from 50,000 Da to 140,000; for example from 50,000 Da to 120,000; such as from 50,000 Da to 100,000; for example from 50,000 Da to 80,000; such as from 50,000 Da to 60,000; such as from 100,000 Da to 980,000; for example from 100,000 Da to 960,000; such as from 100,000 Da to 940,000; for example from 100,000 Da to 920,000; such as from 100,000 Da to 900,000; for example from 100,000 Da to 880,000; such as from 100,000 Da to 860,000; for example from 100,000 Da to 840,000; such as from 100,000 Da to 820,000; for example from 100,000 Da to 800,000; such as from 100,000 Da to 780,000; for example from 100,000 Da to 760,000; such as from 100,000 Da to 740,000; for example from 100,000 Da to 720,000; such as from 100,000 Da to 700,000; for example from 100,000 Da to 680,000; such as from 100,000 Da to 660,000; for example from 100,000 Da to 640,000; such as from 100,000 Da to 620,000; for example from 100,000 Da to 600,000; such as from 100,000 Da to 580,000; for example from 100,000 Da to 560,000; such as from 100,000 Da to 540,000; for example from 100,000 Da to 520,000; such as from 100,000 Da to 500,000; for example from 100,000 Da to 480,000; such as from 100,000 Da to 460,000; for example from 100,000 Da to 440,000; such as from 100,000 Da to 420,000; for example from 100,000 Da to 400,000; such as from 100,000 Da to 380,000; for example from 100,000 Da to 360,000; such as from 100,000 Da to 340,000; for example from 100,000 Da to 320,000; such as from 100,000 Da to 300,000; for example from 100,000 Da to 280,000; such as from 100,000 Da to 260,000; for example from 100,000 Da to 240,000; such as from 100,000 Da to 220,000; for example from 100,000 Da to 200,000; such as from 100,000 Da to 180,000; for example from 100,000 Da to 160,000; such as from 100,000 Da to 140,000; for example from 100,000 Da to 120,000; such as from 150,000 Da to 980,000; for example from 150,000 Da to 960,000; such as from 150,000 Da to 940,000; for example from 150,000 Da to 920,000; such as from 150,000 Da to 900,000; for example from 150,000 Da to 880,000; such as from 150,000 Da to 860,000; for example from 150,000 Da to 840,000; such as from 150,000 Da to 820,000; for example from 150,000 Da to 800,000; such as from 150,000 Da to 780,000; for example from 150,000 Da to 760,000; such as from 150,000 Da to 740,000; for example from 150,000 Da to 720,000; such as from 150,000 Da to 700,000; for example from 150,000 Da to 680,000; such as from 150,000 Da to 660,000; for example from 150,000 Da to 640,000; such as from 150,000 Da to 620,000; for example from 150,000 Da to 600,000; such as from 150,000 Da to 580,000; for example from 150,000 Da to 560,000; such as from 150,000 Da to 540,000; for example from 150,000 Da to 520,000; such as from 150,000 Da to 500,000; for example from 150,000 Da to 480,000; such as from 150,000 Da to 460,000; for example from 150,000 Da to 440,000; such as from 150,000 Da to 420,000; for example from 150,000 Da to 400,000; such as from 150,000 Da to 380,000; for example from 150,000 Da to 360,000; such as from 150,000 Da to 340,000; for example from 150,000 Da to 320,000; such as from 150,000 Da to 300,000; for example from 150,000 Da to 280,000; such as from 150,000 Da to 260,000; for example from 150,000 Da to 240,000; such as from 150,000 Da to 220,000; for example from 150,000 Da to 200,000; such as from 150,000 Da to 180,000; for example from 150,000 Da to 160,000.

In another embodiment the [MR1-L] or [MR1-L]$_n$ is between 1,000,000 Da and 3,000,000 Da, such as from 1,000,000 Da to 2,800,000; for example from 1,000,000 Da to 2,600,000; such as from 1,000,000 Da to 2,400,000; for example from 1,000,000 Da to 2,200,000; such as from 1,000,000 Da to 2,000,000; for example from 1,000,000 Da to 1,800,000; such as from 1,000,000 Da to 1,600,000; for example from 1,000,000 Da to 1,400,000.

In an embodiment, ligand can form a covalent bond with Lysine 43 of the MR1 heavy chain, thereby stabilizing the MR1-ligand interaction and enhancing the function of these ligands. Accordingly, in an embodiment modification of MR1 by a ligand as described herein has the effect of stabilizing the MR1-ligand complex and extending its half-life. As the skilled person would appreciate this has significant application for analytical, diagnostic or therapeutic purposes.

In an embodiment the ligand is a compound represented by formula (I) as herein defined. In an embodiment the ligand is 5-(2-oxoethylideneamino)-6-D-ribitylaminouracil (5-OE-RU) or 5-(2-oxopropylideneamino)-6-D-ribitylaminouracil (5-OP-RU), which were either isolated or generated in situ by mixing 5-amino-6-D-ribitylaminouracil (5-A-RU) with glyoxal or methylglyoxal, respectively, or functional analogues thereof including oxidised and reduced forms thereof.

It will be appreciated that, V 7.2-J 33 is a common T cell receptor expressed by MAIT cells. As used herein, "V 7.2-J 33" includes any variant, derivative, or isoform of the rearranged V 7.2-J 33 gene or encoded protein. Other T cell receptors contemplated herein include V 7.2-J 20 or V 7.2-J 12.

The determination of compounds which bind MR1 and either inhibit, reduce or promote the activation of human MAIT cells enables the design of methods for detecting the presence of MAIT cells.

In another aspect, the present invention provides a method of detecting the presence of MAIT cells in a biological sample from a subject, the method comprising the steps of a) contacting the biological sample with antigen presenting cells expressing MR1 bound to a ligand or a soluble form thereof, under conditions that would allow binding of the MR1 with MAIT cells present in the sample; and b) detecting the presence of MAIT cell bound MR1 in the biological sample. In an embodiment, the MR1 bound to the ligand is in a multimeric complex, wherein L is a compound represented by formula (I) as hereinbefore defined. In an embodiment, L is 5-(2-oxoethylideneamino)-6-D-ribitylaminouracil (5-OE-RU) or 5-(2-oxopropylideneamino)-6-D-ribitylaminouracil (5-OP-RU), which were either isolated or generated in situ by mixing 5-amino-6-D-ribitylaminouracil (5-A-RU) with glyoxal or methylglyoxal, respectively, or functional analogues thereof including oxidised and reduced forms thereof or prodrug or protected forms thereof.

Accordingly, in another aspect, the present invention provides a method of detecting the presence of MAIT cells in a biological sample from a subject, the method comprising the steps of a) contacting the biological sample with antigen presenting cells expressing MR1 bound to a ligand or a soluble form thereof, under conditions that would allow binding of the MR1, with MAIT cells present in the sample; and b) detecting the presence of MAIT cell activity, wherein L is a compound represented by formula (I) as hereinbefore defined. In an embodiment, L is 5-(2-oxoethylideneamino)-6-D-ribitylaminouracil (5-OE-RU) or 5-(2-oxopropylideneamino)-6-D-ribitylaminouracil (5-OP-RU), which were either isolated or generated in situ by mixing 5-amino-6-D-ribitylaminouracil (5-A-RU) with glyoxal or methylglyoxal, respectively, or functional analogues thereof including oxidised and reduced forms thereof. In an embodiment, the MR1 bound to the ligand is in a multimeric complex. In an embodiment, CD69 levels are used to determine the level of MAIT cell activity of MAIT TCR transduced cell lines.

In one embodiment, the MR1 bound to a ligand or a soluble form thereof is conjugated or covalently bound to a detectable moiety.

Figure 2:
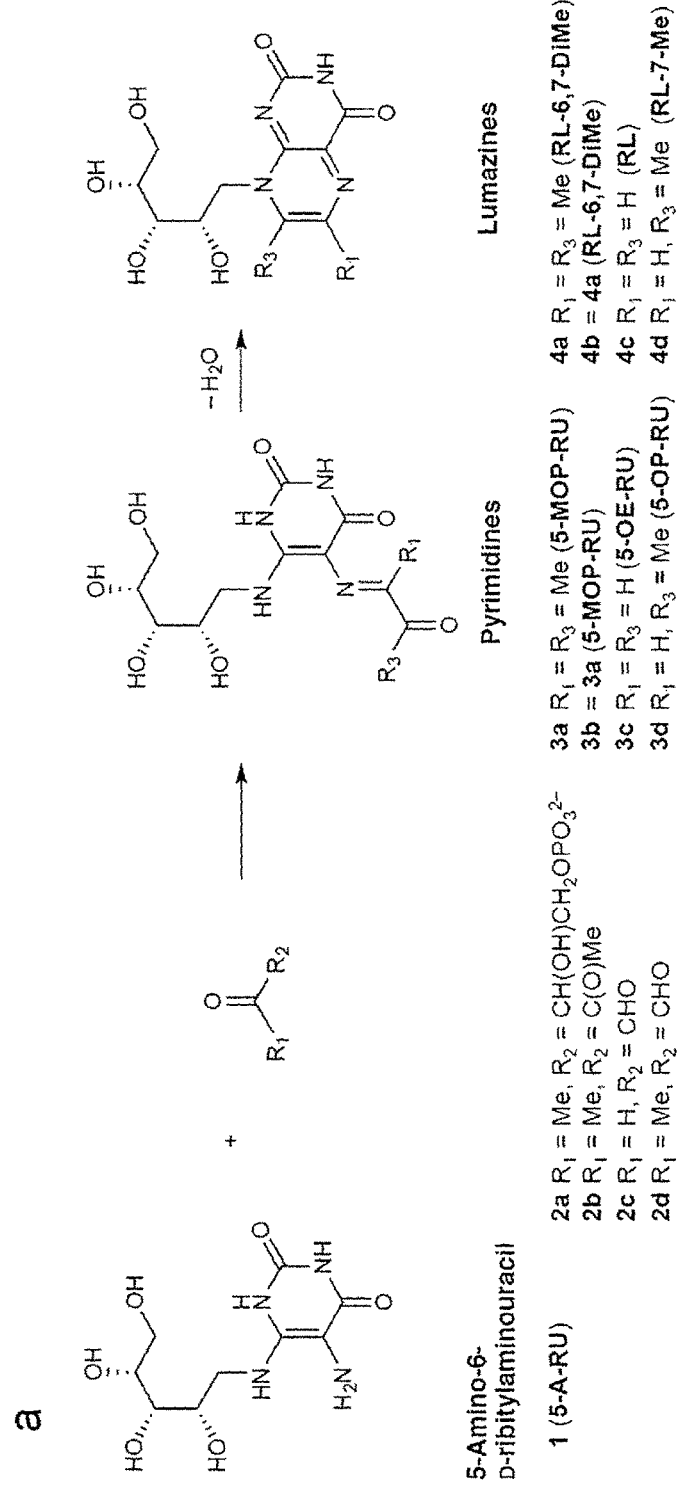
FIG. 2 is a schematic showing chemical formation of pyrimidines and lumazines from condensation of small metabolites with 5-A-RU (a) Series a, 5-A-RU (1) and 3,4-dihydroxy-2-butanone-4-phosphate (2a) form 5-(1-methyl-2-oxopropylideneamino)-6-D-ribitylaminouracil 5-MOP-RU, (3a) and then 6,7-dimethyl-8-D-ribityllumazine RL-6,7-DiMe (4a). Series b-d, 5-A-RU (1) with butane-2,3-dione (2b), glyoxal (2c), and methylglyoxal (2d) forms 5-MOP-RU (3b=3a), 5-OE-RU (3c) and 5-OP-RU (3d) respectively, and then RL-6,7-DiMe (4b=4a), 8-D-ribityllumazine RL (4c) and 7-methyl-8-D-ribityllumazine RL-7-Me (4d) respectively. (b) 2D NMR spectrum (HMBC) of isolated 5-OP-RU (3d) in DMSO-$d_6$ showing key $^1$H-$^{13}$C long range correlations that unambiguously characterize the imine adduct (3d), also identified in aqueous media (pH>6).
Figure 2:
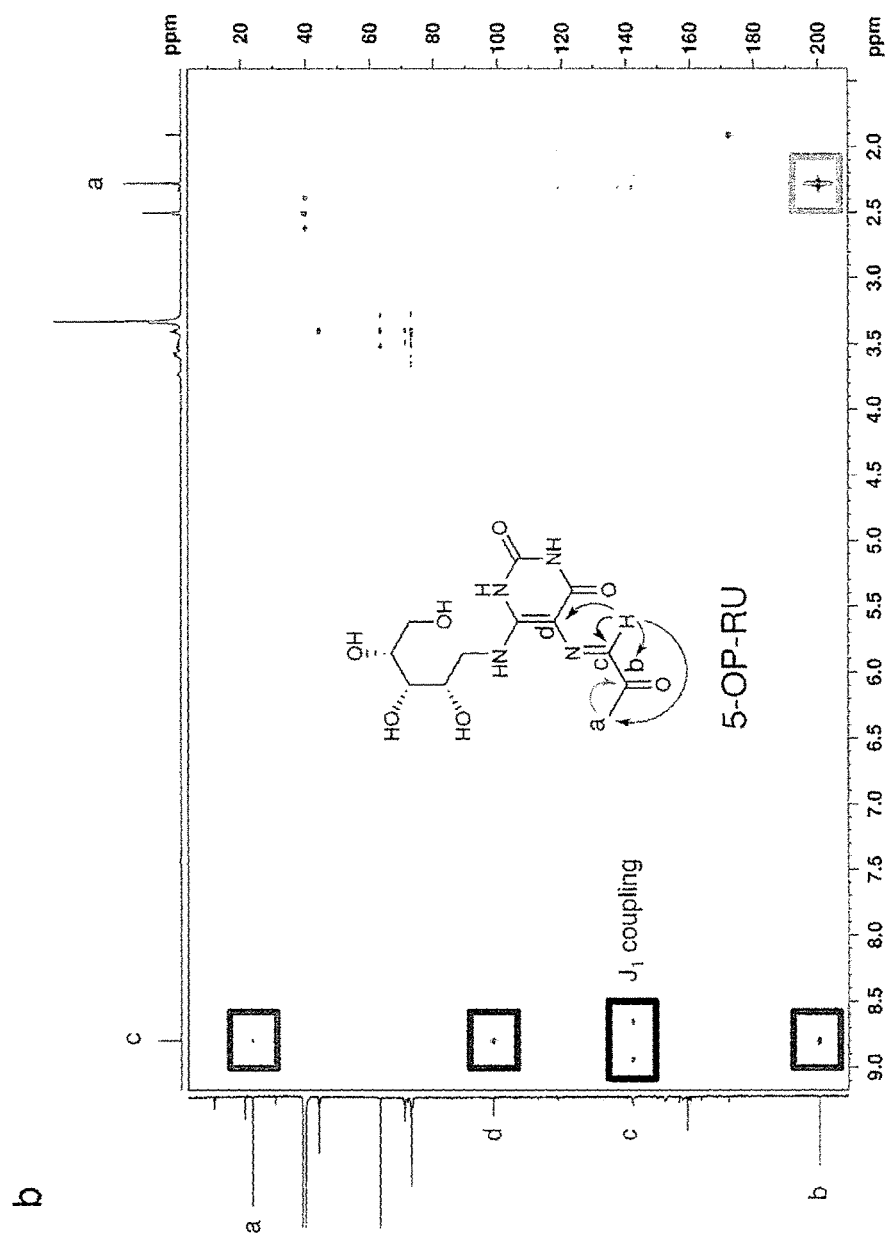

The preparation of 5-OE-RU or 5-OP-RU is outlined in FIG. 2.

In one embodiment, the compound, [MR1-L] or [MR1-L]$_n$ thereof modulates the activity of the MAIT cells by enhancing, decreasing or inhibiting the activity of the MAIT cells. In embodiments, reference to enhanced MAIT cell activity includes proliferation and/or accumulation of the MAIT cells, inducement, reduction or inhibition of the production by MAIT cells of TNF, Interferon gamma, RANTES, IL-10, IL-17 and/or other key cytokines or chemokines that regulate immunity or the expression of CD69 on MAIT cells or on cell lines transduced with the MAIT TCR. In an embodiment said modulation of MAIT cell activity is via MAIT cell TCRs. The expression "induces proliferation or accumulation of MAIT cells" in the present specification includes an effect of inducing the differentiation of immature MAIT cells into mature MAIT cells, which differentiation leads to the proliferation or the accumulation of MAIT cells. In addition, the term "induces accumulation of MAIT cells" in the present specification includes the accumulation of MAIT cells in a particular tissue or organ due to migration of mature and/or immature MAIT cells from other organs or tissues in the body. The induction of proliferation or accumulation of MAIT cells also includes in vivo effects, in vitro effects, and ex vivo effects. In another embodiment, the MR1-ligand subunit or multimeric complex thereof modulates MAIT cell activity by decreasing or inhibiting the activity of the MAIT cells. In one embodiment, MR1-ligand subunit or multimeric complex thereof leads to the depletion or apoptosis of MAIT cells. For example, the MR1-ligand subunit or multimeric complex thereof can also readily be modified so as to have properties of decreasing MAIT cell function, for example, by causing their depletion, for example, by including a toxic moiety, or driving antigen-induced MAIT cell apoptosis or by mediating depletion of the antibody-bound MAIT by cellular effectors.

The activity of MAIT cells of this invention can be assessed by standard methods known in the art for assessing cellular activity. In a non-limiting example, the activity of MAIT cells of this invention is assessed in a assay in which MAIT cells are incubated in the presence or absence of the agent or compounds, [MR1-L] or [MR1-L]$_n$ of the invention and with antigen presenting cells such as for example, B cells presenting the MHC class Ib molecule, MR1. Optionally, microbial flora is also present in the incubation. The effect of the presence of the agent or compounds, [MR1-L] or [MR1-L]$_n$ of the invention on the properties of the B or T cells, for example, their proliferation, activity, cytotoxicity, Ig production, or production of cytokines such as IL-10, RANTES, TNF-, TNF-α or IFN- are assessed. In other examples, assays may examine MAIT cell surface activation markers such as CD69, IL2R by flow cytometric techniques; alternatively, cytokine production of MAIT cells in response to ligand stimulation or blockade might evaluate a broad array of cytokines production by flow-based, cytokine array methods. In another illustrative example, the activity of MAIT cells can be assessed by ELISPOT assays which might enumerate MAIT cells through their individual cytokine production or other surrogate marred of cellular activation in response to ligand stimulation or blockade. In a non limiting example, MAIT cell activation can be assayed by CD69 upregulation in the case of MAIT TCR transduced cell lines or MAIT cells within PBMCs and intracellular cytokine staining for interferon (IFN-) and tumor necrosis factor (TNF) in the case of MAIT cells derived from PBMCs.

The activity of MAIT cells can also be assessed by exposing the cells to the [MR1-L] or [MR1-L]$_n$ itself and assessing its effect on any aspect of the cells' activity or behavior. In such assays, a baseline level of activity (e.g., cytokine production, proliferation, see below) of the MAIT cells is obtained in the absence of a ligand, and the ability of the [MR1-L] or [MR1-L]$_n$ to alter the baseline activity level is detected. In one such embodiment, a high-throughput screening approach is used to identify [MR1-L] or [MR1-L]$_n$ capable of affecting the activation of the MAIT cell receptor.

Examples of assays that can be used to assess MAIT cell activity can be found, inter alia, in U.S. Patent Application No. 20030215808; Kawachi et al. (2006) J Immunol. 176 (3):1618-27; Huang et al. (2005) J Biol Chem. 280(22): 21183-93; Treiner et al. (2005) Microbes Infect. 7(3):552-9; Treiner et al. (2003) Nature 422(6928): 164-9.

Any suitable physiological change that reflects MAIT cell activity can be used to evaluate test compounds, [MR1-L] or [MR1-L]$_n$. For example, one can measure a variety of effects, such as changes in gene expression (e.g. CD69), cell growth, cell proliferation, pH, intracellular second messengers, e.g., $Ca^{2+}$, IP3, cGMP, or cAMP, or activity such as ability to activate B cells or cytotoxicity. In one embodiment, the activity of MAIT cells is assessed by detecting the expression of V 7.2-Jα33-responsive genes or the production of V 7.2-Jα33-responsive cytokines or other factors, e.g., IL1O, RANTES, IFN-gamma or TNF-alpha.

In one embodiment, the activity of MAIT of this invention is assessed in a assay in which MAIT cells are incubated in the presence or absence of a test compound and with B cells, e.g. B cells presenting the MHC class Ib molecule, MR1. Optionally, microbial flora is also present in the incubation. The effect of the presence of the antibody on the properties of the B or T cells, e.g. their proliferation, activity, cytotoxicity, IgA production, or production of cytokines such as IL1O, RANTES, TNF- or IFN- are assessed. See, e.g., U.S. Patent Application No. 20030215808; Kawachi et al. (2006) J Immunol. 176(3):1618-27; Huang et al. (2005) J Biol Chem. 280(22):21183-93; Treiner et al. (2005) Microbes Infect. 7(3):552-9; Treiner et al. (2003) Nature 422(6928): 164-9.

In another embodiment, the effect of the compounds, [MR1-L] or [MR1-L]$_n$ on MAIT cells is assessed in non-human primates in vivo. For example, a pharmaceutical composition comprising compounds, [MR1-L] or [MR1-L]$_n$ of the present invention is administered to a non-human primate that is either healthy or affected by a mucosal immune condition, and the effect of the administration on, e.g., the number or activity of MAIT cells in the primate, on the IgA production in the gut of the primate, or on the progression of the condition is assessed. Any compound, [MR1-L] or [MR1-L]$_n$ that effects a detectable change in any of these MAIT-related parameters is a candidate for use in the herein-described methods.

In one embodiment, the [MR1-L] or [MR1-L]$_n$ causes an increase or decrease in MAIT cell activity of at least about 10%, 20%, 30%, 40%, 50%, or more, or alternatively, causes an increase or decrease in MAIT cell proliferation and/or accumulation by at least about 10%, 20%, 30%, 40%, 50%, or more.

The terms "increase", "enhance" and "up-regulate" with respect to MAIT cells means the increasing, enhancing or in any way positively affecting the activity of MAIT cells, preferably functional immune activity and/or number of MAIT cell receptors including but by no means limited to MAIT cells expressing V 7.2-J 33. The terms "decrease", "reduce", "inhibit" and "down-regulate" with respect to MAIT cells means the slowing down, reducing, or reversing, or in any way negatively affecting the activity of MAIT cells, preferably functional immune activity and/or number of MAIT cell receptors including but by no means limited to MAIT cells expressing V 7.2-J 33, V 7.2-J 20 or V 7.2-J 12.

The compounds, [MR1-L] or [MR1-L]$_n$ of this invention are able to modulate the activity of MAIT cells. For example, certain compounds, [MR1-L] or [MR1-L]$_n$ can stimulate the V 7.2-J 33 receptors and thereby activate MAIT cells and, in turn, enhance an MAIT cell-mediated immune response. Such compounds, [MR1-L] or [MR1-L]$_n$ are referred to herein interchangeably as "agonist", "activating" or "stimulatory" compounds, [MR1-L] or [MR1-L]$_n$. They are useful, e.g., for treating or preventing a condition caused by a decrease in MAIT cell activity or number, or where increased MAIT cell activity can ameliorate, prevent, eliminate, or in any way improve the condition or any symptom thereof. Other compounds, [MR1-L] or [MR1-L]$_n$, on the other hand, can inhibit the activation of MAIT cells, e.g. they can block the binding of endogenous ligands such as MR1 to the V 7.2-Jα33 receptors. These compounds, [MR1-L] or [MR1-L]$_n$ are thus referred to as "inhibitory" or "blocking" [MR1-L] or [MR1-L]$_n$. Such compounds, [MR1-L] or [MR1-L]$_n$ are useful, inter alia, for decreasing MAIT immune cell activity, e.g. for the treatment or prevention of conditions involving excess MAIT cell activity or number, or where decreased MAIT cell activity can ameliorate, prevent, eliminate, or in any way improve the condition or any symptom thereof. In an embodiment, the compounds, [MR1-L] or [MR1-L]$_n$ are capable of depleting MAIT cells by causing the elimination of MAIT cells in vitro or in vivo. For example, an [MR1-L] or [MR1-L]$_n$ may mediate killing of MAIT cells (e.g. CDC, ADCC, or by use of a toxic moiety).

In an embodiment, the ability of the compounds, [MR1-L] or [MR1-L]$_n$ to interact with MR1 and activate human MAIT cells makes them useful for, increasing MAIT cell activity in subjects having a disease or condition in which increased MAIT cell activity is beneficial, including those caused or characterized by insufficient MAIT cell activity.

It will also be appreciated that the compounds, [MR1-L] or [MR1-L]$_n$ are useful for decreasing MAIT cell activity in subjects having a disease or condition in which decreased MAIT cell activity is beneficial, including those caused or characterized by excessive MAIT cell activity.

Reference to excessive MAIT cell activity should be understood as a reference to overactive cellular activity, or to physiologically normal cellular activity which is inappropriate in that it is unwanted.

In an embodiment, the compounds, [MR1-L] or [MR1-L]$_n$ are used to treat or prevent cancer, an infectious disease, an immune disease involving the mucosa or an autoimmune or inflammatory disease or disorder.

Reference to "Autoimmune" disorders also includes any disorder, condition, or disease in which the immune system mounts a reaction against self cells or tissues, due to a breakdown in the ability to distinguish self from non-self or otherwise. Examples of autoimmune disorders include, but are not limited to, Celiac disease, Hashimoto's thyroiditis, pernicious anemia, Addison's disease, type I diabetes, rheumatoid arthritis, systemic lupus erythematosus, dermatomyositis, Sjogren's syndrome, lupus erythematosus, multiple sclerosis, myasthenia gravis, Reiter's syndrome, Grave's disease, polymyositis, Guillain Barre, Wegener's granulomatosus, polyarteritis nodosa, polymyalgia rheumatica, temporal arteritis, Bechet's disease, Churg-Strauss syndrome, Takayasu's arteritis, and others. Autoimmune disorders can involve any component of the immune system, and can target any cell or tissue type in the body.

Reference to "Inflammatory diseases" also refers to any disorder, condition, or disease characterized or caused by excessive or uncontrolled inflammation, or any aspect of inflammation such as redness, swelling, heat, pain, etc. Inflammatory diseases include, but are not limited to, irritable bowel disease, Crohn's disease, ulcerative colitis, allergies, including allergic rhinitis/sinusitis, skin allergies such as urticaria/hives, angioedema, atopic dermatitis, food allergies, drug allergies, insect allergies, and rare allergic disorders such as mastocytosisasthma, asthma, arthritis, including osteoarthritis, rheumatoid arthritis, and spondyloarthropathies, gastrointestinal inflammation, as well as neuroinflammatory conditions, such as but not limited to Alzheimers disease (AD), multiple sclerosis (MS), amyotrophic lateral sclerosis (ALS), Parkinson's disease (PD), stroke, and variant Creuzfeldt-Jacob disease.

The compounds, [MR1-L] or [MR1-L]n as described in this invention can be provided in any form suitable for the intended administration. Suitable forms include pharmaceutically (i.e. physiological) acceptable salts, pre- or prodrug forms of the therapeutic compound of the invention. In formulating into pharmaceutical preparations for therapeutic use, the compounds, [MR1-L] or [MR1-L]n of the invention may be dissolved in conventional physiologically compatible aqueous buffer solutions to which there may be added, optionally, pharmaceutical excipients to provide pharmaceutical preparations.

Such pharmaceutical carriers and excipients as well as suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3rd edition, Kibbe et al., Pharmaceutical Press (2000)). Standard pharmaceutical formulation techniques are well known to persons skilled in the art (see, e.g., 2005 Physicians' Desk Reference®, Thomson Healthcare: Montvale, N.J., 2004; Remington: The Science and Practice of Pharmacy, 20th ed., Gennaro et al., Eds. Lippincott Williams & Wilkins: Philadelphia, Pa., 2000). In particular, the pharmaceutical composition comprising the therapeutic compound, [MR1-L] or [MR1-L]n of the invention may be formulated in lyophilized or stable liquid form. The therapeutic compounds, [MR1-L] or [MR1-L]n of the invention may be lyophilized by a variety of procedures known in the art. Lyophilized formulations are reconstituted prior to use by the addition of one or more pharmaceutically acceptable diluents such as sterile water for injection or sterile physiological saline solution.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a chemical compound of the invention and its pharmaceutically acceptable acid addition salt. Metal salts of a chemical compound of the invention includes alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

The chemical compound of the invention may be provided in dissoluble or indissoluble forms together with a pharmaceutically acceptable solvents such as water, ethanol, and the like. Dissoluble forms may also include hydrated forms such as the monohydrate, the dihydrate, the hemihydrate, the trihydrate, the tetrahydrate, and the like. In general, the dissoluble forms are considered equivalent to indissoluble forms for the purposes of this invention.

The chemical compound of the invention or salt, solvate, tautomer, stereoisomer, or antibody conjugate thereof may be administered as such or in the form of a suitable prodrug.

The term "prodrug" denotes a compound, which is a drug precursor and which, following administration and absorption, release the drug in vivo via some metabolic process.

Particularly favoured prodrugs are those that increase the bioavailability of the compounds of the invention (e.g. by allowing an orally administered compound to be more readily absorbed into the blood) or which enhance delivery of the parent compound to a specific biological compartment (e.g. the brain or lymphatic system). Thus examples of suitable prodrugs of the substances according to the invention include compounds modified at one or more reactive or derivatizable groups of the parent compound. Of particular interest are compounds modified at a carboxyl group, a hydroxyl group, or an amino group. Examples of suitable derivatives are esters or amides.

The compositions of the present invention may be administered orally, parenterally, by inhalation spray, topically, rectally, nasally, buccally, vaginally or via an implanted reservoir. The administration as used herein includes subcutaneous, intravenous, intramuscular, intra-articular, intra-synovial, intrasternal, intrathecal, intrahepatic, intralesional and intracranial injection or infusion techniques.

Sterile injectable forms of the compositions of this invention may be aqueous or an oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include, for example, lactose. When aqueous suspensions are required for oral use, the active ingredient is combined with emulsifying and suspending agents. If desired, certain sweetening, flavoring or coloring agents may also be added.

Alternatively, the compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The compositions of this invention may also be administered topically, especially when the target of treatment includes areas or organs readily accessible by topical application, including diseases of the eye, the skin, or the lower intestinal tract. Suitable topical formulations are readily prepared for each of these areas or organs. For topical applications, the compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

Topical application for the lower intestinal tract can be effected in a rectal suppository formulation (see above) or in a suitable enema formulation. Patches may also be used.

The compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds, [MR1-L] or [MR1-L]$_n$ of the present invention are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

The invention further provides a method of modulating MAIT cell activity in a subject in need thereof, comprising the step of administering to said subject a pharmaceutical preparation, or compounds, [MR1-L] or [MR1-L]$_n$ of the invention as herein defined. In one embodiment, the MAIT cell activity is increased, wherein the subject has a disease or disorder wherein such enhancement may promote, enhance, and/or induce a therapeutic effect (or promotes, enhances, and/or induces such an effect in at least a substantial proportion of subjects with the disease or disorder and substantially similar characteristics as the subject, as may determined by, e.g., clinical trials). In one embodiment, the preparation or compounds induces the proliferation and/or accumulation of MAIT cells. In a further embodiment, the preparation or compounds induces the production of cytokines, for example IL-2 and/or IL-10. In another embodiment, the MAIT cell activity is inhibited, wherein the subject has a disease or disorder wherein such inhibition may promote, enhance, and/or induce a therapeutic effect (or promotes, enhances, and/or induces such an effect in at least a substantial proportion of patients with the disease or disorder and substantially similar characteristics as the patient—as may determined by, e.g., clinical trials).

In some embodiments, prior to the administration of the pharmaceutical preparation, or therapeutic compounds, [MR1-L] or [MR1-L]$_n$ of the invention, the presence of V 7.2-Jα33 on cells of the subject will be assessed, e.g., to determine the relative level and activity of MAIT cells in the patient as well as to confirm the binding efficacy of the antibodies to the MAIT cells of the subject. This can be accomplished by obtaining a sample of PBLs or cells from the site of the disorder (e.g., from mucosal tissue), and testing e.g., using immunoassays, to determine the relative prominence of markers such as, for example, CD4, CD8, etc., as well as V 7.2-Jα33 on the cells.

In one embodiment, where it is sought to increase the activity of a subjects MAIT cells, a "responder" test can be carried out. In brief, the ability of the pharmaceutical preparation, compounds, [MR1-L] or [MR1-L]$_n$ of the invention to increase the activity of the patient's MAIT cells is assessed, preferably the ability to induce the proliferation, activation, of cytokine expression of the MAIT cells. If the activity of the MAIT cells is increased by the pharmaceutical preparation, compounds, [MR1-L] or [MR1-L]$_n$ of the invention or composition, the patient is determined to be responsive to therapy with pharmaceutical preparation, compounds, [MR1-L] or [MR1-L]$_n$ of the invention, and optionally the patient is treated with an pharmaceutical preparation, therapeutic compounds, [MR1-L] or [MR1-L]$_n$ of the invention.

In other embodiments, the method may comprise the additional step of administering to said subject an appropriate additional therapeutic agent selected from an immunomodulatory agent, a hormonal agent, a chemotherapeutic agent, an anti-angiogenic agent, an apoptotic agent, an antibody that binds to and modulates a MAIT cell receptor, an anti-infective agent, a targeting agent, an anti-inflammation drug, a steroid, an immune system suppressor, an antibiotic, an anti-diarrheal drug, or an adjunct compound. Such additional agents can be administered to said subject as a single dosage form together with said compounds, [MR1-L] or [MR1-L]$_n$ of the invention, or as a separate dosage form. The dosage of the compounds, [MR1-L] or [MR1-L]$_n$ of the invention (or composition comprising compounds, [MR1-L] or [MR1-L]$_n$ of the invention, and the dosage of the additional therapeutic agent collectively) are sufficient to detectably induce, promote, and/or enhance a therapeutic response in the patient. Where administered separately, the composition comprising compounds, [MR1-L] or [MR1-L]$_n$ of the invention and the additional therapeutic agent are desirably administered under conditions (e.g., with respect to timing, number of doses, etc.) that result in a detectable combined therapeutic benefit to the subject.

Without limiting the present invention in any way, it has been found that MAIT cell proliferation/accumulation can be influenced by the presence of riboflavin producing microorganisms or TLR agonists. Accordingly, in an embodiment, the ligands and compounds of the present invention can be provided as a composition comprising at least one riboflavin producing microorganism, for example, but not limited to *Salmonella* and *Helicobacter pylori*, a culture supernatant thereof, or a physiologically active substance derived from the microorganism, or a TLR agonist, wherein said riboflavin producing microorganism, a culture supernatant thereof, or a physiologically active substance derived from the microorganism, or TLR agonist modulates the activity of MAIT cells. In an embodiment, the composition of microorganisms is referred to as a probiotic.

The term the "physiologically active substance" of the present invention includes substances contained in the riboflavin producing microorganism, secretion products of the microorganism, and metabolites of the microorganism which are capable of modulating MAIT cell activity either alone or in combination with other agents. In another aspect, the present invention provides a composition that modulates MAIT cells, comprising at least one substance selected from the group consisting of the following (a) the compound of Formula (I);
(b) [MR1-L] or [MR1-L]n as herein defined;
(c) at least one riboflavin producing microorganism or physiologically active substance derived from the microorganism; and
(d) a cell culture supernatant obtained from culture in which at least one riboflavin producing microorganism was present or a fraction of such supernatant In another aspect, the present invention provides use of the compounds, [MR1-L], [MR1-L]$_n$, or compositions of the present invention in the manufacture of a medicament for the treatment or prophylaxis of a disease condition in a subject in need thereof.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

The dosage of agent of the invention used in accordance with the methods of the invention are sufficient to detectably induce, promote, and/or enhance a therapeutic response in the subject.

The term "biological sample" as used herein includes but is not limited to a biological fluid (for example serum, lymph, blood), cell sample, or tissue sample (for example bone marrow or tissue biopsy including mucosal tissue such as from the gut, gut lamina propria, or lungs).

The terms "mammal", "mammalian" or "subject" as used herein includes humans, primates, livestock animals (eg. sheep, pigs, cattle, horses, donkeys), laboratory test animals (eg. mice, rabbits, rats, guinea pigs), companion animals (eg. dogs, cats) and captive wild animals (eg. foxes, kangaroos, deer). In an embodiment, the mammal or subject is human or other primate or a mouse.

In an embodiment, the [MR1-L] or [MR1-L]$_n$ forms a basis for the generation of mAbs, or engineered variants of mAbs, that specifically bind the MR1-ligand subunit or multimeric complex thereof. In an embodiment, the antibodies are bound with the activating agent for the purpose of detecting the MR1-agent complexes and/or blocking or enhancing their recognition by MAIT cells.

The methods of the present invention may be combined with any other methods generally employed in the treatment of a particular disease, such as immune disorders involving the mucosa. So long as a particular therapeutic approach is not known to be detrimental to the subjects condition in itself, and does not significantly counteract the activity of the agents or compositions of the invention, its combination with the present invention is contemplated.

When one or more additional therapeutic agents are used in combination with an agent or composition of this invention in a therapeutic regimen, there is no requirement for the combined results to be additive of the effects observed when each treatment is conducted separately. Although at least additive effects are generally desirable, any increased effect above one of the single therapies would be of benefit. Also, there is no particular requirement for the combined treatment to exhibit synergistic effects, although this is certainly possible and advantageous.

In connection with solid tumor treatment, the agents or compositions of the present invention may be used in combination with classical approaches, such as surgery, radiotherapy, chemotherapy, and the like. The invention therefore provides combined therapies in which a pharmaceutical composition of this invention is used simultaneously with, before, or after surgery or radiation treatment; or are administered to patients with, before, or after conventional chemotherapeutic, radiotherapeutic or anti-angiogenic agents, or targeted immunotoxins or coaguligands.

In other aspects, immunomodulatory compounds or regimens may be administered in combination with or as part of the agents or compositions of the present invention. Preferred examples of immunomodulatory compounds include cytokines. Various cytokines may be employed in such combined approaches. Examples of cytokines useful in the combinations contemplated by this invention include IL-2, IL-3, IL-4, IL-5, IL-6, IL-7, IL-8, IL-9, IL-IO, IL-12, IL-13, IL-15, TGF-beta, GM-CSF, M-CSF, G-CSF, TNF-alpha, TNF-beta, LAF, TCGF, BCGF, TRF, BAF, BDG, MP, LIF, OSM, TMF, PDGF, IFN-alpha, and IFN-beta. Cytokines used in the combination treatment or compositions of this invention are administered according to standard regimens, consistent with clinical indications such as the condition of the patient and relative toxicity of the cytokine.

The present compositions can also be administered in conjunction with anti-inflammatory agents, such as NSAIDS, aspirin, salsalate, diflunisal, ibuprofen, ketoprofen, nabumetone, piroxicam, naproxen, diclofenac, indomethacin, sulindac, tolmetin, etodolac, ketorolac, oxaprozin, celecoxib, corticosteroids, oral steroids, prednisone, prednisolone, beclomethasone, fluticasone, budesonide, betamethasone, dexamethasone, aclomethasone and clobetasone.

In a related aspect the present invention also provides a basis for generating mAbs, or engineered variants thereof, that specifically detect activating and non-activating MR1 ligands allowing their detection, quantitative estimation, blockade or enhancement.

In another aspect, the present invention provides a pharmaceutical composition comprising the compound, [MR1-L] or [MR1-L]$_n$, as hereinbefore described. In an embodiment, the compound, [MR1-L] or [MR1-L]$_n$ is in an amount effective to detectably MAIT cells. In an embodiment, the compound, [MR1-L] or [MR1-L]$_n$ is in an amount to detectably modulate MAIT cell activity. In an embodiment, the MAIT cells are present in a subject or in a biological sample comprising MAIT cells.

In an embodiment, the composition further comprises a pharmaceutically acceptable carrier or excipient.

Pharmaceutically acceptable carriers that may be used in compositions comprising the agent of the invention, include but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

It will be appreciated that the compounds of the invention can be used for the identification of further ligands for the purpose of blocking or activating MAIT cells or generating multimer MR1-ligand reagents, for example tetramers, for detection, monitoring or immunotherapy directed towards MAIT cells.

A non-limiting example of this further aspect of the invention involves the use of combinatorial chemistry employing the compound of Formula (I) as herein defined, used as the scaffold basis for identification of further ligands for the purpose of blocking or activating MAIT cells or generating multimer [MR1-L] reagents.

In an embodiment the compound is selected from 5-(2-oxoethylideneamino)-6-D-ribitylaminouracil (5-OE-RU) or 5-(2-oxopropylideneamino)-6-D-ribitylaminouracil (5-OP-RU), which were either isolated or generated in situ by mixing 5-amino-6-D-ribitylaminouracil (5-A-RU) with glyoxal or methylglyoxal, respectively, or functional analogues thereof including but not limited to oxidised and reduced forms thereof.

Without limiting the application of the present invention in any way, the method of the present invention facilitates the analysis, design and/or modification of ligands which interact with MR1 and form a complex which either inhibits or promotes the interaction of MR1 with MAIT cells. In this regard, reference to "analysis, design and/or modification" of an agent should be understood in its broadest sense to include:

(i) Randomly screening (for example, utilising routine high-throughput screening technology) to identify agents which exhibit some modulatory capacity with respect to MAIT cell activity and then analysing the precise nature and magnitude of the ligands modulatory capacity utilising the method of this aspect of the present invention. In this regard, existing crystals could be soaked with said agents or co-crystallisation could be performed. A combination of modelling and synthetic modification of the local compound together with mutagenesis of the MR1 binding site could then be performed for example. In screening for agents which may modulate activity, standard methods of phage display and also combinatorial chemistry may be utilised (Goodson et al., 1994; Terrett., 2000). Such interaction studies can also be furthered utilising techniques such as the Biacore analysis and NMR perturbation studies. Such agents are often commonly referred to as "lead" agents in terms of the random screening of molecules for their capacity to function either agonistically or antagonistically. Further, for example, binding affinity and specificity could be enhanced by modifying lead agents to maximise interactions with the MR1 binding site. Such analyses would facilitate the selection of agents which are the most suitable for a given purpose. In this way, the selection step is based not only on in vitro data but also on a technical analysis of sites of agent: MR1 interaction in terms of their frequency, stability and suitability for a given purpose. For example, such analysis may reveal that what appears to be an acceptable in vitro activity in respect of a randomly identified agent is in fact induced by a highly unstable interaction due to the presence of proximally located agent: MR1 sites which exhibit significant repulsive forces thereby de-stabilising the overall interaction between the agent and the MR1. This would then facilitate the selection of another prospective lead compound, exhibiting an equivalent degree of in vitro activity, but which agent does not, upon further analysis, involve the existence of such de-stabilising repulsive forces.

Screening for the modulatory agents herein defined can be achieved by any one of several suitable methods, including in silico methods, which would be well known to those of skill in the art and which are, for example, routinely used to randomly screen molecules for the purpose of identifying lead compounds.

These methods provide a mechanism for performing high throughput screening of putative modulatory agents such as the agents comprising synthetic, recombinant, chemical and natural libraries.

(ii) The candidate or lead agent (for example, the agent identified in accordance with the methodology described in relation to point (i)) could be modified in order to maximise desired interactions (for example, binding affinity to specificity) with MR1 and to minimise undesirable interactions (such as repulsive or otherwise destabilising interactions).

Methods of modification of a candidate or lead agent in accordance with the purpose as defined herein would be well known to those of skill in the art. For example, a molecular replacement program such as Amore (Navaza, 1994) may be utilised in this regard.

(iii) In addition to analysing fit and/or structurally modifying existing molecules, the method of the present invention also facilitates the rational design and synthesis of an agent, such as an agonistic or antagonistic agent, based on theoretically modelling an agent exhibiting the desired MR1 binding site interactive structural features followed by the synthesis and testing of the subject agent.

It should be understood that any one or more of applications (i)-(iii) above, may be utilised in identifying a particular agent.

The herein described [MR1-L] or [MR1-L]$_n$ thereof, or compositions comprising same can be included in kits, as diagnostic reagents for detecting the presence of MAIT cells or as reagents for modulating MAIT cell activity. It will be appreciated that the kit may contain other types of therapeutic compounds as well, such as other anti-inflammatory, antiviral, antiparasitic or antitumour agents. Preferably, the kits also include instructions for using the compounds, [MR1-L], [MR1-L]$_n$, or compositions comprising same for example, detailing the herein-described methods.

Certain embodiments of the invention will now be described with reference to the following examples which are intended for the purpose of illustration only and are not intended to limit the scope of the generality hereinbefore described.

EXAMPLES

Methods
Bacterial Strains and Mutants

*Lactococcus lactis* strains NZ9000 (wild-type), the NZ9000 RibA-deletion mutant, and the CB013 and CB021 roseoflavin resistant mutants have been previously described (Burgess C et al (2004)). CB013-derivatives: CB013ΔRibA, CB013ΔRibB, CB013ΔRibG and CB013ΔRibH were generated by insertion of EcoRI or EcoRV restriction sites incorporating either one or two stop codons into the individual genes using standard techniques. Inserted sequences:

```
RibG
attaacgtttccccctccttttcgagccagtGAATTCaggattgctaaat tcataaaatgctcatcattttccat
```

```
RibB
gatgctggaagctcgaatgattaatttagacgGAATTCATTAacttatct ctcttttgaatttgagttacctctcctat
```

```
RibA
tatcttttctggactaatcatttcggctgcacGAATTCaaatcagatctc cttcattttctctattctcatcatc
```

```
RibH
ggccctgctaagagttttgcgttgatgaaGATATCTTATTAttcgttaa aacgtgcaactacaattccatatttgg
```

The genotype of each mutant was verified by sequencing and multiple rounds of PCRs based on the mutated region to verify the purity of the genotype. The phenotype of each mutant was also checked using growth/absence of growth in Riboflavin assay medium overnight at 30° C. and comparing to a control of CB013. All mutants were unable to grow in the media while CB013 was capable of growth in Riboflavin-limiting conditions as it is an over-producer. *L. lactis* strains were grown at 30° C. without shaking, in M17 medium (Difco) containing 1% glucose and the addition of 3 μg/ml riboflavin where indicated. *Salmonella typhimurium* SL1344 was grown at 37° C. without shaking, in M17 medium (Difco) containing 1% glucose.

*Salmonella typhimurium* strains SL1344 and BRD509 have been previously described (Hoiseth S. K. & Stocker B. A. D. (1981)). The *Salmonella* ribDH mutants were constructed on an SL1344 background by lambda red-recombinase mediated allelic replacement followed by general transduction using phage P22 as previously described (Strugnell R. et al (1992) resulting in strain SL1344 RibDH. Primers:

```
B2(Sec)F:
5'-TAG GGA TAA CAG GGT AAT-GGT TCG ATA GCG TAA TGG

B2(Sec)R:
5'-TAG GGA TAA CAG GGT AAT-TAT CTT TCC GGC CTG TGA

B2(Kan)F:
5'-CTA AGG AGG ATA TTC ATA TG-GAC CGC GCT TGA AAT
GAT

B2(Kan)R:
5'-GAA GCA GCT CCA GCC TAC ACA-ATT GTT AAC AAT GAC
ACA
```

The complement of mutants was performed by transformation of ribDH genes resulting in strain SL1344 RibDH: RibDH. Mutation and reconstitution were verified by lack of growth or growth on Luria Agar, and by PCR. Mutants were grown on Luria agar containing 20 μg/ml riboflavin.

For MR1 refolds *Salmonella* wt and mutant strains were grown in M9 minimal media supplemented with histidine (77.6 μg/ml) and streptomycin (25 μg/ml) and 3 μg/ml riboflavin. *Enterococcus faecalis* was grown in Folic Acid Assay Medium (Difco) at 37° C. without agitation. *E. coli* DH5α was grown in M9 media. *L. lactis* CB013 and CB013 rib mutants were grown in Folic Acid Assay Medium (Difco) supplemented with Xanthine (6 μg/ml) and Yeast Nitrogen Base (6.8 mg/ml) at 30° C. without agitation.

Compounds

Glyoxal, methylglyoxal, 1,3-dihydroxyacetone dimer, DL-glyceraldehyde and butane-2,3-dione were purchased from Sigma. [1,2-$^{13}C_2$]glycolaldehyde (glycolaldehyde can be readily air-oxidized to form glyoxal) was purchased from Omicron Biochemicals. A synthesis of rRL-6-CH$_2$OH has been previously described (Kjer-Nielsen L. et al Nature (2012)). 5-amino-6-D-ribitylaminouracil was freshly prepared from 5-nitroso-6-D-ribitylaminouracil following a literature procedure (Plaut G. W. E. & Harvey R. A. (1971)). In brief, 5-nitroso-6-D-ribitylaminouracil (40.0 mg, 0.138 mmol, 1 eq) was dissolved in MilliQ water (3 mL) at 80° C. under argon. To the red solution was added sodium dithionite powder (1.2-3.3 eq). The colour changed instantly to pale-yellow. After stirring at 80° C. for 5 min, the solution was cooled under argon in an ice-water bath. For biological studies, the chilled solution was diluted with MilliQ water to make 50 mM stock solutions and stored in 1.5 mL aliquots at 20° C. for later use.

For NMR characterisation of pyrimidine intermediate 5-OP-RU (3d), a freshly prepared solution of 5-amino-6-D-ribitylaminouracil (5-A-RU, 1) was adjusted to pH 7.0 with 1M sodium hydroxide solution, lyophilized, dissolved in DMSO-d$_6$ and then filtered to removed salts. The solution was transferred to an NMR tube, filled with argon, and the concentration of 5-A-RU determined by NMR spectroscopy. Methylglyoxal (2 equivalents) was added, and the reaction monitored by NMR. Upon completion, 5-OP-RU was further purified using a Shimadzu preparative HPLC system equipped with a Phenomenex Luna 10 micron C18 250× 21.20 mm column (P/No 00G-4253-PO-AX) and a SPD-M20A diode array detector. Flow rate was 20 mL/min with linear gradient: 100% solvent A to 100% solvent B over 30 min where solvent A was 20 mM ammonium acetate in H$_2$O and solvent B was 20 mM ammonium acetate in MeCN—H$_2$O (80:20, v/v). Compound 3d was fully characterised by ESI-HRMS (Calculated for C$_{12}$H$_{17}$N$_4$O$_7^-$ m/z 329.1103, measured m/z 329.1116) and 1D and 2D NMR spectroscopy (FIG. 2b & FIG. 6).

5-amino-6-D-ribitylaminouracil (5-OP-RU, 3d)

$^1$H NMR (600 MHz, DMSO-d$_6$), 2.28 (3H, s), 3.38-3.43 (2H, m), 3.47-3.51 (1H, m), 3.52-3.55 (1H, m), 3.56-3.59 (2H, m), 3.73 (1H, m), 7.43 (1H, br s), 8.80 (1H, s); $^{13}$C NMR (150 MHz, DMSO-d$_6$) 23.5, 44.1, 63.1, 70.7, 72.8, 72.9, 98.5, 142.0, 152.1, 157.6, 159.1, 200.2. ESI-HRMS calcd for C$_{12}$H$_{17}$N$_4$O$_7^-$ [M-H]$^-$: 329.1103, found: 329.1116.

Stability of 5-OP-RU in Aqueous Media

Figure 7:
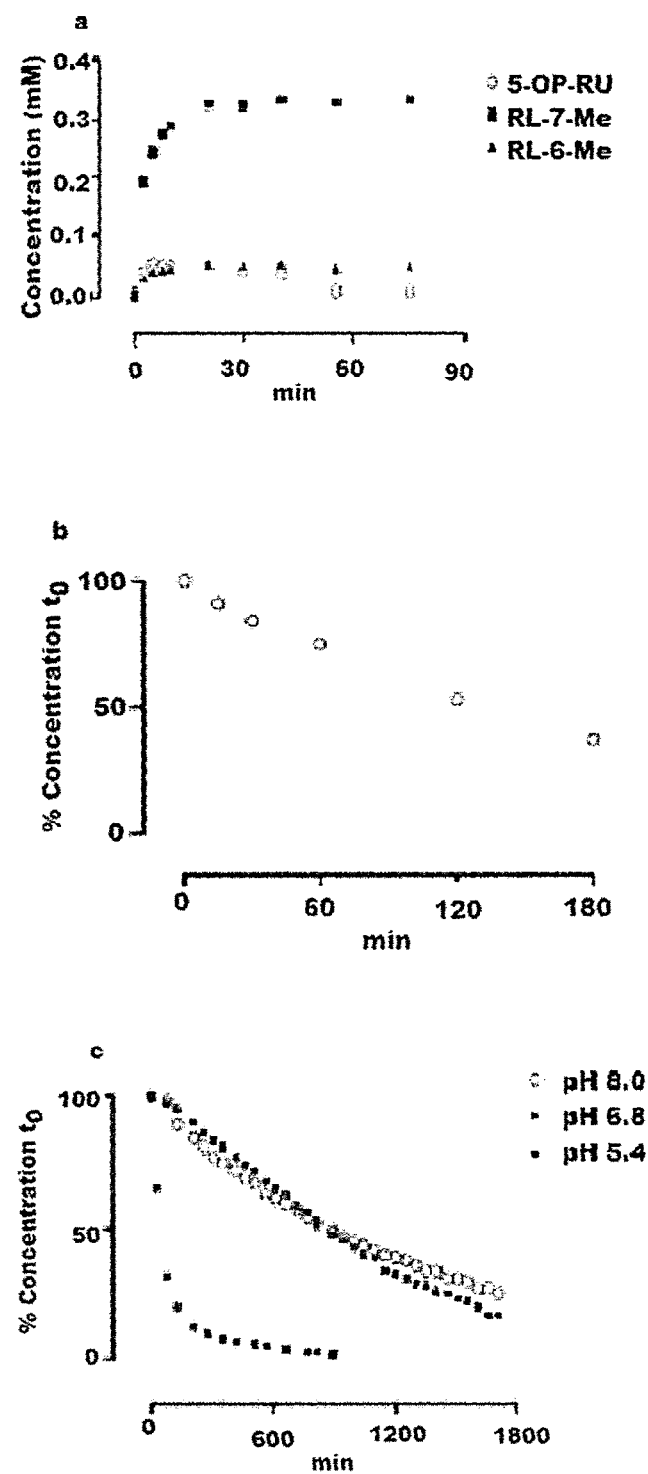
FIG. 7 is a graph showing stability of 5-OP-RU (a) Reaction between 5-A-RU (0.5 mM) and methylglyoxal (3 eq) at pH 6.8, 37° C. in MilliQ water. RL-6-Me represents 6-methyl-8-D-ribityllumazine. (b) Stability of purified 5-OP-RU (65 µM) at pH 6.8 and 37° C. The half-life was 135 mins. (c) Stability of purified 5-OP-RU (65 µM) at variable pH in aqueous TBS buffer (10 mM Tris, 150 mM NaCl, pH 8.0), MilliQ water (pH 6.8), or ammonium acetate buffer (20 mM, pH 5.4) at 15° C. The half-lives were 15 h at pH 8.0, 14.2 h at pH 6.8, 49 mins at pH 5.4.

The purified 5-OP-RU was dissolved in aqueous TBS buffer (10 mM Tris, 150 mM NaCl, pH 8.0), MilliQ water (pH 6.8), or aqueous ammonium acetate buffer (20 mM, pH 5.4). The consumption of 5-OP-RU was immediately monitored by LCMS. The initial concentration was quantified by comparing to a standard solution of known concentration. At 15° C., the half-life was determined as 14.5-15 h at pH 8.0 independent of the starting concentrations (65-250 µM), 14.2 h at pH 6.8 (65 µM), and 49 mins at pH 5.4 (65 µM). At 37° C., pH 6.8, the half-life was 135 mins (FIG. 7).

Activation of Jurkat.MAIT and SKW.MAIT Cells and Detection of MR1 Expression on C1R.MR1 Cells Jurkat cells transduced with genes encoding a MAIT TCR comprising the TRAV1-2-TRAJ33 invariant α chain, and a TRBV6-1 β chain, or SKW cells transduced with genes encoding the TRAV1-2-TRAJ33 invariant α chain with either w.t. Tyr95 or mutated Tyr95Ala or Tyr95Phe residues, paired with a TRBV6-1 β chain, were tested for activation by co-incubation with bacterial culture supernatant or compounds and C1R antigen presenting cells expressing MR1 (CIR.MR1, with Jurkat.MAIT cells), or C1R cells (SKW.MAIT cells) for 16 hr. Cells were subsequently stained with PE-Cy7-conjugated anti-CD3 (eBioscience), and APC-conjugated anti-CD69 (BD) antibodies as well as biotinylated anti-MR1 mAb 26.5 (Huang S. et al (2005)), followed by Streptavidin-PE (BD), before analysis by flow cytometry. Activation of Jurkat.MAIT or SKW.MAIT cells was measured by an increase in surface CD69 expression. MR1 expression was detected on gated C1R.MR1 cells in the same assay.

Preparation of Denatured Inclusion Body MR1 and β2m

Genes encoding soluble human MR1 or human β2m were expressed for 4 hr in BL21 E. coli following induction with 1 mM isopropyl β-D-1-thiogalactopyranoside. E. coli were pelleted and resuspended in a buffer containing 50 mM Tris, 25% (w/v) sucrose, 1 mM EDTA, 10 mM DTT pH 8.0. Inclusion body protein was then extracted by lysis of bacteria in a buffer containing 50 mM Tris pH 8.0, 1% (w/v) Triton X-100, 1% (w/v) sodium deoxycholate, 100 mM NaCl, 10 mM DTT, 5 mM MgCl$_2$, and 1 mg DNaseI per liter of starting culture; and subsequent steps involved homogenization with a polytron homogenizer, centrifugation, and washing inclusion body protein sequentially with firstly a buffer containing 50 mM Tris pH 8.0, 0.5% Triton X-100, 100 mM NaCl, 1 mM EDTA, 1 mM DTT, and secondly a buffer containing 50 mM Tris pH 8.0, 1 mM EDTA, 1 mM DTT. Inclusion body protein was then resuspended in a buffer containing 20 mM Tris pH 8.0, 8 M urea, 0.5 mM EDTA, 1 mM DTT, and following centrifugation the supernatant containing solubilized, denatured inclusion body protein was collected and stored at −80° C.

Refolding of MR1-Ligand and MAIT TCR

MR1 (the ectodomain) and β2m were refolded with ligand essentially as described (Kjer-Nielsen L. et al (2012)). Briefly, in order to generate MR1-5-OP-RU and MR1-5-OE-RU, 56 mg of MR1 and 28 mg of β2m inclusion body proteins, together with 2.9 mg of 5-A-RU and 254, 204, or 204 mg of methylglyoxal, glyoxal (Sigma), or $^{13}$C-glycolaldehyde (Omicron) respectively were added to a 400 ml refold solution containing 0.1M Tris, pH 8.5, 2 mM EDTA, 0.4M arginine, 0.5 mM oxidized glutathione and 5 mM reduced glutathione. Refolded MR1-Ag was then purified by sequential DEAE (GE Healthcare) anion exchange, S75 16/60 (GE Healthcare) gel filtration, and MonoQ (GE Healthcare) anion exchange chromatography. Alternatively, 56 mg of MR1 and 28 mg of β2m inclusion body proteins were refolded in the presence of 400 ml of 0.45 µM-filtered bacterial supernatants or control media, in the absence or presence of 204 mg $^{13}$C-glycolaldehyde. The TRBV6-1 MAIT TCR (the ectodomains) was expressed, refolded and purified essentially as previously described (Reandragoon R. et al (2012)).

Sequences of constructs used in refolding are:

Soluble TRAV1-2 α-chain a.a. sequence, excluding the transmembrane/cytoplasmic domains:

MGQNIDQPTEMTATEGAIVQINCTYQTSGFNGLFWYQQHAGEAPTFLSYN

VLDGLEEKGRFSSFLSRSKGYSYLLLKELQMKDSASYLCAVKDSNYQLIW

GAGTKLIIKPDIQNPDPAVYQLRDSKSSDKSVCLFTDFDSQTNVSQSKDS

DVYITDKCVLDMRSMDFKSNSAVAWSNKSDFACANAFNNSIIPEDTFFPS

PESS

Soluble TRBV6-1 β-chain a.a. sequence, excluding the transmembrane/cytoplasmic domains:

MNAGVTQTPKFQVLKTGQSMTLQCAQDMNHNSMYWYRQDPGMGLRLIYYS

ASEGTTDKGEVPNGYNVSRLNKREFSLRLESAAPSQTSVYFCASSVWTGE

GSGELFFGEGSRLTVLEDLKNVFPPEVAVFEPSEAEISHTQKATLVCLAT

GFYPDHVELSWWVNGKEVHSGVCTDPQPLKEQPALNDSRYALSSRLRVSA

TFWQNPRNHFRCQVQFYGLSENDEWTQDRAKPVTQIVSAEAWGRAD

Soluble human MR1 a.a. Sequence, excluding the transmembrane/cytoplasmic domains:

MRTHSLRYFRLGVSDPIHGVPEFISVGYVDSHPITTYDSVTRQKEPRAPW

MAENLAPDHWERYTQLLRGWQQMFKVELKRLQRHYNHSGSHTYQRMIGCE

LLEDGSTTGFLQYAYDGQDFLIFNKDTLSWLAVDNVAHTIKQAWEANQHE

LLYQKNWLEEECIAWLKRFLEYGKDTLQRTEPPLVRVNRKETFPGVTALF

CKAHGFYPPEIYMTWMKNGEEIVQEIDYGDILPSGDGTYQAWASIELDPQ

SSNLYSCHVEHSGVHMVLQVP

Analysis of MR1-5-OP-RU and MR1-5-OE-RU by Mass Spectrometry.

MR1-5-OP-RU or MR1-5-OE-RU (4 Mg) were loaded onto an XBridge C18 reversed phase column (Waters) in 20 mM ammonium acetate, pH 5.4, buffer, and detected in an Agilent ESI-TOF mass spectrometer after elution in an acetonitrile gradient. Data was collected in negative ion mode. Different instrumentation resulted in slight variations in retention times of the m/z 329.11/315.09/317.10 species to that reported previously (Kjer-Nielsen L. et al (2012)).

Generation of MR1-K43A, MR1-5-OP-RU and MR1-5-OE-RU Tetramers

The generation of K43A-MR1 tetramers, loaded with synthetic rRL-6-CH$_2$OH, has been previously described (Reantragoon R. et al (2013)). Briefly, refolded and purified empty C-terminal cysteine-tagged-MR1-K43A was loaded with a 136 molar excess of synthetic rRL-6-CH$_2$OH for 4 hr at room temperature in the dark. C-terminal cysteine-tagged wild type MR1-5-OP-RU and MR1-5-OE-RU were generated as described above.

Cysteine-tagged-K43A-MR1-5-OP-RU, or cysteine-tagged w.t. MR1-5-OP-RU or cysteine-tagged w.t. MR1-5-OE-RU were then reduced with 5 mM DTT for 20 min prior to buffer exchange into PBS using a PD-10 column (GE Healthcare), and biotinylated with Maleimide-PEG2 biotin (Thermoscientific) with a 30:1 molar ratio of biotin:protein at 4° C. for 16 hr in the dark. Biotinylated MR1 was subjected to S200 10/300 GL (GE Healthcare) chromatography to remove excess biotin. Biotinylated, loaded K43A-MR1, or w.t. MR1-5-OP-RU or w.t. MR1-5-OE-RU monomers were tetramerized with streptavidin conjugated to either PE (SA-PE) or Brilliant Violet 421 (SA-BV) (BD Pharmingen).

Isolation of PBMCs

Whole blood from healthy donors was collected (Australian Red Cross Blood Service) and peripheral blood mononuclear cells were separated using Ficoll-Paque Premium (GE Healthcare). PBMCs were harvested and resuspended in fresh RPMI medium. Cells were then washed twice prior to resuspension in 10% DMSO in FCS. Prior to use, PBMCS were stored in liquid nitrogen.

Tetramer Staining of Human PBMCs.

For co-staining with wild-type and K43A-MR1 tetramers, approximately $5\times10^5$ human PBMCs were stained with K43A-MR1-5-OP-RU-PE tetramer at 20 µg/ml for 40 minutes at room temperature in the dark. Cells were then washed and stained with w.t. MR1-5-OP-RU-BV tetramer at 1.4 µg/ml, CD3-AlexaFluor700 (EBioscience), CD161-PE-Cy7 (Biolegend), CD4-APC-Cy7 (Biolegend) and CD8α-PerCp-Cy5.5 (BD) for 30 minutes at 4° C. Cells were then washed once with 2 ml of FACS wash (2% fetal bovine serum in PBS) and resuspended in 150 µl of FACS fix (2% glucose and 1% paraformaldehyde in PBS) prior to acquisition of data on a BD LSR-Fortessa. Data were analyzed using FlowJo analysis software (Tree Star, Ashland, Oreg.).

For single staining with either MR1-5-OP-RU or MR1-5-OE-RU tetramers, human PBMCs were stained as above with w.t. MR1-5-OP-RU-PE or w.t. MR1-5-OE-RU-PE tetramers at 1.4 ug/ml, and CD3-AlexaFluor700 (EBioscience), CD161-PE-Cy7 (Biolegend), CD4-APC-Cy7 (Biolegend) and CD8α-PerCp-Cy5.5 (BD) for 30 minutes at 4° C., prior to acquisition of data on a BD LSR-Fortessa.

Crystallization and Structure Determination

Crystals of the soluble MAIT TCR-MR1-Ag complexes were obtained using the hanging drop vapour diffusion method. The MR1-$_2$M-5-OP-RU, MR1-$_2$M-5-OE-RU, MR1, MR1-K43A-$_2$M-5-OP-RU and MAIT TCR were concentrated to 4 mg/ml, mixed in a 1:1 molar ratio, then 0.5 l added to 0.5 l of a precipitant solution consisting 0.1 M bis-tris propane pH 6.3, 0.2 M sodium acetate and varying concentrations of PEG 3350 between 8-14% w/v. Crystals were observed after incubation at 20° C. for 24 hours in dark conditions and cryoprotected prior to diffraction experiments by soaking in the crystallisation condition modified with between 10-15% v/v glycerol before cooling to 100K. Diffraction images were collected at the Australian Synchrotron MX2 beamline diffracting in a C2 spacegroup to 2.50 Å, 2.10 Å and 2.20 Å for the MR1-$_2$M-5-OP-RU, MR1-$_2$M-5-OE-RU, and MR1-K43A-$_2$M-5-OP-RU complexes with the MAIT TCR respectively. The data were processed using Mosflm version 7.0.9 and scaled using AIMLESS or SCALA (MR1-K43A-$_2$M-5-OP-RU only) from the CCP4 Suite. The phase problem was solved by molecular replacement using PHASER (McCoy A. J. (2007)), using MR1 ternary complex (PDB code 4L4T) (Patel O. et al (2013)) with CDR loops and ligands removed and using the R$_{free}$ reflection set from the model. The initial solution was refined in Phenix using simulated annealing refinement, with all subsequent refinement steps performed using BUSTER 2.10 (Zwart P. H. et al (2008)). Restraints for 5-OP-RU and 5-OE-RU were generated using the Grade Web Server, with model building performed in COOT using MolProbity for validation (Emsley P. & Cowtan K. (2004)). All molecular graphics were made with PyMOL.

Example 1

MAIT cell antigens were previously identified from *Salmonella typhimurium* (strain SL1344) supernatant (Kjer-Nielsen L. et al (2012)). Negative mode electrospray ionization-time-of-flight mass spectrometry (ESI-TOF-MS) analysis of MR1-bound ligands from *S. typhimurium* revealed a ligand with a mass to charge (m/z) ratio of 329.11, matching a potent MAIT activating ligand identified during the chemical synthesis of reduced 6-hydroxymethyl-8-D-ribityllumazine (rRL-6-CH$_2$OH) (Kjer-Nielsen L. et al (2012)). While this ligand was identified biochemically, its origin was puzzling, as it is not described in the riboflavin synthesis pathway. A genetic approach was taken to evaluate if the riboflavin pathway supplied the MAIT cell ligands.

The capacity of bacterial mutants of the riboflavin pathway to activate MAIT cells (FIG. 1a) was examined. In some bacterial species, including *Lactococcus lactis*, the genes necessary for riboflavin synthesis are grouped together in a single 4-gene operon (RibGBAH), and are regulated by transcriptional repression of a "riboswitch" via flavin mononucleotide and riboflavin (Citreschak A. G. et al (2004)). Using *L. lactis*, we tested the ability of bacterial culture supernatant to activate Jurkat cells transduced with a MAIT TCR (Jurkat.MAIT) (FIG. 1b) was tested. Supernatant from wild type *L. lactis* strain NZ9000 incubated with Ag presenting cells expressing MR1 caused CD69 upregulation in Jurkat.MAIT cells (FIG. 1b). Addition of riboflavin during culture of NZ9000 inhibited MAIT cell activation consistent with negative regulation of the riboswitch and impaired production of the activating MAIT ligand (FIG. 1b). Next, three mutant strains of *L. lactis* were employed: two riboflavin overproducers, CB013 and CB021, which produce riboflavin even in the presence of high riboflavin concentrations, and a RibA-strain, which contains a deletion in ribA, early in the riboflavin pathway (Burgess C et al (2004)). The riboflavin overproducers activated Jurkat. MAIT cells when grown with or without exogenous riboflavin, whilst there was no MAIT cell activation by supernatant from the RibA-strain (FIG. 1b).

Figure 5:
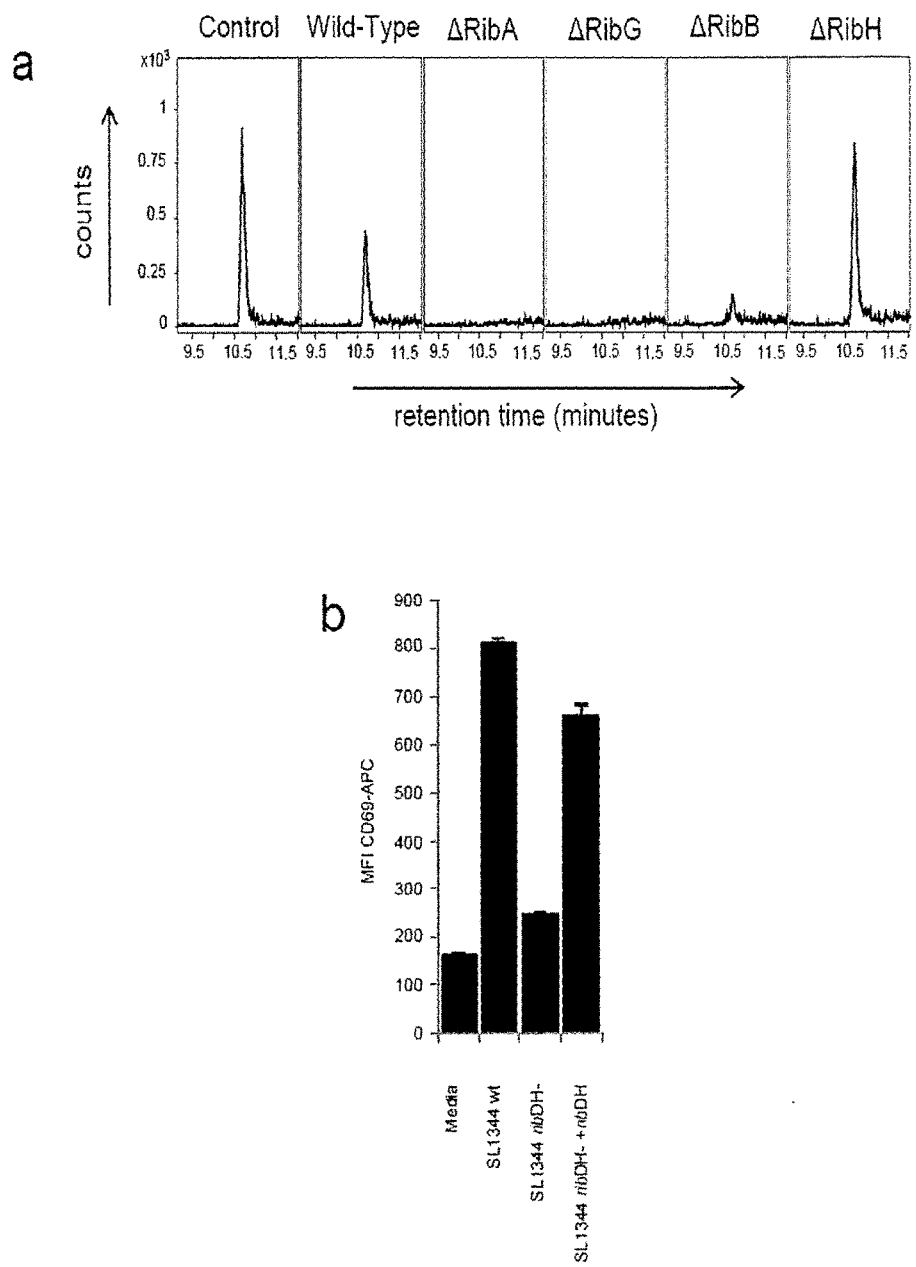
FIG. 5 is a graph showing MR1 ligand identification from different bacterial strains (a) Detection of m/z 329.11 species in MR1 refolded with 5-A-RU and methylglyoxal (Control), and supernatants from wild-type (CB013), and CB013-derivatives (i.e. RibA, RibB, RibG, or RibH) *L. lactis* bacteria. Shown are counts on the Y-axis versus retention time on the X-axis. (b) Lack of activation of Jurkat.MAIT cells by supernatant from mutant RibD/H *S. typhimurium* (strain SL1344) but not. wild-type (wt), or RibD/H+RibD/H bacteria. Shown is MFI of CD69.APC on the Y-axis. (c) Detection of m/z 329.11 species in MR1 refolded with supernatants from wild type, RibD/H, or RibD/H+RibD/H *S. typhimurium* bacteria, or control media. Shown are counts on the Y-axis versus retention time on the X-axis. (d) Detection of m/z 329.11 species in MR1 refolded with 5-A-RU and methylglyoxal (Control), or bacterial supernatants from *L. lactis* (CBO13) or *E. faecalis* bacteria, or control media. Shown are counts on the Y-axis versus retention time on the X-axis. (e) Detection of m/z 329.11 species in MR1 refolded with 5-A-RU and methylglyoxal (Control), or supernatant from *E. coli* bacteria, or media. Shown are counts on the Y-axis versus retention time on the X-axis. Experiments a-e were performed three, three, three, two and three times respectively.
Figure 5:
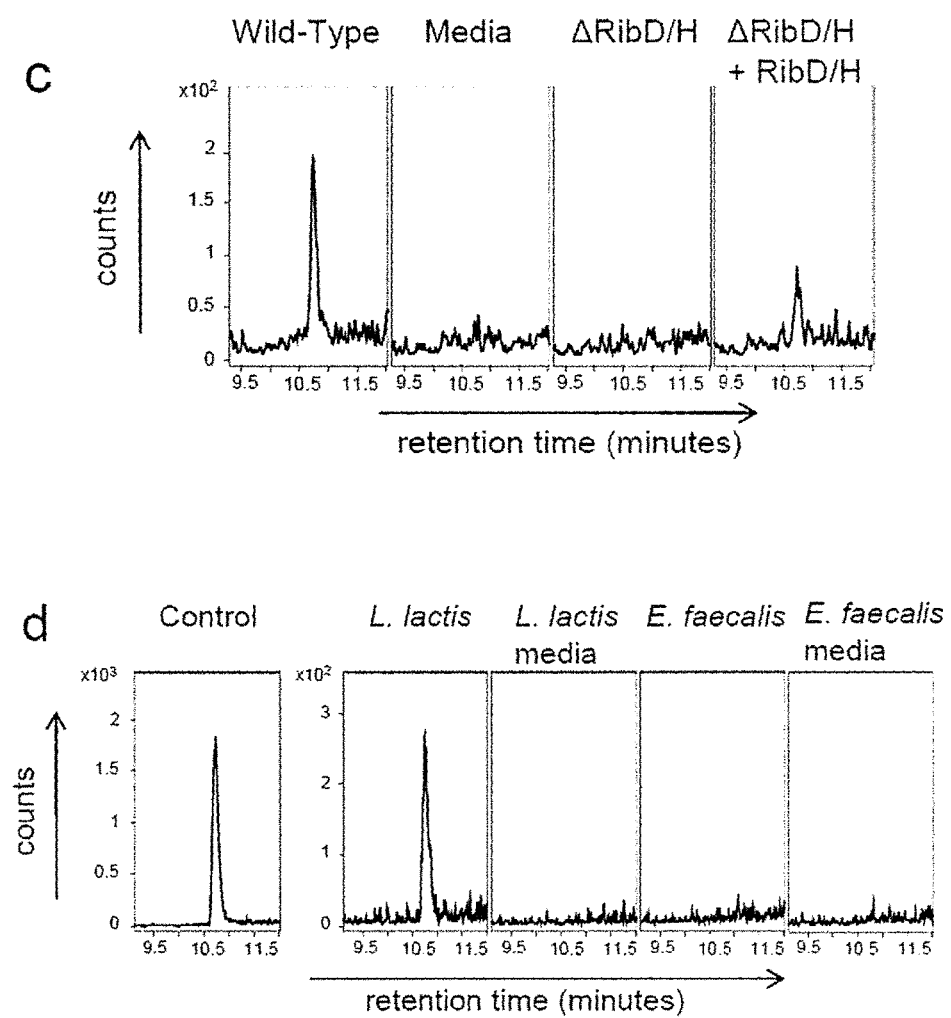
Figure 5:
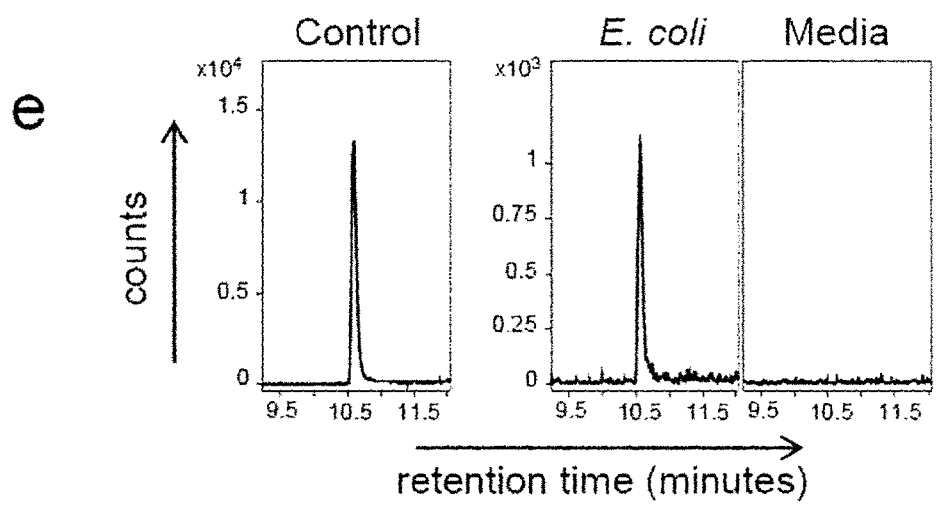

Next individual mutations in the four genes of the riboflavin operon in *L. lactis* were generated. These were produced using the constitutive riboflavin overproducer strain CB013. Culture supernatants from bacteria with mutant riboflavin pathways were tested for activation of Jurkat. MAIT cells (FIG. 1c). The parental CB013 supernatant activated Jurkat.MAIT cells whereas bacteria containing mutations in RibA or RibG did not activate the reporter cells under similar conditions (FIG. 1c). Neither RibB nor RibH mutations, which affect the pathway downstream of 5-amino-6-D-ribitylaminouracil (5-A-RU), had any impact on Jurkat.MAIT activation (FIG. 1c). Moreover, while the m/z 329.11 species was undetectable in MR1 refolded with supernatant from the RibA and RibG mutants, it was captured by MR1 from the supernatants of the RibB and RibH mutants of *L. lactis* (FIG. 5). Moreover, culture supernatants from *S. typhimurium* SL1344 with mutated RibD+H did not furnish a detectable m/z 329.11 species that bound MR1, and could not activate Jurkat.MAIT cells (FIGS. 5b-c). However, Ag was detectable in the complemented, activating RibD+H SL1344 mutant (FIG. 5b-c). MR1-restricted ligands were not detected from the supernatant of *Enterococcus faecalis*, which neither possesses the riboflavin pathway nor activates MAIT cells (FIG. 5d and not shown). Analysis of MR1-bound ligands from another MAIT activating strain, *Escherichia coli* (DH5α strain) also revealed a ligand with a mass to charge (m/z) ratio of 329.11 (FIG. 5e). These data are consistent with MAIT activating ligands, from a number of bacterial sources, being derived via an unknown mechanism from 5-A-RU.

Figure 11:
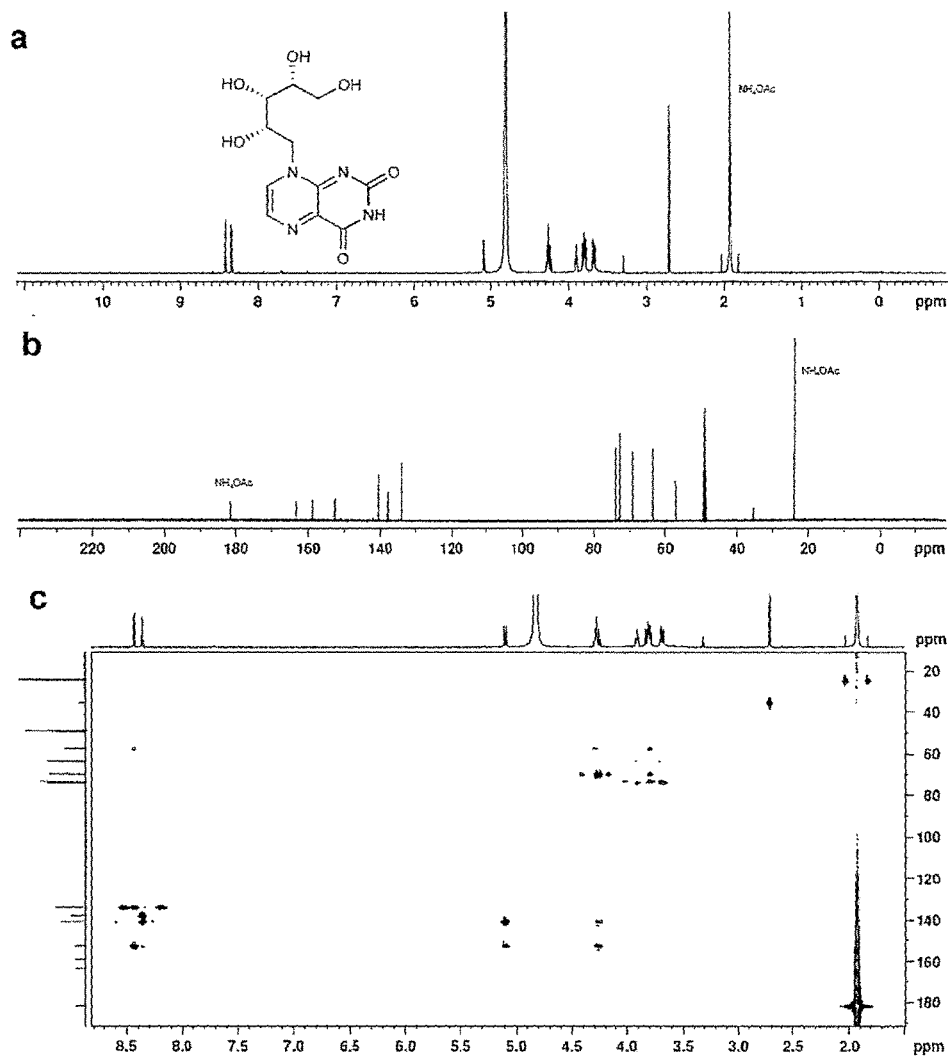
FIG. 11 is a graph showing NMR characterization of 8-D-ribityllumazine (RL). Spectra were recorded as a solution in $D_2O$—$CD_3OD$ (9:1) with internal solvent peak at 3.31 ppm and 49.0 ppm for $^1$H and $^{13}$C, respectively. (a) $^1$H NMR (600 MHz); (b) $^{13}$C NMR (150 MHz); (c) HMBC.
Figure 12:
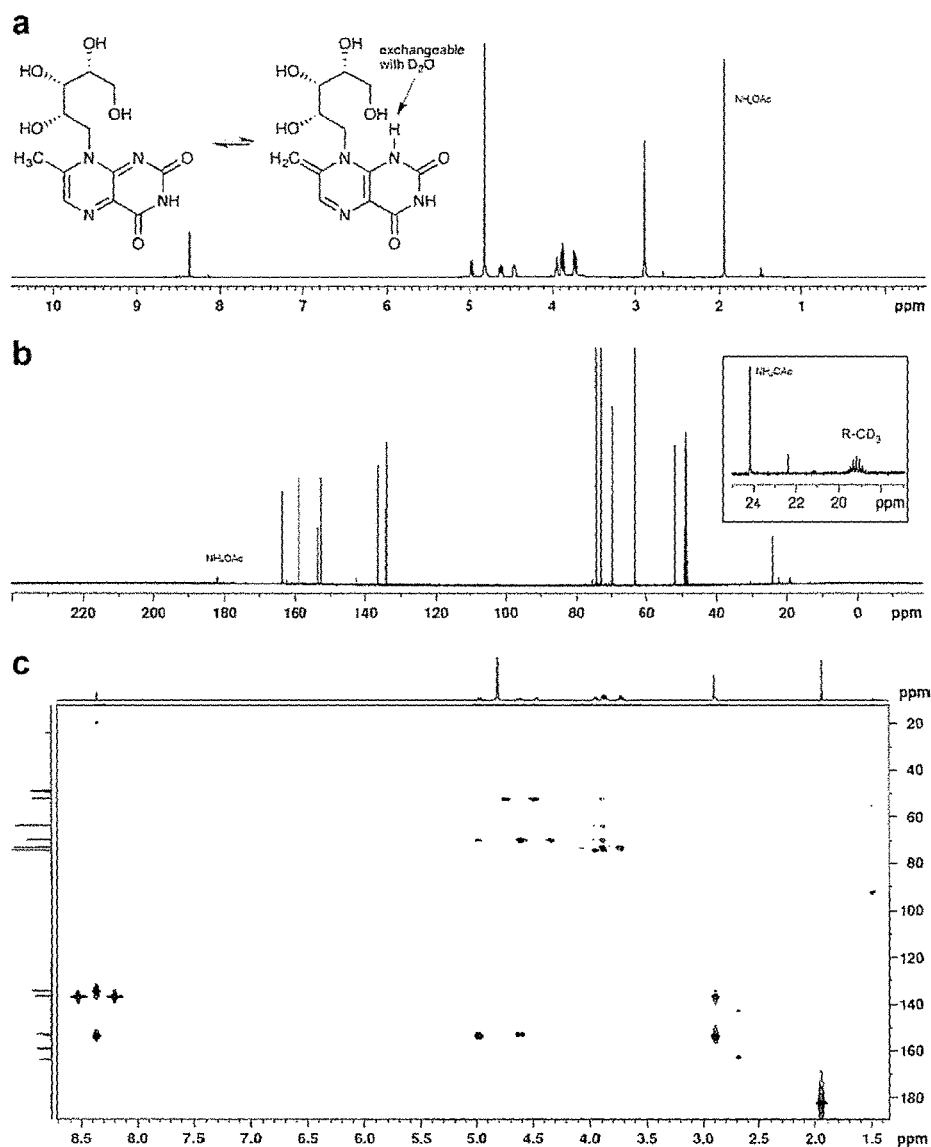
FIG. 12 is a graph showing NMR characterization of 7-methyl-8-D-ribityllumazine (RL-7-Me). Spectra were recorded as a solution in $D_2O$—$CD_3OD$ (9:1) with internal solvent peak at 3.31 ppm and 49.0 ppm for $^1$H and $^{13}$C, respectively. (a) $^1$H NMR (600 MHz) and mechanism for deuterium exchange of $CH_3$ at position-7. Identical exchange was also observed in pure $D_2O$ at slower rate (not shown); (b) $^{13}$C NMR (150 MHz) showing characteristic heptet from 7-$CD_3$ after complete deuterium exchange; (c) HMBC.

A key precursor step in riboflavin biosynthesis is the condensation of 5-A-RU (1) with 3,4-dihydroxy-2-butanone-4-phosphate (2a) to generate an intermediate 5-(1-methyl-2-oxopropylideneamino)-6-D-ribitylaminouracil (5-MOP-RU, 3a), which ring closes readily with dehydration to form RL-6,7-DiMe (4a) (Cushman M. et al (2002); Bacher A. et al (2000)) (FIG. 2a), a biosynthesis that is catalysed by lumazine synthase (RibH). However, RL-6,7-DiMe can also be generated in the absence of lumazine synthase (Bacher A. et al (2000); Kis K. et al (2001)), suggesting that MAIT antigens might be formed through spontaneous reactions of 5-A-RU with other small molecules via non-enzymatic mechanisms (FIG. 2a). For example, butane-2,3-dione (2b), glyoxal (2c) and methylglyoxal (pyruvaldehyde, 2d) can represent by-products arising from a number of metabolic pathways, including glycolysis (Wang Y & Ho C.-T. (2012)). Their condensations with 5-A-RU (1) would respectively produce pyrimidine adducts 5-MOP-RU (3b=3a), 5-OE-RU (3c) and 5-OP-RU (3d) en route to ribityllumazines RL-6,7-DiMe (4b=4a), RL (4c) and RL-7-Me (4d) respectively. We found that the initial adducts 3b-d were formed almost immediately, but readily undergo dehydration upon ring closure to very stable, isolatable compounds 4a-d (FIGS. 11 and 12), without the need for enzyme catalysis. Adducts 3a-d (FIG. 2a) were especially unstable under acidic aqueous conditions (pH<6), but we could detect them in solution under physiological conditions. 3d was able to be synthesised in DMSO-$d_6$, isolated and its solution structure unambiguously assigned by NMR spectroscopy (FIG. 2b & FIG. 6), and its stability in aqueous media using LCMS examined. At 37° C. and pH 6.8, adduct 3d was clearly formed and had a half-life of around 2 h at 65 μM. It was more stable at lower temperature (e.g. $t_{1/2}$ 14-15 h, 15° C., pH 6.8-8.0, 65-250 μM) (FIG. 7).

Figure 3:
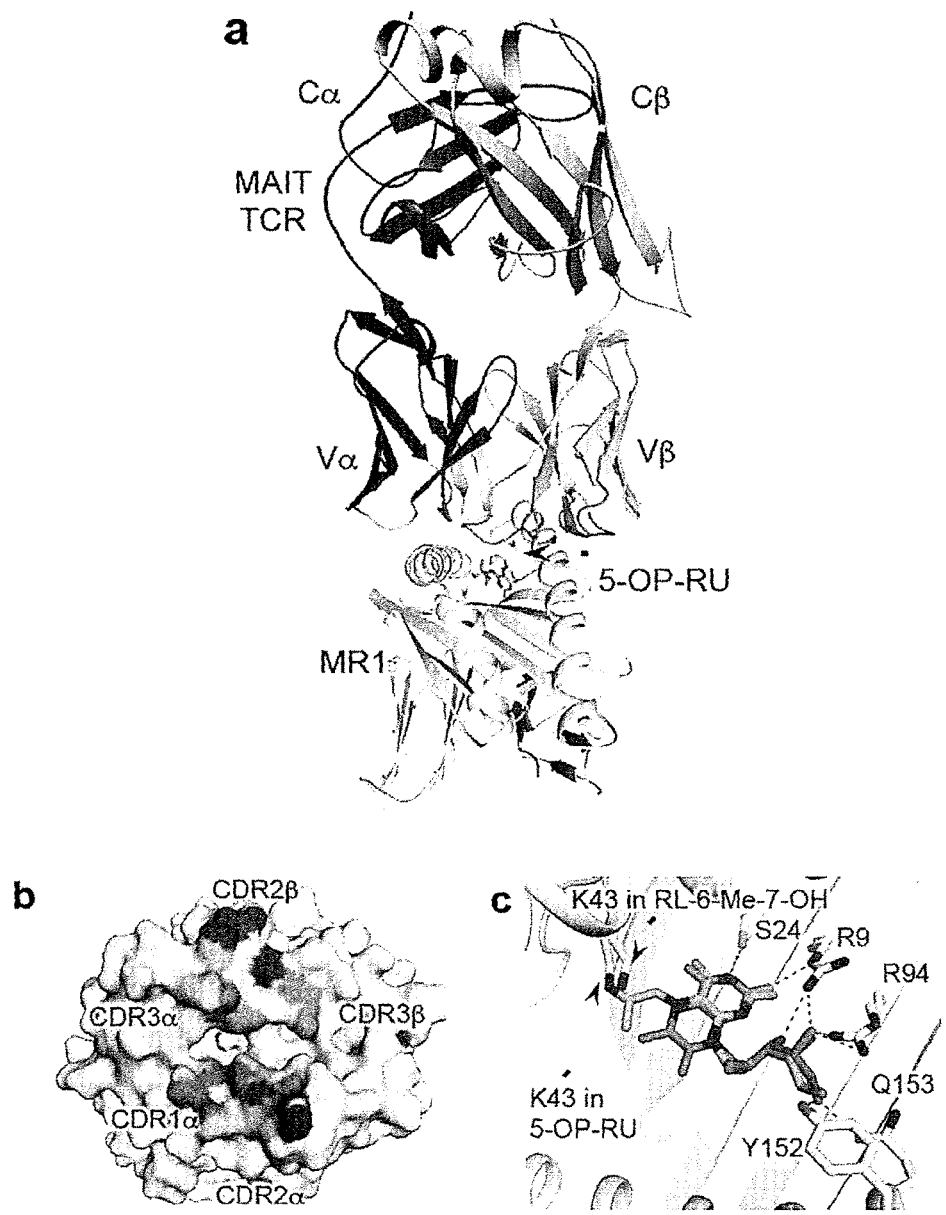
FIG. 3 is a schematic showing structural basis of MR1-binding and recognition of transitory MAIT cell antigens (a) MAIT TCR-MR1-Ag docking, (b) MAIT TCR footprint on MR1 surface (c) 5-OP-RU and 7-hydroxy-6-methyl-8-D-ribityllumazine RL-6-Me-7-OH overlay; MR1 contacting (d) 5-OP-RU and (e) 5-OE-RU; MAIT TCR contacting (f) RL-6-Me-7-OH, (g) 5-OP-RU or (h) 5-OE-RU. MR1 (grey), -chain (purple), -chain (cyan). 5-OP-RU (green), 5-OE-RU (yellow) and RL-6-Me-7-OH (magenta), CDR1 (slate), CDR2 (pink), CDR3 (yellow), CDR1 (teal), CDR2 (red) and CDR3 (orange).
Figure 3:
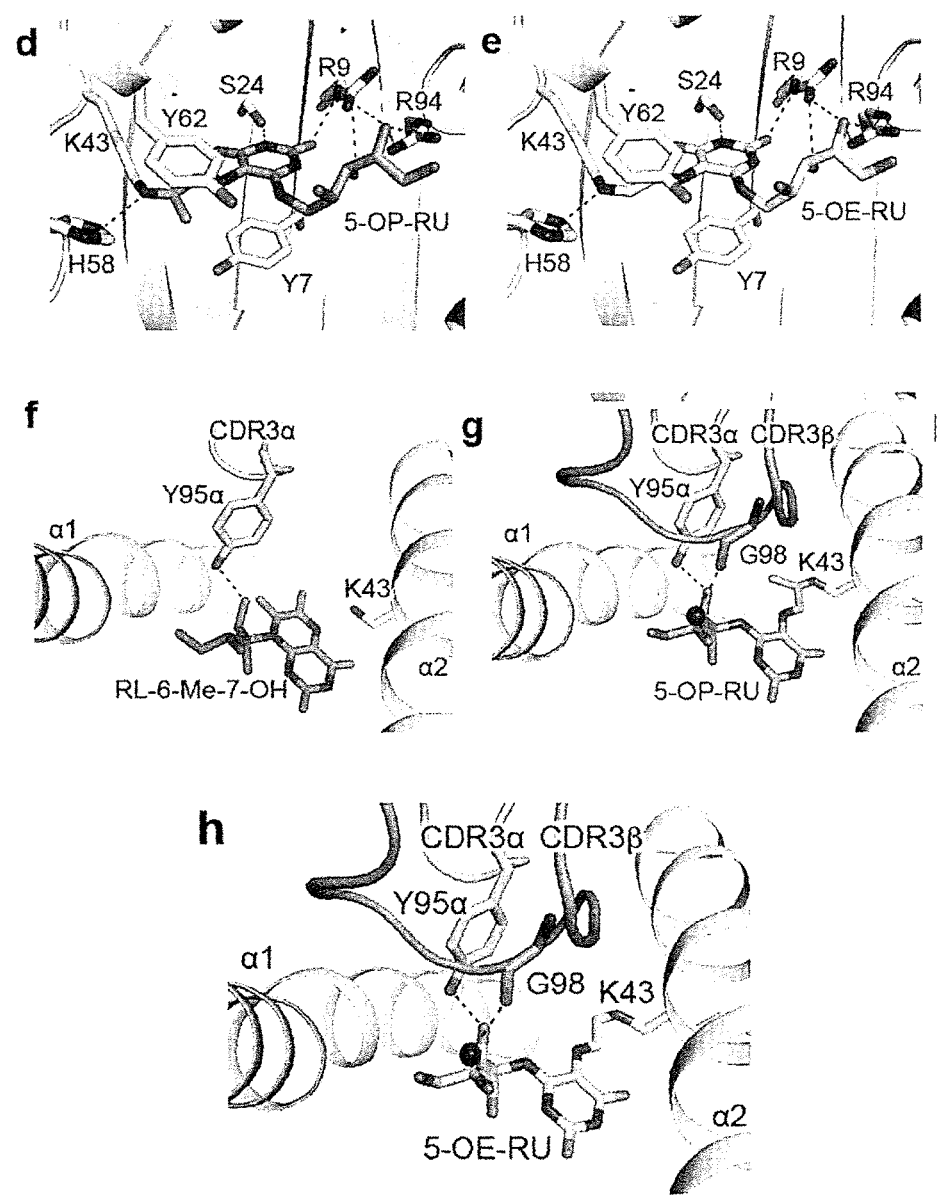
Figure 8:
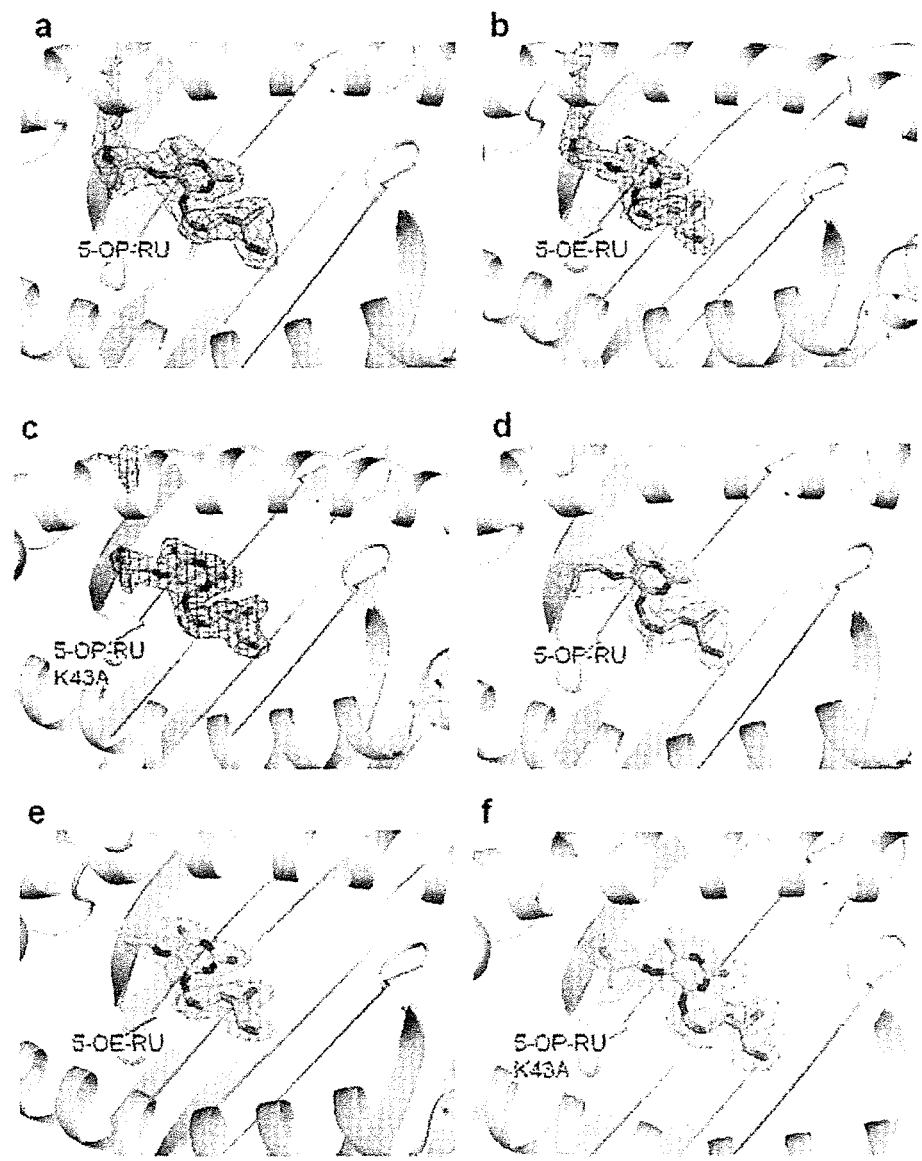
FIG. 8 is a schematic showing electron density for ligands, and associated contacts. Electron density of 5-OP-RU in MR1, 5-OE-RU in MR1 and 5-OP-RU in K43A-MR1. Final $2F_o-F_c$ map, contoured at 1 for (a) 5-OP-RU, (b) 5-OE-RU in the MAIT TCR-MR1Ag complex and (c) 5-OP-RU in the MAIT TCR-MR1-K43A-Ag complex. Simulated annealing omit maps showing unbiased $F_o-F_c$ electron density, contoured at 3, for (d) 5-OP-RU and (e) 5-OE-RU in MR1 and (f) 5-OP-RU in MR1-K43A. MR1-K43A-5-OP-RU MAIT TCR complex showing contacts between MR1-K43A and (g) 5-OP-RU and contacts between MAIT TCR and (h) 5-OP-RU. MR1 is shown in grey and MAIT TCR CDR3 in yellow in and CDR3 in orange with ribbon representation and 5-OP-RU in cyan with stick representation. Hydrogen bonds are indicated with black dashed lines with a water molecule mediating hydrogen bonding between the CDR3 5-OP-RU shown in dark blue sphere representation.
Figure 8:
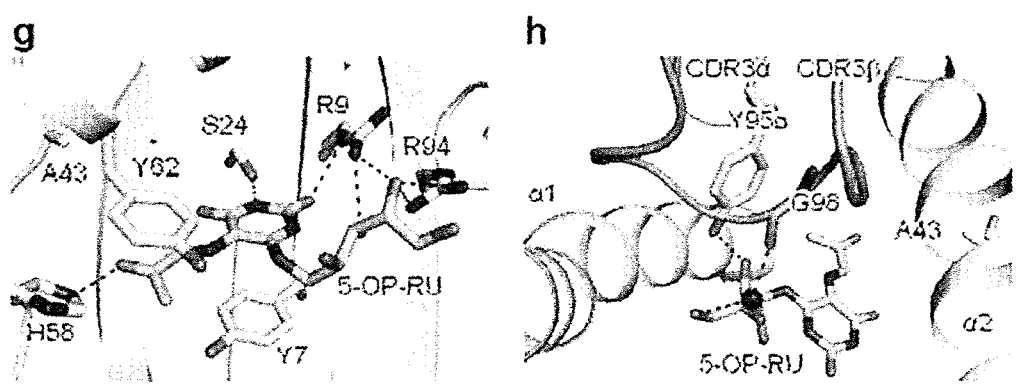

MR1-5-A-RU was undetectable when MR1 was refolded with 5-A-RU alone (not shown), and the presence of 5-A-RU and butane-2,3-dione failed to yield any MR1-Ag complexes (not shown). However, refolding of MR1 in the presence of 5-A-RU and either glyoxal or methylglyoxal led to a correctly folded MR1-Ag complex. To understand the basis for ligand selectivity by MR1, the structures of the MAIT TCR in complex with MR1 and Ags formed from the condensation of 5-A-RU and either methylglyoxal or glyoxal were determined (FIGS. 3a-h, FIG. 13 & FIG. 8) (Patel O. et al (2013)). The chemically unstable adducts 5-(2-oxopropylideneamino)-6-D-ribitylaminouracil (5-OP-RU, compound 3d, FIG. 2a) and 5-(2-oxoethyllideneamino)-6-D-ribitylaminouracil (5-OE-RU, compound 3c, FIG. 2a) were observed bound to MR1 (FIG. 8, FIGS. 3d & 3e). Both of these one-ring (pyrimidine) compounds were thus captured by MR1, despite being relatively unstable in the absence of MR1 and readily undergoing dehydrative cyclization to compounds 4d and 4c, respectively. The aromatic pyrimidine ring systems of 5-OP-RU and 5-OE-RU superposed on the corresponding ring from the bicyclic lumazine RL-6-Me-7-OH[16] (FIG. 3c). The creation of 5-OP-RU or 5-OE-RU generated an aliphatic moiety that burrowed into the MR1 cleft, within which the residual carbonyl group formed a Schiff base with Lys43 of MR1 (FIGS. 3d & 3e). This aliphatic moiety was also stabilised in the cleft by interactions with Tyr7 and Tyr62 (FIGS. 3d & 3e). In contrast, RL-6-Me-7-OH was non-covalently bound within MR1 (FIG. 3f). Moreover, RL-6-Me-7-OH does not have the propensity to tautomerise into a single ring pyrimidine system due to its ability to form a very stable amide-tautomer. Nevertheless, the ribityl moieties of 5-OP-RU, 5-OE-RU and RL-6-Me-7-OH were all located in essentially identical positions within their respective complexes, each forming a hydrogen bond to Tyr95α of the MAIT TCR (Patel O. et al (2013)) (FIGS. 3f, 3g & 3h). Notably, 5-OP-RU and 5-OE-RU are relatively unstable in aqueous media and thus MR1 can capture and stabilise pyrimidine intermediates in the synthesis of lumazines.

ESI-TOF-MS to independently identify the chemical composition of the ligands captured within these refolded MR1-Ag complexes was undertaken. For MR1 refolded with 5-A-RU and methylglyoxal, a single peak with retention time of 8.9 minutes and m/z 329.11 matched a species that was captured by MR1 from *Salmonella* supernatant and from the reaction mixture during synthesis of rRL-6-CH$_2$OH (FIG. 9a, upper set of panels, Extended data FIG. 5b, upper set of panels). This finding is consistent with the identification within the crystal structure with MR1 of 5-OP-RU, independently assembled from 5-A-RU and methylglyoxal (FIG. 3d), and supported by the NMR and kinetic characterisation of 5-OP-RU in solution (FIG. 2b, FIG. 6.7). Similarly mass spectrometric analysis of MR1 refolded with the mixture of 5-A-RU and glyoxal revealed precursor and product m/z values (FIG. 9a, middle set of panels; FIG. 9b, lower set of panels) consistent with identification of 5-OE-RU within the crystal structure of MR1 refolded with 5-A-RU and glyoxal (FIGS. 3e, 3h). Furthermore, mass spectrometric analysis of MR1 refolded with 5-A-RU and $^{13}$C-labeled glycolaldehyde yielded expected m/z 317.10 precursor and 179.04 product ions, in agreement with the m/z 315.09 precursor and 177.04 product ions identified in MR1 refolded with 5-A-RU and glyoxal (FIG. 9a, lower set of panels; FIG. 9b, lower set of panels).

Figure 4:
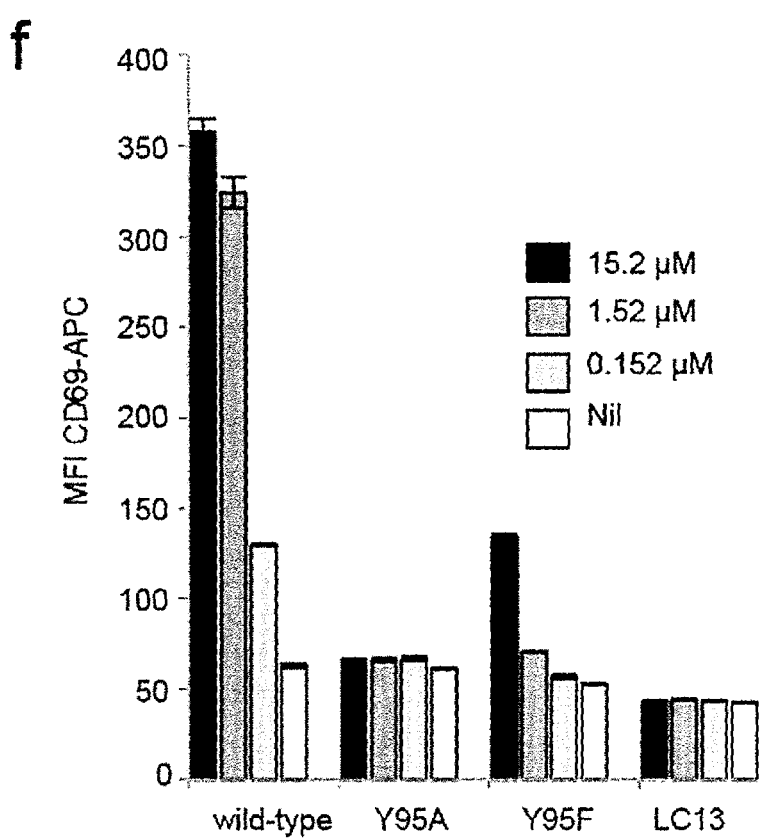
FIG. 4 is a graph showing MR1-Ag tetramers and MAIT activation. (a) Gating strategy (left), tetramers of MR1-6-FP, MR1-5-OP-RU, MR1-5-OE-RU, or anti-TRAV1-2 (b) PBMC co-staining with MR1-5-OP-RU and K43A-MR1-5-OP-RU tetramers. (c) EICs of m/z 315.09, or m/z 317.10. (d) (i) Activation assay and (ii) MR1 upregulation with 5-A-RU, methylglyoxal (MG), butane-2,3-dione (BD), glyoxal (G), or rRL-6-CH$_2$OH. MFI of 26.5-PE antibody staining (e) (i) CD69 upregulation and (ii) MR1 upregulation with 5-A-RU, MG, BD, or G. MFI of 26.5-PE. (f) Activation of wild-type, Y95A, or Y95F mutant SKW.MAIT cells by 5-A-RU. Mean of triplicates with SEM. Experiments were performed at least twice (b, c, f) or 3 times (a, d, e).

Whether the activity with synthetic rRL-6-CH$_2$OH, might reflect capture by MR1 of a synthetic intermediate was evaluated. The ligand captured by the mutant K43A-MR1 exposed to the reaction mixture generating rRL-6-CH$_2$OH was identical by LCMS and MS/MS analysis (m/z 329.11) to the MR1-bound Ag from either *Salmonella* supernatant or derived from 5-A-RU/methylglyoxal condensation (data not shown, FIG. 9a). Whether the respective MR1-tetramers formed from these distinct synthetic Ags were similar functionally was evaluated. MR1-5-OP-RU and MR1-5-OE-RU tetramers efficiently stained all human MAIT cells present in PBMCs similarly to the mutant K43A-MR1 tetramers (Reantragoon R. et al (2013)) (FIGS. 4a & 4b). We solved the crystal structure of the MAIT TCR-K43A-MR1-Ag complex, which revealed 5-OP-RU as the ligand bound to K43A-MR1, indicating that MR1 captures an intermediate from the synthesis of rRL-6-CH$_2$OH (FIG. 8, FIG. 13). Thus active MAIT cell ligands are intermediary, open-ring precursors to ribityllumazines that arise from condensing 5-A-RU with small molecule metabolites.

Figure 10:
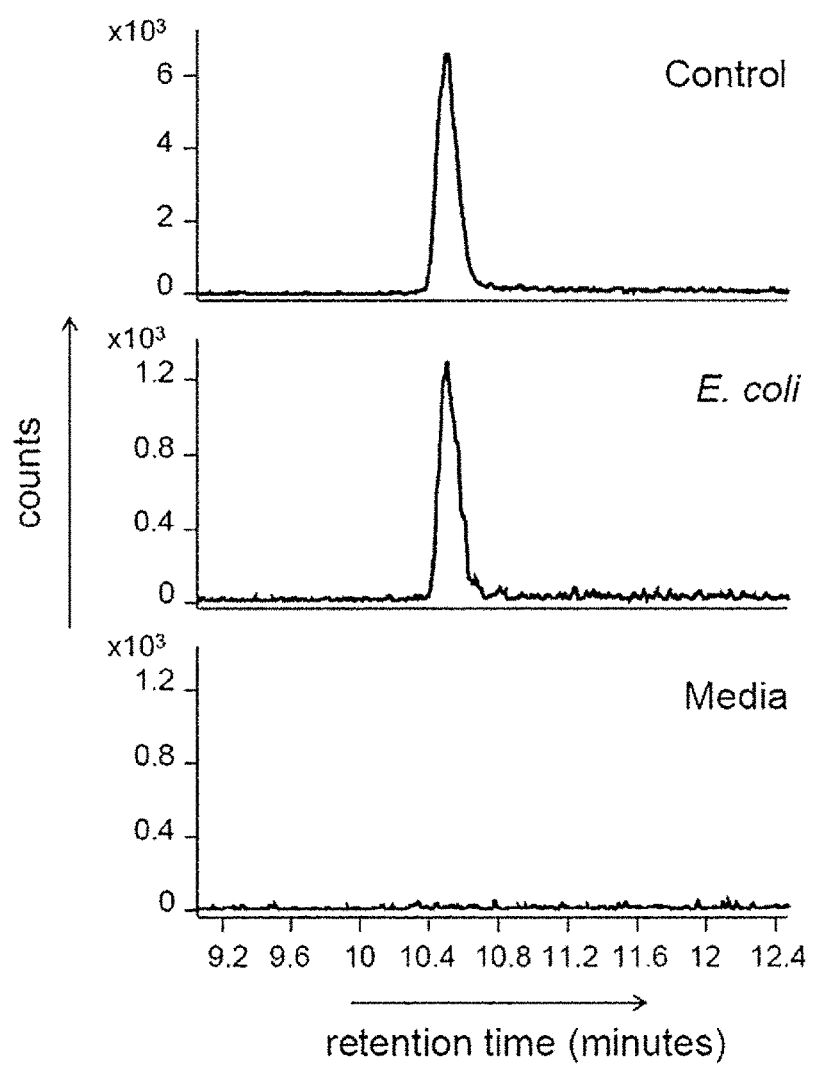
FIG. 10 is a graph showing mass spectrometry of the 315.09 species. Extracted ion chromatograms of m/z 315.09 species in MR1 refolded with 5-A-RU and glyoxal (Control), or E. coli supernatant, or media. Shown are counts on the Y-axis versus retention time on the X-axis. This experiment was performed three times.

Recombinant MR1 refolded in the presence of folate-deficient culture supernatant from *Salmonella typhimurium* (strain SL1344) captured a dominant species of m/z 329.11. Mass spectrometry of MR1 refolded with supernatant from *E. coli* (DH5) also revealed a distinct and abundant m/z 315.09 species with matching liquid chromatography retention time, MS and MS/MS properties to those observed with MR1-5-OE-RU (FIG. 10 and data not shown). Closer analysis of the MR1-eluate from *S. typhimurium* also revealed the presence of a m/z 315.09 species, albeit this ligand was much less prevalent (data not shown). Accordingly bacteria with an active riboflavin pathway can produce distinct MAIT activating ligands, the relative abundance of which is dependent upon the bacterial source.

Figure 9:
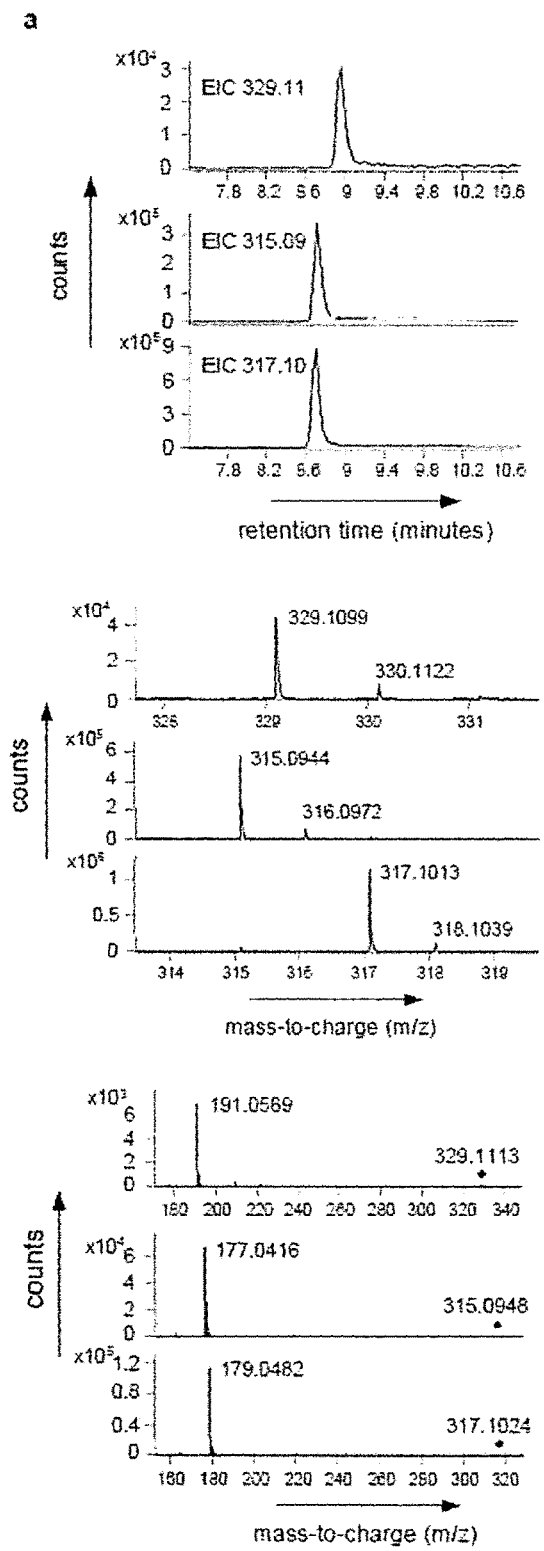
FIG. 9 is a graph and schematic showing chromatographic and mass spectrometry properties of MR1 ligands. (a) Ligand eluted from MR1 complexed with product of (i) 5-A-RU and methylglyoxal condensation reaction (upper panels); (ii) 5-A-RU and glyoxal condensation reaction (middle panels) or 5-A-RU and $^{13}$C-glycolaldehyde condensation reaction (bottom panels). Shown are extracted ion chromatograms (left); mass-to-charge (m/z) spectrum (centre); and product ions from targeted fragmentation (right). Black diamonds: precursor ions. This experiment was performed three times (b) Mass spectrometry characterisation of 5-OP-RU (upper) and 5-OE-RU and $^{13}$C-5-OE-RU (lower).
Figure 9:
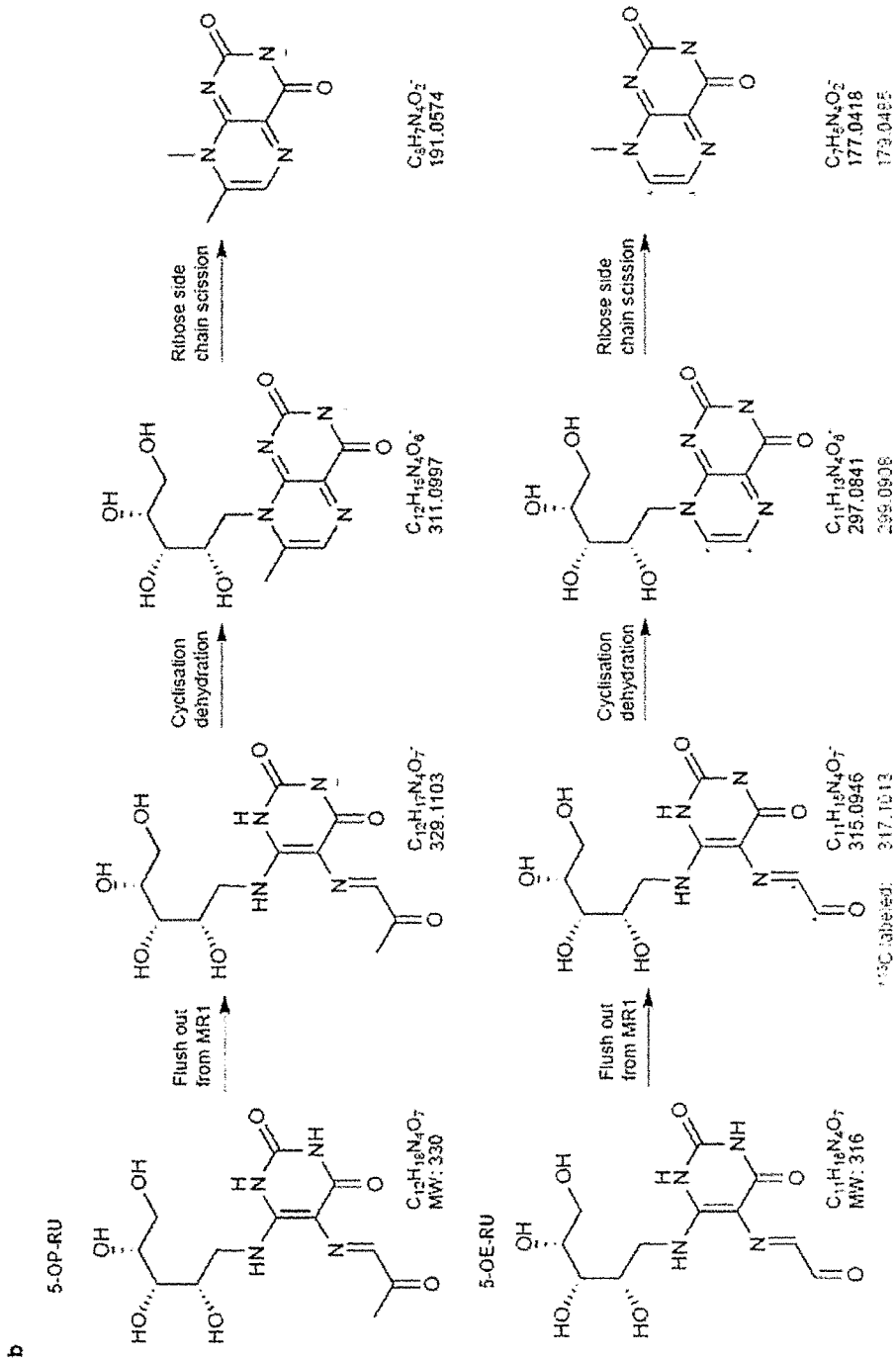

Next, to establish if bacteria also produced free 5-A-RU, $^{13}$C-labelled glycolaldehyde was added to *E. coli* supernatant, which was subsequently refolded with MR1. We detected a species with a m/z of 317.1 from these MR1 eluates (FIG. 4c), consistent with the m/z 317.1 species observed previously (FIG. 9, lower set of panels). This indicates that there is sufficient free 5-A-RU released by bacteria to conjugate with exogenously added metabolites. Potent MAIT cell Ags could also potentially be generated by host-derived metabolites forming adducts with 5-A-RU, in a manner somewhat analogous to the genesis of a CD1b-restricted antigen. To test this, 5-A-RU to C1R cells transduced with MR1 (C1R.MR1) was added, which led to MR1 cell surface upregulation and activation of Jurkat.MAIT cells (FIGS. 4d & 4e). When exogenous glyoxal or methylglyoxal were added with 5-A-RU to C1R.MR1 cells, a further increase in MR1 upregulation and an increase in Jurkat.MAIT activation was observed, when compared to 5-A-RU added by itself (FIGS. 4d & 4e). Notably, MR1 surface expression was not enhanced, nor was there an increase in Jurkat.MAIT activation, upon co-addition of butane-2,3-dione with 5-A-RU (FIGS. 4d & 4e). These observations suggest that MR1-Ag complexes created from 5-A-RU and glyoxal or methylglyoxal are natively conformed. To test this, the mutation of Tyr95α to either Ala95 or Phe95 ablated recognition of C1R cells to which 5-A-RU had been added, in a manner similar to that observed when synthetic rRL-6-CH$_2$OH was added to C1R cells, consistent with the notion that 5-A-RU is converted to 5-OE-RU or 5-OP-RU within C1R Ag presenting cells (FIG. 4f). Accordingly, the bacterial riboflavin metabolite, 5-A-RU, can interact with host-derived metabolites analogous functionally to the creation of MR1 ligands found in bacterial supernatant.

Example 2

MAIT cell detection in histological sections (using mAb D5, which co staining with tetramer shown in Reantragoon et al (2013) shows identifies MAIT cells) shows a correlation between MAIT cell numbers and *helicobacter* infection in human gastric biopsies (obtained through collaboration with Andy Giraud, MCRI) (FIG. 14).

Figure 15:
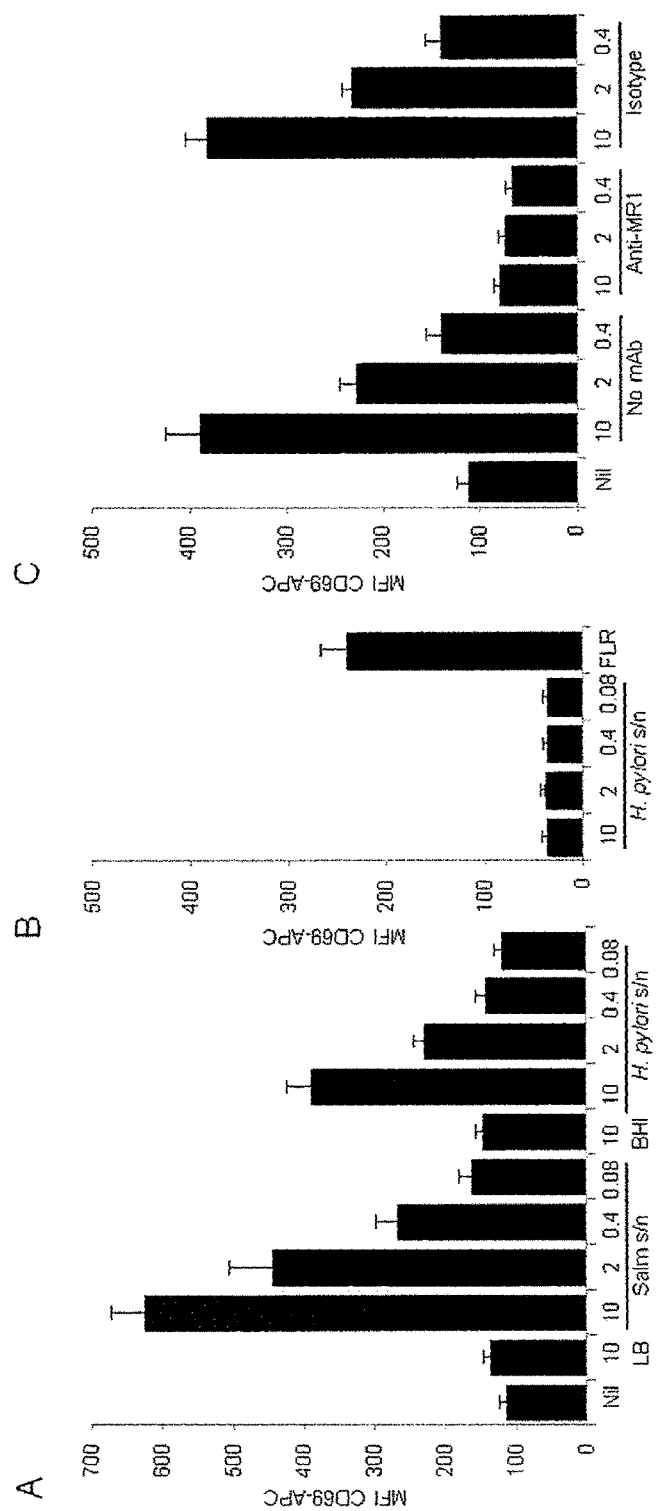
FIG. 15 is a graph showing Helicobacter pylori culture supernatant furnishes ligands that activate Jurkat.MAIT cells (A, C) Jurkat.MAIT and C1R.MR1 cells, or (B) Jurkat.LC13 and C1R.B8 cells, were incubated overnight with filtered S/N from H. pylori SS1 overnight cultures or FLR peptide or media controls, then stained for CD3-PE and anti-CD69-APC. Shown is MFI CD69-APC for gated Jurkat.MAIT or Jurkat.LC13 cells, mean+/−SEM from three experiments. For blocking in (C), C1R.MR1 cells were first incubated with 20 µg/ml anti-MR1 or isotype control mAb far 1 hr before addition of Jurkat.MAIT cells and supernatant or media.

FIG. 15 shows that *Helicobacter pylori* culture s/n activates Jurkat. MAIT reporter cells in vitro. The effect was MR1 dependent and specific to cells expressing MAIT TCR and not an irrelevant control TCR.

Figure 16:
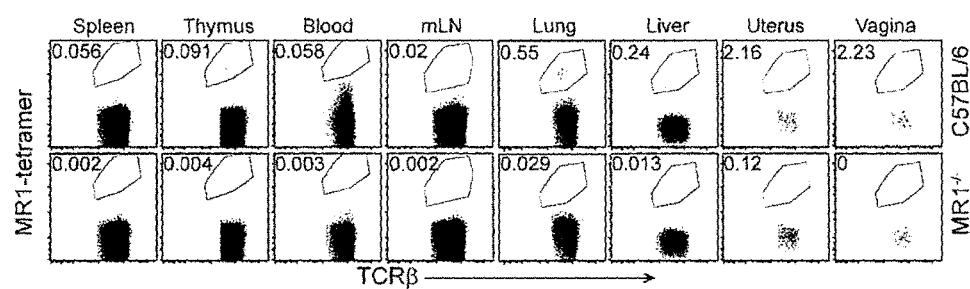
FIG. 16 is a schematic showing detection of MAIT cells in mice using MR1-tetramers. Representative plots showing MAIT cell percentages among TCRβ$^+$ lymphocytes in a range of organs from uninfected C57BL/6 and MR1$^{-/-}$ mice. MAIT cells are defined here as TCRβ$^+$Tetramer$^+$ cells. "MR1-Tetramer"=mouse MR1-5-OP-RU tetramers. Numbers represent MAIT cells as a percentage of TCRβ$^+$ lymphocytes.

MR1-5-OP-RU tetramers can be used to detect MAIT cells in many organs of wt mice (FIG. 16). These are at low numbers in wild-type mice (and much greater numbers in Tg mice, not shown).

Figure 17:
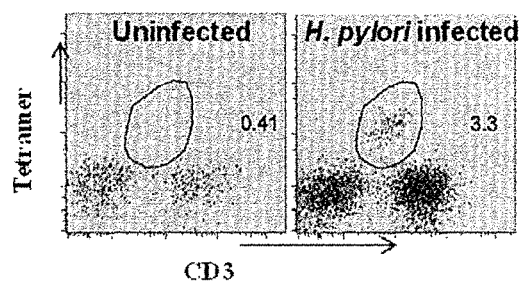
FIG. 17 is a schematic showing that MAIT cells are induced by H. pylori infection. CD3$^+$Tetramer$^+$ MAIT cells were observed in stomachs of C57BL/6 mice orally infected with 10$^7$ H. pylori SS1 for 3 mths. MAIT cells increased from barely detectable levels to approximately 3-5% of lymphocytes (8-10% of T cells) in ~2/10 mice. Total T cells also increased.

FIG. 17 shows MAIT cells accumulate in stomachs of *H. Pylori* infected mice. (only in 20% of mice—similar to development of gastritis in infected humans, which is only in about 20% of people)

Figure 18:
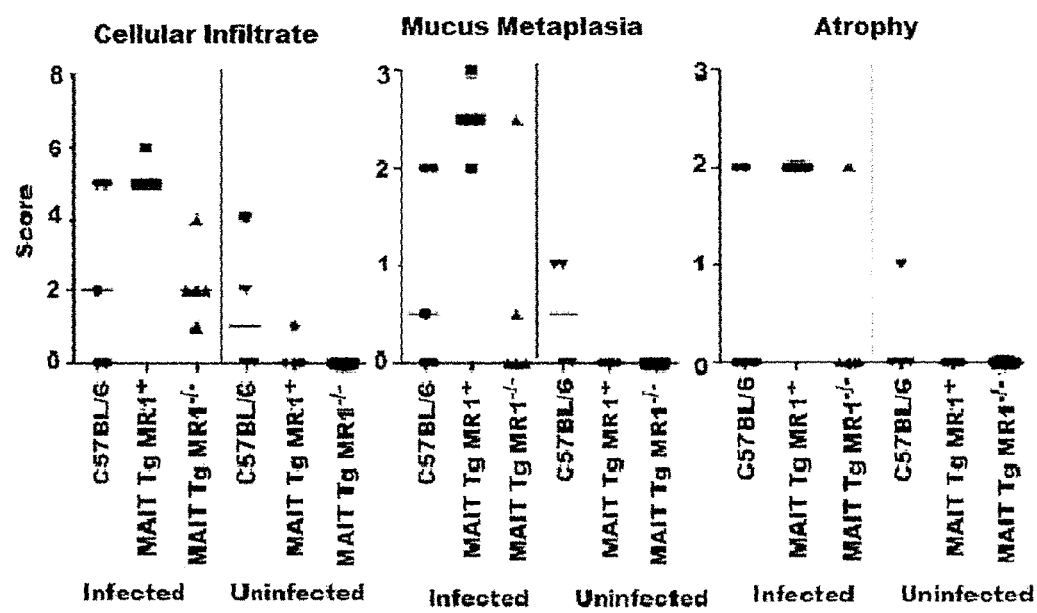
FIG. 18 is a schematic showing MAIT Tg mice have increased pathology following H. pylori infection. C57BL/6, Vα19Tg.MR1$^{-/-}$ or Vα19Tg.MR1$^+$ mice were infected via oro-gastric gavage with 10$^7$ H. pylori SS1. After 8 wks stomachs were harvested and H&E-stained paraffin sections were analysed by a blinded operator for pathologic parameters. Individual scores from female mice are shown.

FIG. 18 shows MAIT Tg mice (more MAIT cells) have greater pathology following *H. pylori* infection than wt mice, or MR1 KO mice (which lack MAIT cells). Although B6 mice do not develop gastric cancer following *H. pylori* infection in this model, mucus metaplasia and atrophy are considered as pre-cancerous pathological markers. Long term infection of mice in future will test if mice with more MAIT cells (eg transgenic) develop cancerous lesions.

Figure 19:
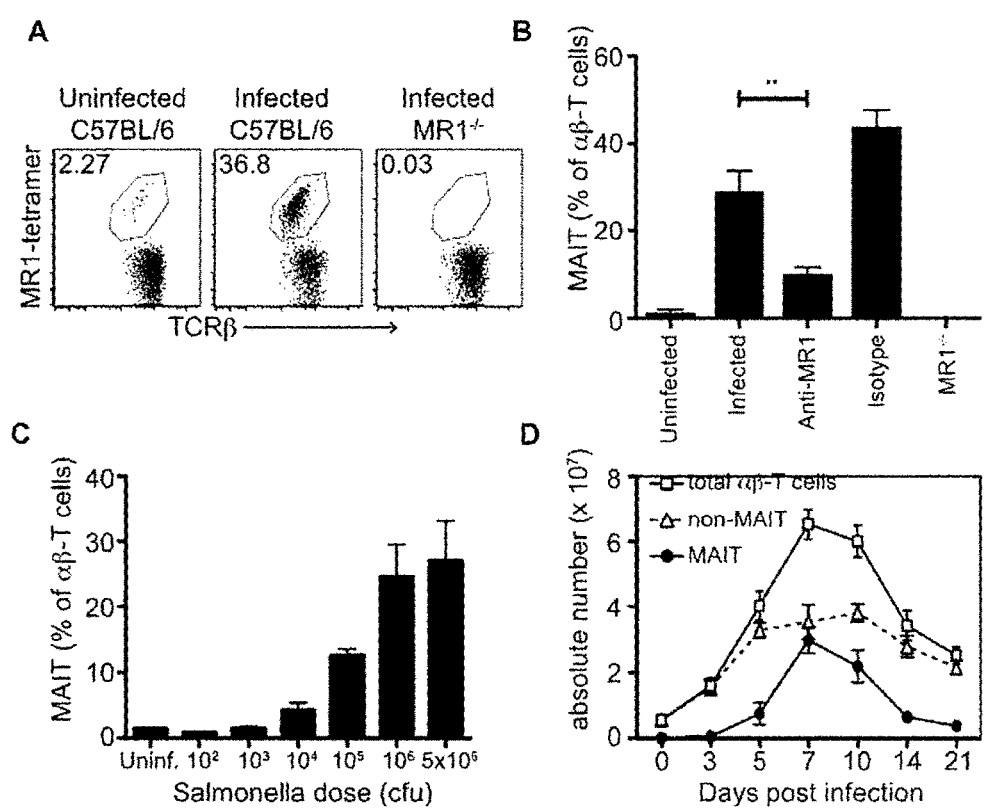
FIG. 19 is a schematic and graph showing A) Representative plots of mice, uninfected C57BL/6 or infected (d7 post infection) C57BL/6 or C57BL/6 MR1$^{-/-}$ mice with 10$^6$ S. Typhimurium BRD509. B) Treatment of mice with anti-MR1 mAb 26.5, but not an isotype control (8E5), blocked the accumulation of MAIT cells upon S. Typhimurium infection. Three mice per group were injected with 0.25 mg indicated antibodies or no Ab i.p. 1 day prior to infection and three times (d1, d3 and d5) post infection. 10$^6$ BRD509 were inoculated i.n. at day 0. At d7-post-infection mice were killed and lung cells were examined for MAIT cell accumulation. Statistics were performed using Student's t test (**: p<0.01, error bar: SEM). Uninfected MR1$^{-/-}$ mice were used as the negative control. The experiment was performed twice with similar results. C) Dose (of *S. Typhimurium* BRD509) response of MAIT cells as a percentage of TCRβ$^+$ cells at d7 post infection. Five mice per group were examined (Mean+/−SEM). The experiment was performed three times with similar results. D) Absolute numbers of MAIT cells (solid circle), conventional non-MAIT cells (open triangle) and total TCRβ$^+$ cells (open square) recovered from lungs were expressed over a time course following intranasal infection with 10$^6$ *S. Typhimurium* BRD509. Five mice per group were examined (Mean+/−SEM). The experiment was performed twice times with similar results.

In a lung model of *salmonella* infection MAIT cells accumulate following infection (FIG. 19). This is dose responsive (C) and can be blocked by anti MR1 (B).

Figure 20:
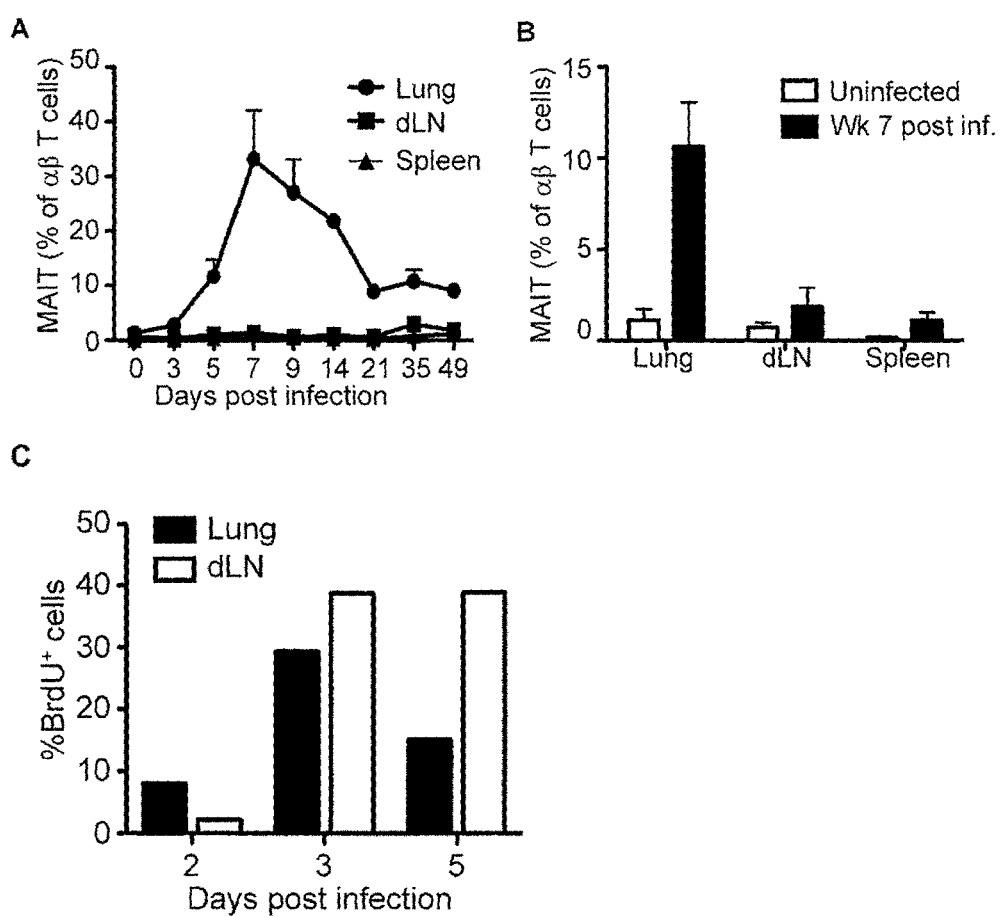
FIG. 20 is a graph showing A) Kinetics of MAIT cell accumulation in lung, mediastinal draining LN and spleen. C57BL/6 or C57BL/6.MR1$^{-/-}$ mice were inoculated with BRD509 i.n. Lungs, mediastinal LNs and spleens were taken to examine the percentage of MAIT cells among αβ-T cells at indicated times post infection. The experiment was performed three times with similar results. Data represent Mean+/−SEM from five mice per group. Data from C57BL/6.MR1$^{-/-}$ mice are not shown. B) MAIT cell percentage in various organs 7 weeks after i.n. *S. Typhimurium* BRD509 inoculation. Organs from five uninfected or infected (day 49 post infection with 10$^6$ BRD509 i.n.) mice were examined for the presence of MAIT cells. Retention of MAIT cells from infected mice (black bar) in comparison with uninfected mice (open bar) was expressed as percentages of total αβ-T cells. The experiment was performed three times with similar results. C) BrdU incorporation by MAIT cells at early time points. Mice were infected i.n. with 10$^6$ *S. Typhimurium* BRD509 or left without infection. At indicated time points, 1 mg BrdU in 200 μl H$_2$O was injected i.p. 2 h after BrdU injection, mice were killed and organs taken to examine BrdU incorporation in MAIT cells and non-MAIT αβ-T cells (not shown). The experiments were carried out independently at indicated time points (day 2, 3 and 5 post infection). Data represent mean from two mice per group. The experiment was performed twice with similar results.

MAIT priming with *salmonella* in the lung results in MAIT cells increasing in number at other sites (blood, LN, spleen (B), stomach, female reproductive tract, not shown) at later time points (FIG. 20). Proliferation occurs locally in the lung and later in draining LN.

Following priming with *Salmonella* intranasally, *Heliobacter* infection now results in robust accumulation of MAIT cells in all mice (FIG. 21). Mice were primed with *Salmonella* intranasally (distant mucosal site), then left for 7 weeks (after the lung MAIT accumulation was reduced. They were then infected with *H. pylori*. This affect will also be tested using 5-OP-RU ligand+Pam2cys (TLR agonist) priming.

Figure 22:
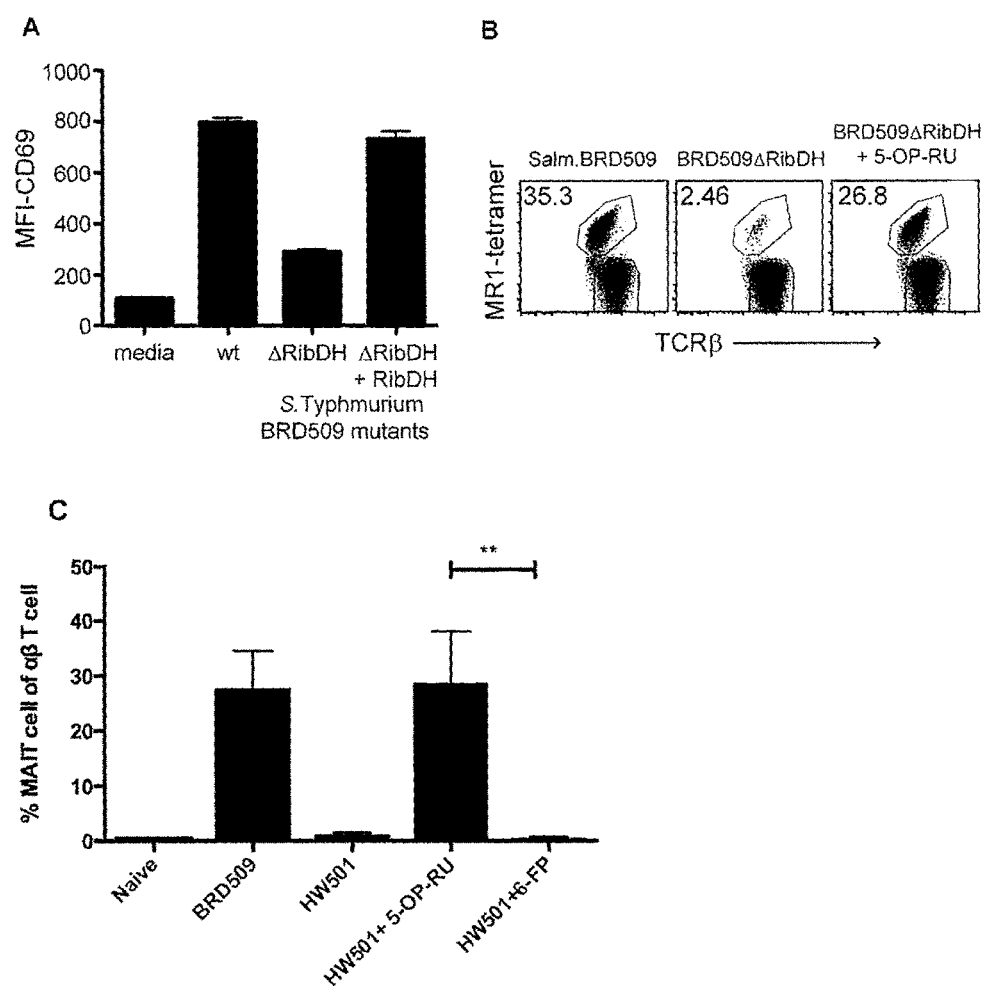
FIG. 22 is a graph showing MAIT cells response depends on specific riboflavin synthesis-derived antigen. A) In vitro activation of Jurkat.MAIT cells by *S. Typhimurium* rib gene deletion mutant strains. *S. Typhimurium* vaccine strain BRD509 (previously described (45)) was used to generate a riboflavin deficient mutant (BRD509ΔribDH) lacking a gene segment containing ribD and ribH, which encode key steps in the pathway. RibD and RibH expression were re-constituted by expression on a plasmid (BR509ΔribDH+RibDH). Jurkat.MAIT cells were incubated overnight with filtered culture supernatant from BRD509 or BRD509ΔribDH mutant (ΔribDH) or reconstituted mutant (BR509ΔribDH+RibDH) in the presence of C1R.MR1 cells. Activation was detected by staining with anti-CD69. Data shows mean MFI of gated Jurkat.MAIT cells with SEM as error bars. The experiment was performed more than three times with similar results. B) and C) In vivo stimulation of MAIT cells by BRD509 and BRD509ΔribDH *S. Typhimurium*. B) Representative plots, and C) MAIT cells as a percentage of αβ-T cells, from the lungs of mice immunised with of BRD509 (10$^6$) or BR509ΔribDH (10$^7$) *Salmonella* (i.n.), in combination with 5-OP-RU or 6-FP (200 μl of 1.52 μM i.v.) three times at d1, d3 and d5 post infection. Day 7 post infection data are shown. Three mice per group were examined (error bar=SD). The experiment was performed twice with similar results.

Accumulation of MAIT cells in lungs following *Salmonella* infection is dependent on the riboflavin synthesis pathway-derived ligands (FIG. 22). Mutant *Salmonella* (ΔribDH) which cannot make riboflavin (and thus the ligands), do not result in activation of Jurkat.MAIT reporter cells in vitro, or accumulation of MAIT cells after lung infection. However, if mutant *salmonella*+synthetic 5-OP-RU is used, accumulation is observed.

Figure 23:
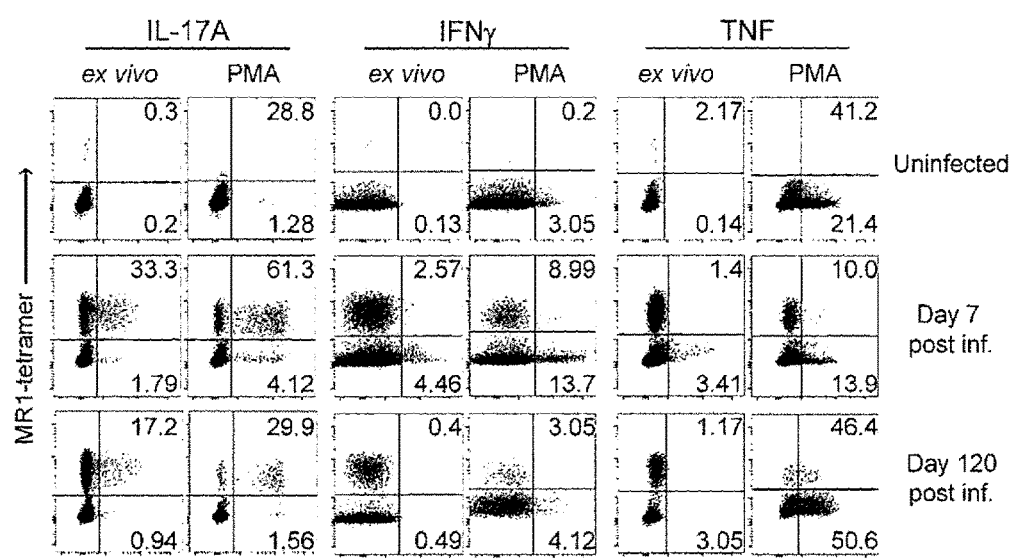
FIG. 23 is a schematic showing cytokine profiling of MAIT cells upon infection with *S. Typhimurium* BRD509. Intracellular cytokine staining of MAIT and non-MAIT αβ-T cells at d7 post infection detected directly ex vivo, or following stimulation with PMA and ionomycin. The numbers represent the percentages of cytokine producing cells from MAIT (upper quadrant) and non-MAIT αβ-T cells (lower quadrant).

FIG. 23 shows that MAIT cells accumulated in lungs following *Salmonella* infection produce IL-17, IFN and TNF.

FIG. 24 shows that CD8+ MAIT cells preferentially accumulate following intranasal *Salmonella* infection.

The reference to any prior art in this specification is not, and should not be taken as, an acknowledgment or any form of suggestion that that prior art forms part of the common general knowledge in Australia or elsewhere.

BIBLIOGRAPHY

1. Godfrey, D. I., J. Rossjohn, and J. McCluskey. (2010b) Fighting infection with your MAITs. *Nat Immunol* 11:693-695.
2. Gold, M. C., S. Cerri, S. Smyk-Pearson, M. E. Cansler, T. M. Vogt, J. Delepine, E. Winata, G. M. Swarbrick, W.-J. Chua, Y. Y. L. Yu, O. Lantz, M. S. Cook, M. D. Null, D. B. Jacoby, M. J. Harriff, D. A. Lewinsohn, T. H. Hansen, and D. M. Lewinsohn. (2010) Human Mucosal Associated Invariant T Cells Detect Bacterially Infected Cells. *PLoS Biol* 8:e1000407.
3. Gold, M. C., S. Cerri, S. Smyk-Pearson, M. E. Cansler, T. M. Vogt, J. Delepine, E. Winata, G. M. Swarbrick, W.-J. Chua, Y. Y. L. Yu, O. Lantz, M. S. Cook, M. D. Null, D. B. Jacoby, M. J. Harriff, D. A. Lewinsohn, T. H. Hansen, and D. M. Lewinsohn. (2010a) Human Mucosal Associated Invariant T Cells Detect Bacterially Infected Cells. *PLoS Biol* 8:e1000407.
4. Gold, M. C., S. Cerri, S. Smyk-Pearson, M. E. Cansler, T. M. Vogt, J. Delepine, E. Winata, G. M. Swarbrick, W. J. Chua, Y. Y. Yu, O. Lantz, M. S. Cook, M. D. Null, D. B. Jacoby, M. J. Harriff, D. A. Lewinsohn, T. H. Hansen, and D. M. Lewinsohn. (2010b) Human mucosal associated invariant T cells detect bacterially infected cells. *PLoS Biol* 8:e1000407.
5. Kawachi, I., J. Maldonado, C. Strader, and S. Gilfillan. (2006). MR1-Restricted VŒ±19i Mucosal Associated Invariant T Cells Are Innate T Cells in the Gut Lamina Propria That Provide a Rapid and Diverse Cytokine Response. *The Journal of Immunology* 176:1618-1627.
6. Le Bourhis, L., E. Martin, I. Peguillet, A. Guihot, N. Froux, M. Core, E. Levy, M. Dusseaux, V. Meyssonnier, V. Premel, C. Ngo, B. Riteau, L. Duban, D. Robert, S. Huang, M. Rottman, C. Soudais, and O. Lantz. (2010) Antimicrobial activity of mucosal-associated invariant T cells. *Nat Immunol* 11:701-708.
7. Le Bourhis, L., L. Guerri, M. Dusseaux, E. Martin, C. Soudais, and O. Lantz. (2011) Mucosalassociated invariant T cells: unconventional development and function. *Trends in Immunology* 32:212-218.
8. Martin, E., E. Treiner, L. Duban, L. Guerri, H. Laude, C. Toly, V. Premel, A. Devys, I. C. Moura, F. Tilloy, S. Cherif, G. Vera, S. Latour, C. Soudais, and O. Lantz. (2009) Stepwise Development of MAIT Cells in Mouse and Human. *PLoS Biol* 7:e54.
9. Peterfalvi A, Gomori E, Magyarlaki T, Pal J, Banati M, Javorhazy A, Szekeres-Bartho J, Szereday L, Illes Z, (2008). Invariant Valpha7.2-Jalpha33 TCR is expressed in human kidney and brain tumors indicating infiltration by mucosal-associated invariant T (MAIT) cells. *Int Immunol.* 20(12):1517-25.
10. Reantragoon R, Kjer-Nielsen L, Patel O, Chen Z, Illing P T, Bhati M, Kostenko L, Bharadwaj M, Meehan B, Hansen T H, Godfrey D I, Rossjohn J, McCluskey J. (2012) Structural insight into MR1-mediated recognition of the mucosal associated invariant T cell receptor. *J Exp Med.* 209(4):761-74
11. Tilloy, F., E. Treiner, S.-H. Park, C. Garcia, F. o. Lemonnier, H. de la Salle, A. Bendelac, M. Bonneville, and O. Lantz. (1999) An Invariant T Cell Receptor Œ ±Chain Defines a Novel TAP-independent Major Histocompatibility Complex Class Ib, Ärestricted Œ ±/ Œ <T Cell Subpopulation in Mammals. *The Journal of Experimental Medicine* 189:1907-1921.
12. Treiner, E., L. Duban, S. Bahram, M. Radosavljevic, V. Wanner, F. Tilloy, P. Affaticati, S. Gilfillan, and O. Lantz. (2003) Selection of evolutionarily conserved mucosal-associated invariant T cells by MR1. *Nature* 422:164-169.
13. Zinkernagel and Doherty, (1997).
14. Altman et al., "Formation of functional peptide complexes of class II major histocompatibility complex proteins from subunits produced in *Escherichia coli,*" *Proc. Natl. Acad. Sci. USA*, pp. 10330-10334, November 1993, vol. 90.
15. Garboczi et al., "HLA-A2.peptide complexes: Refolding and crystallization of molecules expressed in *Escherichia coli* and complexed with single antigenic peptides," *Proc. Natl. Acad. Sci.,* 89:3429-3433, 1992.f
16. Vitreschak, A. G., Rodionov, D. A., Mironov, A. A. & Gelfand, M. S. Riboswitches: the oldest mechanism for the regulation of gene expression? *Trends in genetics: TIG* 20, 44-50 (2004).
17. Burgess, C., O'Connell-Motherway, M., Sybesma, W., Hugenholtz, J. & van Sinderen, D. Riboflavin Production in *Lactococcus lactis*: Potential for In Situ Production of Vitamin-Enriched Foods. *Applied and Environmental Microbiology* 70, 5769-5777 (2004).
18. Cushman, M. et al. Design, Synthesis, and Evaluation of 6-Carboxyalkyl and 6-Phosphonoxyalkyl Derivatives of 7-Oxo-8-ribitylaminolumazines as Inhibitors of Riboflavin Synthase and Lumazine Synthase. *The Journal of Organic Chemistry* 67, 5807-5816 (2002).
19. Bacher, A., Eberhardt, S., Fischer, M., Kis, K. & Richter, G. biosynthesis of vitamin B2 (riboflavin). *Annual Review of Nutrition* 20, 153-167 (2000).
20. Kis, K., Kugelbrey, K. & Bacher, A. Biosynthesis of Riboflavin. The Reaction Catalyzed by 6,7-Dimethyl-8-ribityllumazine Synthase Can Proceed without Enzymatic Catalysis under Physiological Conditions. *The Journal of Organic Chemistry* 66, 2555-2559 (2001).
21. Wang, Y. & Ho, C.-T. Flavour chemistry of methylglyoxal and glyoxal. *Chemical Society Reviews* 41, 4140-4149 (2012).
22. Patel, O. et al. Recognition of vitamin B metabolites by mucosal-associated invariant T cells. *Nat Commun* 4, 2142 (2013).
23. Hoiseth, S. K. & Stocker, B. A. D. Aromatic-dependent *Salmonella typhimurium* are nonvirulent and effective as live vaccines. *Nature* 291, 238-239 (1981).
24. Strugnell, R. et al. Characterization of a *Salmonella typhimurium* aro vaccine strain expressing the P.69 antigen of *Bordetella pertussis*. *Infection and Immunity* 60, 3994-4002 (1992).

25. Plaut, G. W. E. & Harvey, R. A. in *Methods in Enzymology* Vol. Volume 18, Part B (eds B. McCormick Donald & D. Wright Lemuel) 515-538 (Academic Press, 1971).
26. Huang, S. et al. Evidence for MR1 Antigen Presentation to Mucosal-associated Invariant T Cells. *Journal of Biological Chemistry* 280, 21183-21193 (2005).
27. CCP4. The CCP4 suite: programs for protein crystallography. *Acta Crystallogr D Biol Crystallogr* 50, 760-763 (1994).
28. McCoy, A. J. Solving structures of protein complexes by molecular replacement with Phaser. *Acta Crystallogr D Biol Crystallogr* 63, 32-41 (2007).
29. Zwart, P. H. et al. Automated structure solution with the PHENIX suite. *Methods Mol Biol* 426, 419-435 (2008).
30. Emsley, P. & Cowtan, K. Coot: model-building tools for molecular graphics. *Acta Crystallogr D Biol Crystallogr* 60, 2126-2132 (2004).
31. Mejerovics A, Yankelevich W J, Cowley S C. *Proc Natl Acad Sci USA.,* 2013 Aug. 13; 110(33): E3119-28.
32. Serriari N E, Eoche M, Lamotte L., Fumery M, Marcelo P, Chatelain D, Barre A, Nguyen-Khac E, Lantz O, Dupas J L, Treiner E. *Clin Exp Immunol.* 2014 Jan. 23. doi: 10.1111/cei.12277

The invention claimed is:

1. An MR1-ligand subunit [MR1-L] which binds MAIT cells, wherein said ligand is represented by Formula (I):

(I)

or a salt, tautomer, or stereoisomer thereof
wherein:

$R_1$ is selected from the group consisting of:
X—C(O)—$R_1$' (where $R_1$' is H, or optionally substituted $C_1$-$C_6$alkyl, and X is independently a bond or a divalent linker selected from the group consisting of $C_1$-$C_3$ optionally substituted alkylene, —$NR_2$'— optionally substituted $C_1$-$C_3$alkylene-, —O— optionally substituted $C_1$-$C_3$alkylene-, —S— optionally substituted $C_1$-$C_3$alkylene-, —S(O)— optionally substituted $C_1$-$C_3$alkylene-, —N=$CR_2$'—, —$CR_2$'=$CR_2$"—, —$NR_2$'—C(O)—, —O—C(O)—, or —S—C(O)— where each $R_2$' and $R_2$" is independently selected from H, halogen, CN, or optionally substituted $C_1$-$C_6$alkyl); —X'—C(O)$NR_3$'$R_4$' (where $R_3$' is H or optionally substituted $C_1$-$C_6$alkyl and $R_4$' is optionally substituted $C_1$-$C_6$alkyl, OH, or CN or $R_3$'$R_4$' together form an optionally substituted heterocyclyl or optionally substituted heteroaryl, and X' is independently a bond or a $C_1$-$C_3$ optionally substituted alkylene); —X"—C(O)O$R_5$' (wherein $R_5$' is H or optionally substituted $C_1$-$C_6$alkyl, and X" is independently a bond or a $C_1$-$C_3$ optionally substituted alkylene); —X'"—C(O)NHSO$_2$$R_6$' (wherein $R_6$' is optionally substituted aryl, or optionally substituted $C_1$-$C_6$alkyl, and X'" is independently a bond or a $C_1$-$C_3$ optionally substituted alkylene); and —X""—S(O)$_2$NH$R_7$' (wherein $R_7$' is H, optionally substituted $C_1$-$C_6$alkyl, or optionally substituted aryl, and X"" is independently a bond or a $C_1$-$C_3$ optionally substituted alkylene);

$R_2$ is selected from the group consisting of optionally substituted $C_{1-8}$alkyl, —NH(optionally substituted $C_{1-6}$alkyl), —N(optionally substituted $C_{1-6}$alkyl) (optionally substituted aryl), —N(optionally substituted $C_{1-6}$alkyl)$_2$, —O(optionally substituted $C_{1-6}$alkyl), —OC(O)($C_{1-6}$alkyl), —S(optionally substituted $C_{1-6}$alkyl), —SC(O)($C_{1-6}$alkyl), and —S(O) (optionally substituted $C_{1-6}$alkyl); and Y and Z are oxo.

2. The [MR1-L] of claim 1, wherein $R_1$ is —X—C(O)—$R_1$' (where $R_1$' is H, or optionally substituted $C_1$-$C_6$alkyl, and X is independently a divalent linker selected from the group consisting of $C_1$-$C_3$ optionally substituted alkylene, —$NR_2$'— optionally substituted $C_1$-$C_3$alkylene-, —O— optionally substituted $C_1$-$C_3$alkylene-, —N=$CR_2$'—, —$CR_2$'=$CR_2$"—, —$NR_2$'—C(O)—, —OC(O)—, or —SC(O)— where each $R_2$' and $R_2$" is independently selected from H or optionally substituted $C_1$-$C_6$alkyl); and $R_2$ is selected from the group consisting of optionally substituted $C_{1-8}$alkyl, NH(optionally substituted $C_{1-6}$alkyl), —N(optionally substituted $C_{1-6}$allyl)(optionally substituted aryl), —N(optionally substituted $C_{1-6}$alkyl)$_2$, —O(optionally substituted $C_{1-6}$alkyl), —OC(O)($C_{1-6}$alkyl), —S(optionally substituted $C_{1-6}$alkyl), —SC(O)($C_{1-6}$alkyl), or —S(O)(optionally substituted $C_{1-6}$alkyl).

3. The [MR1-L] of claim 1, wherein $R_1$ is —X—C(O)$R_1$' where $R_1$' is H or $C_{1-6}$alkyl and X is independently —$NR_2$'—$CH_2$—, —N=$CR_2$'—, —$CR_2$'=$CR_2$"—, —$NR_2$'—C(O)—, —OC(O)—, or —SC(O)— where $R_2$' and $R_2$" are independently H or $C_{1-6}$alkyl; and $R_2$ is —NH—$C_2$-$C_6$ alkyl optionally substituted 1 to 6 times with OH, $OR_1$', NH$_2$, NH$R_1$', $NR_1$'$R_2$', SH, or $SR_1$', where $R_1$' and $R_2$' are independently $C_{1-6}$alkyl, $C_{1-6}$acyl, $C_{1-6}$amido, or $C_{1-6}$thioamido.

4. The [MR1-L] of claim 1, wherein $R_1$ is —N=$CR_2$'—C(O)$R_1$' or —CH=$CR_2$"—C(O)$R_1$', where each $R_1$' and $R_2$' is independently H or $C_{1-6}$alkyl; and $R_2$ is —NH—$C_2$-$C_6$ alkyl optionally substituted 1 to 4 times with OH.

5. The [MR1-L] of claim 1, wherein $R_1$' is H or $C_1$-$C_6$alkyl optionally substituted by a group selected from halogen, hydroxy, mercapto or amino.

6. The [MR1-L] of claim 1, wherein said ligand is selected from the group consisting of:

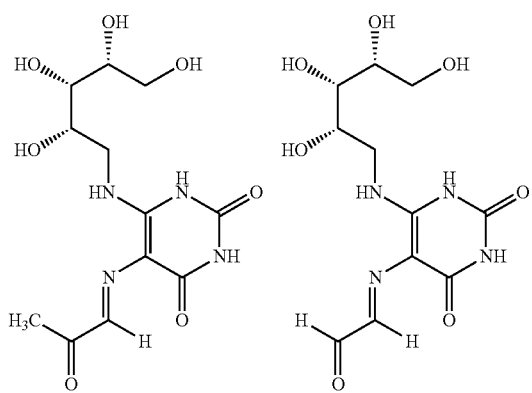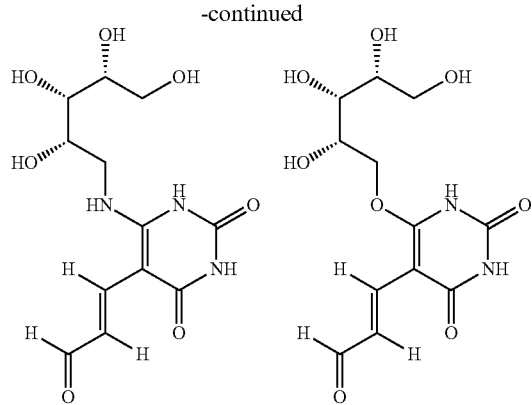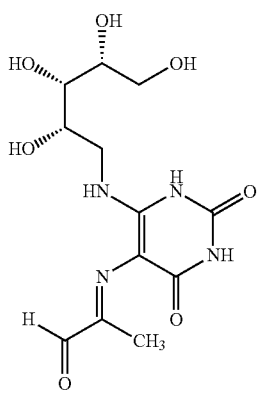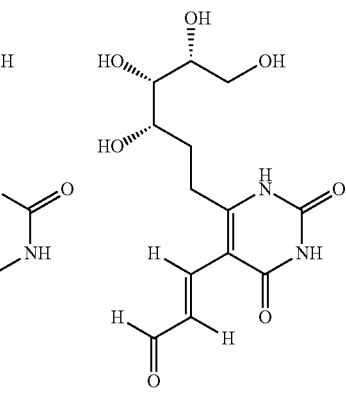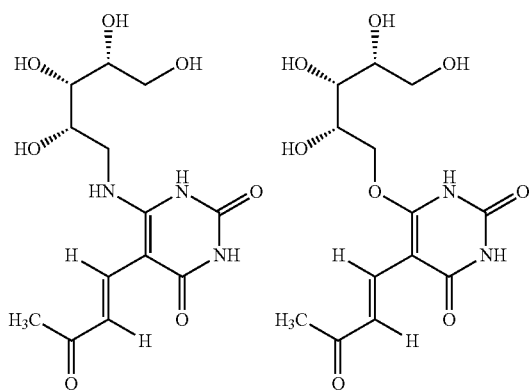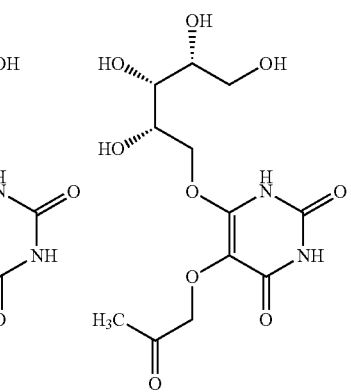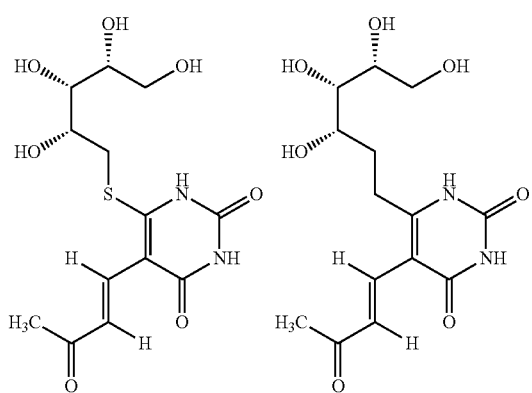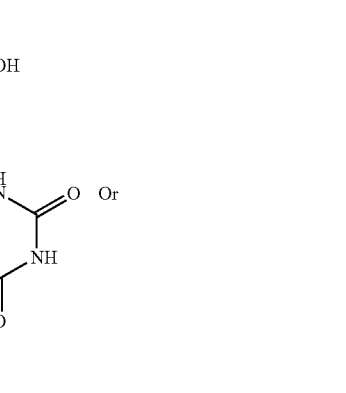

-continued

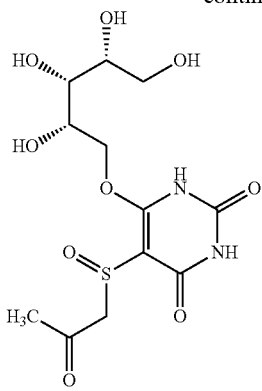

or a salt, tautomer, or stereoisomer thereof.

7. The [MR1-L] of claim 1, wherein the optional substituents comprise a substituent selected from the group consisting of halogen, oxo, thio, $C_1$-$C_6$alkyl, $C_1$-$C_6$alkoxy, $C_2$-$C_6$alkenyl, halo $C_1$-$C_6$alkyl, halo $C_1$-$C_6$alkoxy, —OH, phenyl, benzyl, phenoxy, benzyloxy, —$NH_2$, —$NHC_1$-$C_4$alkyl, —$N(C_1$-$C_4$alkyl$)_2$, —$NHC_1$-$C_4$acyl, —NHC(O)$NH_2$, —NHC(O)$NHC_1$-$C_4$alkyl, —NHC(O)$N(C_1$-$C_4$alkyl$)_2$, —NHC(S)$NH_2$, —NHC(S)$C_1$-$C_4$alkyl, —NHC(S)N$(C_1$-$C_4$alkyl$)_2$, guanidino, —CN, —$NO_2$, mercapto, —$S(O_2)NH_2$, —$S(O_2)NHC_1$-$C_4$alkyl, $CO_2H$, $CO_2NH_2$ and $CO_2NHC_1$-$C_4$alkyl.

8. The [MR1-L] of claim 1, wherein said ligand is selected from the group consisting of 5-(2-oxoethylideneamino)-6-D-ribitylaminouracil (5-OE-RU), 5-(2-oxopropylideneamino)-6-D-ribitylaminouracil (5-OP-RU), which were either isolated or generated in situ by mixing 5-amino-6-D-ribitylaminouracil (5-A-RU) with glyoxal or methylglyoxal, respectively, or functional analogs thereof, to oxidised forms thereof and reduced forms thereof.

9. The [MR1-L] of claim 1 which is in the form of a multimeric complex, wherein said multimeric complex comprises the formula [MR1-L]$_n$, wherein n≥2 and ≤50.

10. The multimeric complex of claim 9, wherein n=4.

11. The [MR1-L] of claim 1, wherein said binding modulates MAIT cells.

12. The [MR1-L] of claim 11, wherein said modulation is MAIT cell activation.

13. The [MR1-L] of claim 1, wherein the MR1 comprises all or part of SEQ ID NO: 1, SEQ ID NO: 4, or a functional derivative thereof having one or more amino acid substitutions, additions and/or deletions to SEQ ID NO: 1 or SEQ ID NO: 4.

14. The [MR1-L] of claim 13, wherein said MR1 comprises at least one mutation selected from the list consisting of K43A, K43M, K43I, K43L, K43F, K43Q, Y7A, Y7W, R9K, R9A, S24F, Y62A, L66A, L66F, W69A, R94K, R94A, I96A, I96F and W156A.

15. The [MR1-L] of claim 14, wherein said MR1 comprises one or more mutations in surface exposed groups selected from the list consisting of D57, R61, L65, M72, V75, R79, T138, Q141, N146, H148, L151, N155, E158, and R167.

16. A compound selected from the group consisting of:

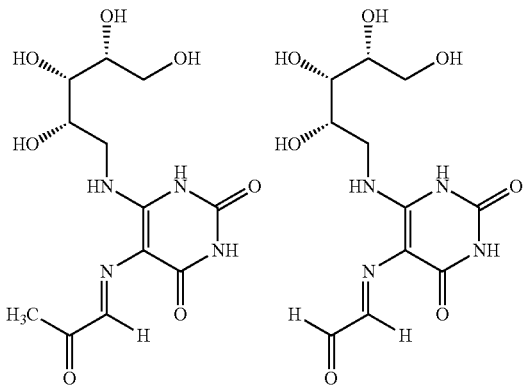

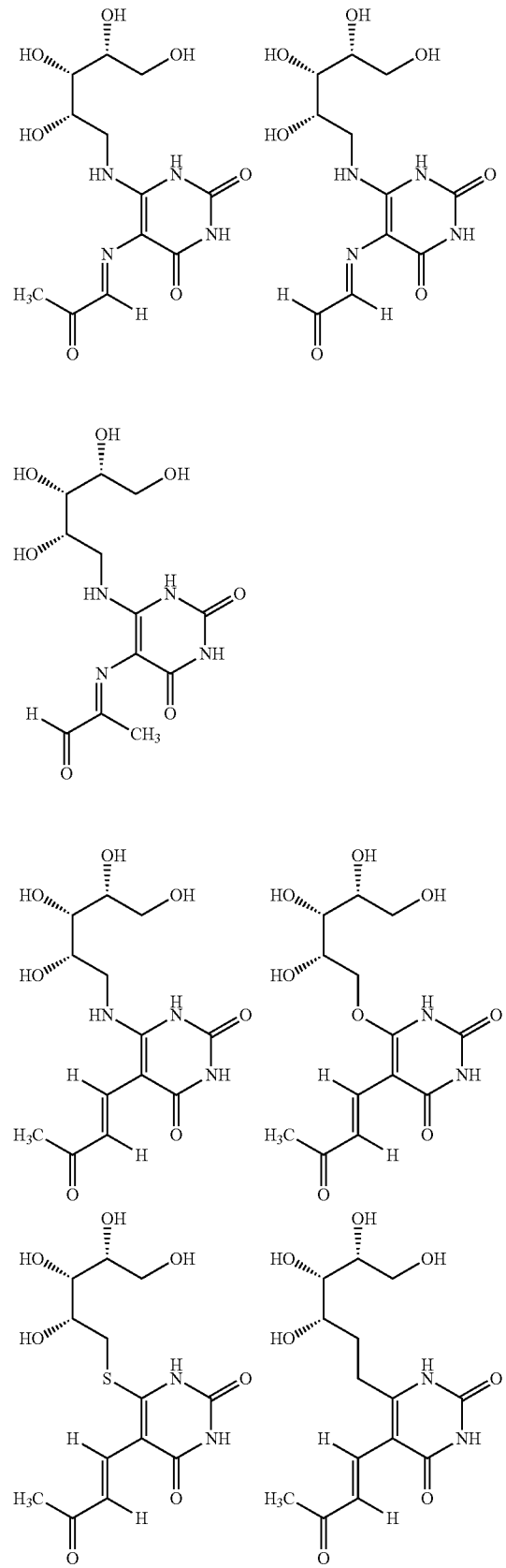

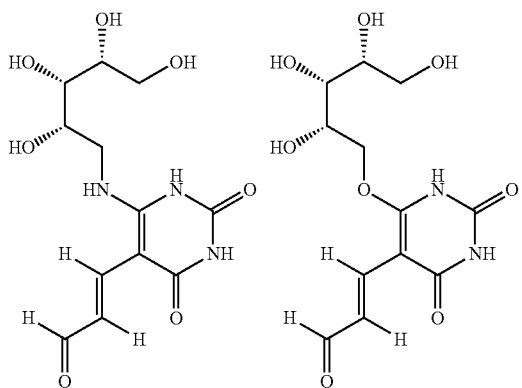

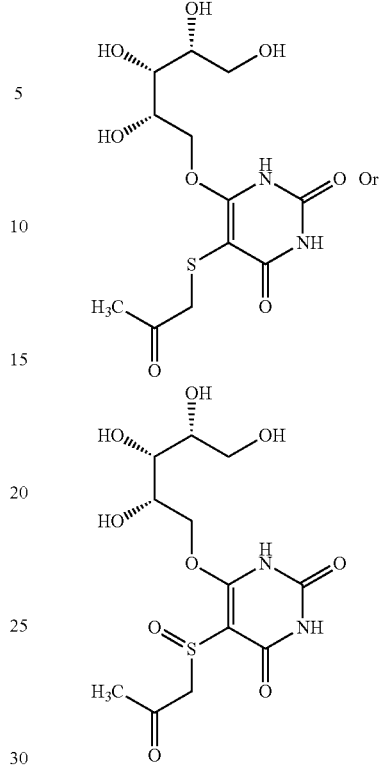

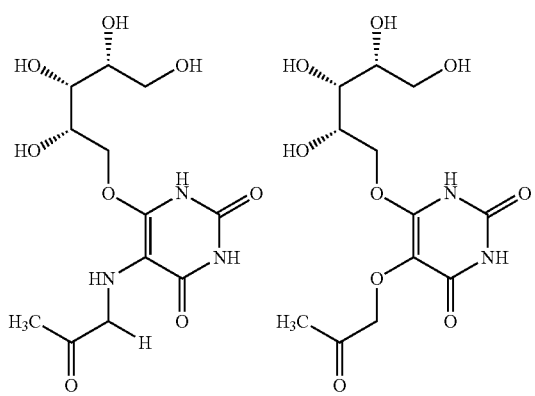

or a salt, tautomer, or stereoisomer thereof.

17. The compound according to claim 16, wherein said compound is selected from the group consisting of 5-(2-oxoethylideneamino)-6-D-ribitylaminouracil (5-OE-RU), 5-(2-oxopropylideneamino)-6-D-ribitylaminouracil (5-OP-RU), which were either isolated or generated in situ by mixing 5-amino-6-D-ribitylaminouracil (5-A-RU) with glyoxal or methylglyoxal, respectively, or functional analogs thereof, oxidised forms thereof and reduced forms thereof.

18. A method of detecting the presence of MAIT cells in a biological sample from a subject, the method comprising the steps of a) contacting the biological sample with antigen presenting cells expressing MR1 bound to ligand, under conditions that would allow binding of the MR1 with MAIT cells present in the sample; and b) detecting the presence of MAIT cell activity, wherein said ligand is defined in claim 16 or is a compound according to claim 16.

19. A pharmaceutical composition comprising an MR1 ligand subunit of claim 1 together with one or more pharmaceutically acceptable carriers and/or diluents.

20. A pharmaceutical composition comprising a compound of claim 16 together with one or more pharmaceutically acceptable carriers and/or diluents.

* * * * *

SEQUENCE LISTING

```
<160> NUMBER OF SEQ ID NOS: 6

<210> SEQ ID NO 1
<211> LENGTH: 341
<212> TYPE: PRT
<213> ORGANISM: Homo sapien

<400> SEQUENCE: 1

Met Gly Glu Leu Met Ala Phe Leu Leu Pro Leu Ile Ile Val Leu Met
1               5                   10                  15

Val Lys His Ser Asp Ser Arg Thr His Ser Leu Arg Tyr Phe Arg Leu
            20                  25                  30

Gly Val Ser Asp Pro Ile His Gly Val Pro Glu Phe Ile Ser Val Gly
        35                  40                  45

Tyr Val Asp Ser His Pro Ile Thr Thr Tyr Asp Ser Val Thr Arg Gln
    50                  55                  60

Lys Glu Pro Arg Ala Pro Trp Met Ala Glu Asn Leu Ala Pro Asp His
65                  70                  75                  80

Trp Glu Arg Tyr Thr Gln Leu Leu Arg Gly Trp Gln Gln Met Phe Lys
                85                  90                  95

Val Glu Leu Lys Arg Leu Gln Arg His Tyr Asn His Ser Gly Ser His
            100                 105                 110

Thr Tyr Gln Arg Met Ile Gly Cys Glu Leu Leu Glu Asp Gly Ser Thr
        115                 120                 125

Thr Gly Phe Leu Gln Tyr Ala Tyr Asp Gly Gln Asp Phe Leu Ile Phe
    130                 135                 140

Asn Lys Asp Thr Leu Ser Trp Leu Ala Val Asp Asn Val Ala His Thr
145                 150                 155                 160

Ile Lys Gln Ala Trp Glu Ala Asn Gln His Glu Leu Leu Tyr Gln Lys
                165                 170                 175

Asn Trp Leu Glu Glu Glu Cys Ile Ala Trp Leu Lys Arg Phe Leu Glu
            180                 185                 190

Tyr Gly Lys Asp Thr Leu Gln Arg Thr Glu Pro Pro Leu Val Arg Val
        195                 200                 205

Asn Arg Lys Glu Thr Phe Pro Gly Val Thr Ala Leu Phe Cys Lys Ala
    210                 215                 220

His Gly Phe Tyr Pro Pro Glu Ile Tyr Met Thr Trp Met Lys Asn Gly
225                 230                 235                 240

Glu Glu Ile Val Gln Glu Ile Asp Tyr Gly Asp Ile Leu Pro Ser Gly
                245                 250                 255

Asp Gly Thr Tyr Gln Ala Trp Ala Ser Ile Glu Leu Asp Pro Gln Ser
            260                 265                 270

Ser Asn Leu Tyr Ser Cys His Val Glu His Cys Gly Val His Met Val
```

```
                    275                 280                 285
Leu Gln Val Pro Gln Glu Ser Glu Thr Ile Pro Leu Val Met Lys Ala
290                 295                 300

Val Ser Gly Ser Ile Val Leu Ile Val Leu Ala Gly Val Gly Val
305                 310                 315                 320

Leu Val Trp Arg Arg Pro Arg Glu Gln Asn Gly Ala Ile Tyr Leu
                325                 330                 335

Pro Thr Pro Asp Arg
                340

<210> SEQ ID NO 2
<211> LENGTH: 319
<212> TYPE: PRT
<213> ORGANISM: Homo sapien

<400> SEQUENCE: 2

Arg Thr His Ser Leu Arg Tyr Phe Arg Leu Gly Val Ser Asp Pro Ile
1               5                   10                  15

His Gly Val Pro Glu Phe Ile Ser Val Gly Tyr Val Asp Ser His Pro
                20                  25                  30

Ile Thr Thr Tyr Asp Ser Val Thr Arg Gln Lys Glu Pro Arg Ala Pro
            35                  40                  45

Trp Met Ala Glu Asn Leu Ala Pro Asp His Trp Glu Arg Tyr Thr Gln
50                  55                  60

Leu Leu Arg Gly Trp Gln Gln Met Phe Lys Val Glu Leu Lys Arg Leu
65                  70                  75                  80

Gln Arg His Tyr Asn His Ser Gly Ser His Thr Tyr Gln Arg Met Ile
                85                  90                  95

Gly Cys Glu Leu Leu Glu Asp Gly Ser Thr Thr Gly Phe Leu Gln Tyr
                100                 105                 110

Ala Tyr Asp Gly Gln Asp Phe Leu Ile Phe Asn Lys Asp Thr Leu Ser
            115                 120                 125

Trp Leu Ala Val Asp Asn Val Ala His Thr Ile Lys Gln Ala Trp Glu
130                 135                 140

Ala Asn Gln His Glu Leu Leu Tyr Gln Lys Asn Trp Leu Glu Glu Glu
145                 150                 155                 160

Cys Ile Ala Trp Leu Lys Arg Phe Leu Glu Tyr Gly Lys Asp Thr Leu
                165                 170                 175

Gln Arg Thr Glu Pro Pro Leu Val Arg Val Asn Arg Lys Glu Thr Phe
            180                 185                 190

Pro Gly Val Thr Ala Leu Phe Cys Lys Ala His Gly Phe Tyr Pro Pro
            195                 200                 205

Glu Ile Tyr Met Thr Trp Met Lys Asn Gly Glu Glu Ile Val Gln Glu
210                 215                 220

Ile Asp Tyr Gly Asp Ile Leu Pro Ser Gly Asp Gly Thr Tyr Gln Ala
225                 230                 235                 240

Trp Ala Ser Ile Glu Leu Asp Pro Gln Ser Ser Asn Leu Tyr Ser Cys
                245                 250                 255

His Val Glu His Cys Gly Val His Met Val Leu Gln Val Pro Gln Glu
                260                 265                 270

Ser Glu Thr Ile Pro Leu Val Met Lys Ala Val Ser Gly Ser Ile Val
            275                 280                 285

Leu Val Ile Val Leu Ala Gly Val Gly Val Leu Val Trp Arg Arg Arg
290                 295                 300
```

Pro Arg Glu Gln Asn Gly Ala Ile Tyr Leu Pro Thr Pro Asp Arg
305                 310                 315

<210> SEQ ID NO 3
<211> LENGTH: 22
<212> TYPE: PRT
<213> ORGANISM: Homo sapien

<400> SEQUENCE: 3

Met Gly Glu Leu Met Ala Phe Leu Leu Pro Leu Ile Ile Val Leu Met
1               5                   10                  15

Val Lys His Ser Asp Ser
            20

<210> SEQ ID NO 4
<211> LENGTH: 341
<212> TYPE: PRT
<213> ORGANISM: Mus musculus

<400> SEQUENCE: 4

Met Met Leu Leu Leu Pro Leu Leu Ala Val Phe Leu Val Lys Arg Ser
1               5                   10                  15

His Thr Arg Thr His Ser Leu Arg Tyr Phe Arg Leu Ala Val Ser Asp
            20                  25                  30

Pro Gly Pro Val Val Pro Glu Phe Ile Ser Val Gly Tyr Val Asp Ser
        35                  40                  45

His Pro Ile Thr Thr Tyr Asp Ser Val Thr Arg Gln Lys Glu Pro Lys
    50                  55                  60

Ala Pro Trp Met Ala Glu Asn Leu Ala Pro Asp His Trp Glu Arg Tyr
65                  70                  75                  80

Thr Gln Leu Leu Arg Gly Trp Gln Gln Thr Phe Lys Ala Glu Leu Arg
                85                  90                  95

His Leu Gln Arg His Tyr Asn His Ser Gly Leu His Thr Tyr Gln Arg
            100                 105                 110

Met Ile Gly Cys Glu Leu Leu Glu Asp Gly Ser Thr Thr Gly Phe Leu
        115                 120                 125

Gln Tyr Ala Tyr Asp Gly Gln Asp Phe Ile Ile Phe Asn Lys Asp Thr
    130                 135                 140

Leu Ser Trp Leu Ala Met Asp Tyr Val Ala His Ile Thr Lys Gln Ala
145                 150                 155                 160

Trp Glu Ala Asn Leu His Glu Leu Gln Tyr Gln Lys Asn Trp Leu Glu
                165                 170                 175

Glu Glu Cys Ile Ala Trp Leu Lys Arg Phe Leu Glu Tyr Gly Arg Asp
            180                 185                 190

Thr Leu Glu Arg Thr Glu His Pro Val Val Arg Thr Thr Arg Lys Glu
        195                 200                 205

Thr Phe Pro Gly Ile Thr Thr Phe Cys Arg Ala His Gly Phe Tyr
    210                 215                 220

Pro Pro Glu Ile Ser Met Thr Trp Met Lys Asn Gly Glu Glu Ile Ala
225                 230                 235                 240

Gln Glu Val Asp Tyr Gly Gly Val Leu Pro Ser Gly Asp Gly Thr Tyr
                245                 250                 255

Gln Thr Trp Leu Ser Val Asn Leu Asp Pro Gln Ser Asn Asp Val Tyr
            260                 265                 270

Ser Cys His Val Glu His Cys Gly Arg Gln Met Val Leu Glu Ala Pro
        275                 280                 285

```
Arg Glu Ser Gly Asp Ile Leu Arg Val Ser Thr Ile Ser Gly Thr Thr
290                 295                 300

Ile Leu Ile Ile Ala Leu Ala Gly Val Gly Val Leu Ile Trp Arg Arg
305                 310                 315                 320

Ser Gln Glu Leu Lys Glu Val Met Tyr Gln Pro Thr Gln Val Asn Glu
                325                 330                 335

Gly Ser Ser Pro Ser
                340
```

<210> SEQ ID NO 5
<211> LENGTH: 322
<212> TYPE: PRT
<213> ORGANISM: Mus musculus

<400> SEQUENCE: 5

```
Arg Thr His Ser Leu Arg Tyr Phe Arg Leu Ala Val Ser Asp Pro Gly
1               5                   10                  15

Pro Val Val Pro Glu Phe Ile Ser Val Gly Tyr Val Asp Ser His Pro
                20                  25                  30

Ile Thr Thr Tyr Asp Ser Val Thr Arg Gln Lys Glu Pro Lys Ala Pro
                35                  40                  45

Trp Met Ala Glu Asn Leu Ala Pro Asp His Trp Glu Arg Tyr Thr Gln
50                  55                  60

Leu Leu Arg Gly Trp Gln Gln Thr Phe Lys Ala Glu Leu Arg His Leu
65                  70                  75                  80

Gln Arg His Tyr Asn His Ser Gly Leu His Thr Tyr Gln Arg Met Ile
                85                  90                  95

Gly Cys Glu Leu Leu Glu Asp Gly Ser Thr Thr Gly Phe Leu Gln Tyr
                100                 105                 110

Ala Tyr Asp Gly Gln Asp Phe Ile Ile Phe Asn Lys Asp Thr Leu Ser
                115                 120                 125

Trp Leu Ala Met Asp Tyr Val Ala His Ile Thr Lys Gln Ala Trp Glu
130                 135                 140

Ala Asn Leu His Glu Leu Gln Tyr Gln Lys Asn Trp Leu Glu Glu Glu
145                 150                 155                 160

Cys Ile Ala Trp Leu Lys Arg Phe Leu Glu Tyr Gly Arg Asp Thr Leu
                165                 170                 175

Glu Arg Thr Glu His Pro Val Val Arg Thr Thr Arg Lys Glu Thr Phe
                180                 185                 190

Pro Gly Ile Thr Thr Phe Phe Cys Arg Ala His Gly Phe Tyr Pro Pro
                195                 200                 205

Glu Ile Ser Met Thr Trp Met Lys Asn Gly Glu Glu Ile Ala Gln Glu
210                 215                 220

Val Asp Tyr Gly Gly Val Leu Pro Ser Gly Asp Gly Tyr Gln Thr
225                 230                 235                 240

Trp Leu Ser Val Asn Leu Asp Pro Gln Ser Asn Asp Val Tyr Ser Cys
                245                 250                 255

His Val Glu His Cys Gly Arg Gln Met Val Leu Glu Ala Pro Arg Glu
                260                 265                 270

Ser Gly Asp Ile Leu Arg Val Thr Ile Ser Gly Thr Thr Ile Leu Ile
                275                 280                 285

Ile Ala Leu Ala Gly Val Gly Val Leu Ile Trp Arg Arg Ser Gln Glu
                290                 295                 300

Leu Lys Glu Val Met Tyr Gln Pro Thr Gln Val Asn Glu Gly Ser Ser
305                 310                 315                 320
```

```
Pro Ser

<210> SEQ ID NO 6
<211> LENGTH: 18
<212> TYPE: PRT
<213> ORGANISM: Mus musculus

<400> SEQUENCE: 6

Met Met Leu Leu Leu Pro Leu Leu Ala Val Phe Leu Val Lys Arg Ser
1               5                   10                  15

His Thr
```